United States Patent
Fukuda et al.

(10) Patent No.: US 9,150,569 B2
(45) Date of Patent: Oct. 6, 2015

(54) NITROGEN-CONTAINING HETEROCYCLIC COMPOUND HAVING INHIBITORY EFFECT ON PRODUCTION OF KYNURENINE

(75) Inventors: Yuichi Fukuda, Shizuoka (JP); Toshimi Kanai, Shizuoka (JP)

(73) Assignee: KYOWA HAKKO KIRIN CO., LTD., Tokyo (JP)

(*) Notice: Subject to any disclaimer, the term of this patent is extended or adjusted under 35 U.S.C. 154(b) by 0 days.

(21) Appl. No.: 13/697,143

(22) PCT Filed: May 9, 2011

(86) PCT No.: PCT/JP2011/060654
§ 371 (c)(1),
(2), (4) Date: Nov. 9, 2012

(87) PCT Pub. No.: WO2011/142316
PCT Pub. Date: Nov. 17, 2011

(65) Prior Publication Data
US 2013/0065905 A1    Mar. 14, 2013

(30) Foreign Application Priority Data
May 10, 2010 (JP) .................................. 2010-108766

(51) Int. Cl.
C07D 401/12 (2006.01)
C07D 401/14 (2006.01)
C07D 403/12 (2006.01)
C07D 403/14 (2006.01)
C07D 471/04 (2006.01)
C07D 405/12 (2006.01)
C07D 413/14 (2006.01)
C07D 241/44 (2006.01)
C07D 417/12 (2006.01)

(52) U.S. Cl.
CPC ............ *C07D 471/04* (2013.01); *C07D 241/44* (2013.01); *C07D 401/12* (2013.01); *C07D 401/14* (2013.01); *C07D 403/12* (2013.01); *C07D 405/12* (2013.01); *C07D 413/14* (2013.01); *C07D 417/12* (2013.01)

(58) Field of Classification Search
CPC .. C07D 401/12; C07D 401/14; C07D 403/12; C07D 403/14; C07D 471/14
See application file for complete search history.

(56) References Cited

U.S. PATENT DOCUMENTS

| 6,083,951 | A | 7/2000 | Bradbury | |
| 8,673,908 | B2 * | 3/2014 | Amishiro et al. | 514/234.8 |
| 2009/0042868 | A1 | 2/2009 | Andersen et al. | |
| 2011/0312960 | A1 | 12/2011 | Gaillard et al. | |

FOREIGN PATENT DOCUMENTS

| EP | 2374802 | * 10/2011 |
| JP | 9-510987 | 11/1997 |
| JP | 2006-137723 | 6/2006 |
| JP | 2008-505937 | 2/2008 |
| JP | 2008-201756 | 9/2008 |
| JP | 2009-50615 | 3/2009 |
| WO | 97/32858 | 9/1997 |
| WO | 00/42026 | 7/2000 |
| WO | 03/051870 | 5/2003 |
| WO | 03/059893 | 7/2003 |
| WO | 2004/007472 | 1/2004 |
| WO | 2005/021513 | 3/2005 |
| WO | 2005/023771 | 3/2005 |
| WO | 2006/005185 | 1/2006 |
| WO | 2007/023186 | 3/2007 |
| WO | 2007/044729 | 4/2007 |
| WO | 2008/101979 | 8/2008 |
| WO | 2010/053182 | 5/2010 |

OTHER PUBLICATIONS

Extended European Search Report issued Jan. 16, 2014 in corresponding European Patent Application No. 11780573.9.
English translation of Written Opinion of the International Searching Authority issued May 31, 2011 in International Application No. PCT/JP2011/060654.
International Search Report issued May 31, 2011 in International (PCT) Application No. PCT/JP2011/060654.
R. H. Bradbury et al., "New Non-Peptide Endothelin-A Receptor Antagonists: Synthesis, Biological Properties, and Structure-Activity Relationships of 5-(Dimethylamino)-N-pyridyl-, -N-pyrimidinyl-, -N-pyridazinyl-, and -N-pyrazinyl-1-naphthalenesulfonamides", J. Med. Chem., vol. 40, pp. 996-1004, 1997.

* cited by examiner

*Primary Examiner* — Jeffrey S Lundgren
*Assistant Examiner* — Chris Simmons
(74) *Attorney, Agent, or Firm* — Wenderoth, Lind & Ponack, L.L.P.

(57) ABSTRACT

The present invention provides a nitrogen-containing heterocyclic compound or a pharmaceutically acceptable salt thereof having an inhibitory effect on the production of kynurenine, represented by formula (I):

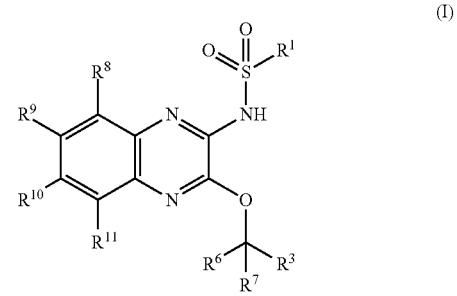

(wherein
$R^6$ and $R^7$ may be the same or different and each represent a hydrogen atom or the like,
$R^8$, $R^9$, $R^{10}$, and $R^{11}$ may be the same or different and each represent a hydrogen atom or the like,
$R^1$ represents lower alkyl which may be substituted with cycloalkyl, or the like, and
$R^3$ represents optionally substituted aryl or an optionally substituted heterocyclic group).

1 Claim, No Drawings

NITROGEN-CONTAINING HETEROCYCLIC COMPOUND HAVING INHIBITORY EFFECT ON PRODUCTION OF KYNURENINE

This application is a U.S. national stage of International Application No. PCT/JP2011/060654 filed May 9, 2011.

TECHNICAL FIELD

The present invention relates to a nitrogen-containing heterocyclic compound having an inhibitory effect on the production of kynurenine or a pharmaceutically acceptable salt thereof; a kynurenine production inhibitor comprising one or more of said compound or salt thereof as an active ingredient; and the like.

BACKGROUND ART

Cancer cells excessively express tumor-associated antigens. The host immune system is considered to respond to the tumor-associated antigens and exert cellular immunity to eliminate the tumor. However, there exist various types of immune escape mechanisms in the tumor microenvironment or throughout the body, and when the host fails to eliminate the tumor, the tumor grows.

Recently it has been reported that indoleamine 2,3-dioxygenase (IDO), which is a tryptophan-metabolizing enzyme, inhibits the proliferation of T cells and NK cells and activates regulatory T cells, thereby causing the depression of the host immune system. The expression of IDO is increased in tumor tissues and induced by IFN-γ stimulation in cancer cells and dendritic cells (for example, J. Clin. Invest., vol. 117, No. 5, pp. 1147-1154 (2007)). In a human body, 90% of an essential amino acid, tryptophan, is metabolized into kynurenine and subsequently into 3OH-kynurenine, quinolinic acid, and the like in the kynurenine pathway, the initiation step of which involves IDO. Activation of IDO decreases the tryptophan concentration and increases the kynurenine concentration in a local or systemic manner, and the tryptophan metabolites including kynurenine induce the death of T cells and NK cells (for example, J. Exp. Med., vol. 196, No. 4, pp. 447-457 (2002)). The tryptophan metabolism also induces the conversion of $CD4^+CD25^-$ T cells into regulatory T cells (for example, Blood, vol. 109, No. 7, pp. 2871-2877 (2007)). In the culture supernatant of dendritic cells in which the expression of IDO is induced by INF-γ, the tryptophan concentration is decreased and the kynurenine concentration is increased. When T cells are co-cultured with such dendritic cells, T cell proliferation is suppressed compared to co-culture with unstimulated dendritic cells (for example, J. Exp. Med., vol. 196, No. 4, pp. 447-457 (2002)).

From the above, in the tumor environment with an increased expression of IDO, an increased kynurenine concentration induced by tryptophan metabolism suppresses antitumor effector cells, which is considered to be one of the immune escape mechanisms in tumors (for example, J. Clin. Invest., vol. 117, No. 5, pp. 1147-1154 (2007)).

An increased expression of IDO in the tumor tissues of colorectal cancer and prostate cancer has been reported (for example, Clin. Cancer Res., vol. 12, No. 4, pp. 1144-1151 (2006); and Eur. J. Cancer, vol. 44, No. 15, pp. 2266-2275 (2008)). In acute myeloid leukemia cells, IDO is constantly expressed (for example, Leukemia, vol. 21, pp. 353-355 (2007)). It has also been reported that when patients with endometrial cancer, melanoma or ovarian cancer has an increased expression of IDO, the patients will have a poor prognosis (for example, Br. J. Cancer, vol. 95, No. 11, pp. 1555-1561 (2006); J. Clin. Invest., vol. 114, No. 2, pp. 280-290 (2004); and Clin. Cancer Res., vol. 11, No. 16, pp. 6030-6039 (2005)). In adult T cell leukemia lymphoma and acute myeloid leukemia, the kynurenine/tryptophan ratio in the blood is increased (for example, Leuk. Res., vol. 33, No. 1, pp. 39-45 (2009); and Leuk. Res., vol. 33, No. 3, pp. 490-494 (2009)). It has also been reported that melanoma patients with an increased kynurenine/tryptophan ratio in the blood will have a poor prognosis (for example, Dermatology, vol. 214, No. 1, pp. 8-14 (2007)). As described above, IDO and/or kynurenine is considered to be involved in various types of solid cancers and hematologic cancers.

A tryptophan derivative, 1-methyltryptophan (1-MT), antagonizes tryptophan, thereby inhibiting the production of kynurenine (for example, Cancer Res., vol. 67, No. 2, pp. 792-800 (2007)). 1-MT cancels the suppression of T cell proliferation in the presence of IDO-expressing cancer cells or IDO-expressing dendritic cells (for example, Cancer Res., vol. 67, No. 2, pp. 792-800 (2007)). Further, 1-MT induces major histocompatibility complex (MHC)-restricted rejection in allogeneic pregnant mice (for example, Nat. Immunol., vol. 2, No. 1, pp. 64-68 (2001)). These results suggest that inhibition of IDO suppresses the production of kynurenine and induces immunity.

1-MT shows an antitumor effect in tumor-bearing mice with mouse melanoma cells. This effect disappears in immunodeficient mice (for example, Cancer Res., vol. 67, No. 2, pp. 792-800 (2007)). These results suggest that the antitumor effect of 1-MT is based on immunostimulation by IDO inhibition-mediated inhibitory effect on the production of kynurenine.

In addition, compounds showing an inhibitory effect on the production of kynurenine and/or on IDO are known to exhibit an immunostimulatory effect (for example, Nat. Immunol., vol. 2, pp. 64-68 (2001)).

It has been reported that the IDO expression in PBMC correlates with the viral load in HIV positive patients (for example, Blood, vol. 109, pp. 3351-3359 (2007)). It has also been reported that chronic hepatitis C patients have an increased IDO mRNA level in the liver and an increased serum kynurenine/tryptophan ratio (for example, J. Virol., vol. 81, No. 7, pp. 3662-3666 (2007)).

Further, compounds showing an inhibitory effect on the production of kynurenine and/or on IDO are known to be useful as an antitumor agent, an anti-AIDS agent, an anti-AIDS dementia agent, anti-Alzheimer's disease agent, an antidepressant, and the like (for example, J Clin Invest., vol. 117, pp. 1147-1154 (2007); J Virol., vol. 81, pp. 11593-11603 (2007); Neuropathol Appl Neurobiol., vol. 31, pp. 395-404 (2005); Neurosci Lett., vol. 187, pp. 9-12 (1995); and Neuropsychopharmacology, vol. 33, pp. 2341-2351 (2008)).

As described above, IDO inhibitors and/or kynurenine production inhibitors are considered to be promising preventive or therapeutic agents for diseases involving the production of kynurenine, such as cancers, AIDS, AIDS dementia, Alzheimer's disease, depression, infections, and immune diseases.

Pyrazine derivatives having an antagonistic effect on endothelin are known (see Patent Literature 1 and Non Patent literature 1).

Compounds known as a therapeutic agent for diseases in which chemokines are involved are N-pyrazinyl-2-thiophenesulfonamide derivatives (see Patent Literature 2), N-pyrazinylbenzenesulfonamide derivatives (see Patent Literature 3), N-(2-quinoxanyl)benzenesulfonamide derivatives (see Patent Literature 4), and the like. Compounds known as a chemokine receptor antagonist are N-pyrazinylbenzenesulfonamide derivatives, N-(2-quinoxalinyl)benzenesulfonamide derivatives (see Patent Literature 5 and 6), pyridopyrazin-2-on-3-ylmethanesulfonamide derivatives (see Patent Literature 7), and the like. Compounds known as a functional modulator of thymus and activation-regulated chemokine (TARC: CC chemokine ligand 17 (CCL17)) and/or of macrophage-derived chemokine (MDC: CC chemokine ligand 22

(CCL22)) are N-pyrazinylbenzenesulfonamide derivatives, N-(2-pyridopyrazinyl)benzenesulfonamide derivatives (see Patent Literature 8), and the like.

Compounds known for having an inhibitory activity on phosphatidylinositol-3-kinase (PI3K) are N-(2-quinoxanyl) benzenesulfonamide derivatives (see Patent Literatures 9 and 10), and the like.

A nitrogen-containing heterocyclic compound having an inhibitory effect on the production of kynurenine (see Patent Literature 11) is also known.

PRIOR ART

Patent Literature
Patent Literature 1: JP 9-510987 T
Patent Literature 2: WO 03/051870
Patent Literature 3: WO 03/059893
Patent Literature 4: WO 05/021513
Patent Literature 5: WO 04/007472
Patent Literature 6: WO 05/023771
Patent Literature 7: WO 97/032858
Patent Literature 8: JP 2006-137723 A
Patent Literature 9: WO 07/044,729
Patent Literature 10: WO 07/023,186
Patent Literature 11: WO 2010/053182

Non Patent Literature

Non Patent Literature 1: Journal of Medicinal Chemistry, 1997, vol. 40, p. 996

SUMMARY OF INVENTION

Problems to be Solved by Invention

An object of the present invention is to provide a nitrogen-containing heterocyclic compound having an inhibitory effect on the production of kynurenine or a pharmaceutically acceptable salt thereof; a kynurenine production inhibitor comprising one or more of said compound or salt thereof as an active ingredient; and the like.

Means for Solving the Problems

The present invention relates to the following (1) to (20).
(1) A nitrogen-containing heterocyclic compound represented by formula (I):

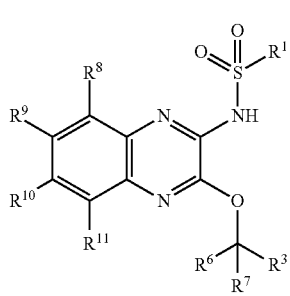

(wherein
$R^6$ and $R^7$ may be the same or different and each represent a hydrogen atom, optionally substituted lower alkyl, optionally substituted cycloalkyl, or optionally substituted aryl, $R^8$, $R^9$, $R^{10}$, and $R^{11}$ may be the same or different and each represent a hydrogen atom, halogen, cyano, optionally substituted lower alkyl, optionally substituted lower alkenyl, or optionally substituted lower alkynyl, $R^1$ represents lower alkyl which may be substituted with cycloalkyl or lower alkyl which may be substituted with lower alkoxy, and $R^3$ represents optionally substituted aryl or an optionally substituted heterocyclic group; excluding the following cases:

(a) $R^1$ represents methyl, ethyl, propyl, isopropyl, butyl, isobutyl, sec-butyl, 2-methoxyethyl, or 3-methoxypropyl,
$R^3$ represents pyridin-3-yl,
$R^6$ represents a hydrogen atom,
$R^8$, $R^9$, $R^{10}$, and $R^{11}$ each represent a hydrogen atom, and
$R^7$ represents trifluoromethyl;

(b) $R^1$ represents propyl,
$R^3$ represents 1-methyl-1H-indol-2-yl, 6-methylpyridin-3-yl, 2-chlorothiazol-5-yl, 4-{(dimethylamino)methyl}phenyl, 4-cyanophenyl, tetrahydro-2H-pyran-4-yl, pyridine-1-oxide-3-yl, 1-methyl-2(1H)pyridon-5-yl, tetrahydro-2H-thiopyran-1,1-dioxide-4-yl, thiazol-5-yl, 1-methyl-1H-imidazol-5-yl, 6-chloropyridin-3-yl, 2-methylpyridine-1-oxide-5-yl, 3-cyanophenyl, 4-chlorophenyl, 2-methylthiazol-5-yl, 1-methylpiperidin-4-yl, piperidin-4-yl, 1-acetylpiperidin-4-yl, 5-methylpyridin-3-yl, 5-fluoropyridin-3-yl, 1-methyl-2(1H)pyridon-4-yl, 5-methoxypyridin-3-yl, 5-chloropyridin-3-yl, 1-methanesulfonylpiperidin-4-yl, 1-methoxycarbonylpiperidin-4-yl, 1-propionylpiperidin-4-yl, 1-cyclopropylcarbonylpiperidin-4-yl, 2-methylthiazol-4-yl, 4-fluorotetrahydro-2H-pyran-4-yl, 4-cyanotetrahydro-2H-pyran-4-yl, 4-hydroxytetrahydro-2H-pyran-4-yl, 4-methoxytetrahydro-2H-pyran-4-yl, 1-acetyl-4-fluoropiperidin-4-yl, 4-fluoro-1-methanesulfonylpiperidin-4-yl, 1-acetyl-4-methylpiperidin-4-yl, or 1-methanesulfonyl-4-methylpiperidin-4-yl,
$R^6$ represents a hydrogen atom,
$R^8$, $R^9$, $R^{10}$, and $R^{11}$ each represent a hydrogen atom, and
$R^7$ represents trifluoromethyl;

(c) $R^1$ represents propyl,
$R^3$ represents pyridin-3-yl or pyridine-1-oxide-3-yl,
$R^6$ represents a hydrogen atom, $R^9$, $R^9$, $R^{10}$, and $R^{11}$ each represent a hydrogen atom, and
$R^7$ represents isopropyl;

(d) $R^1$ represents propyl,
$R^3$ represents 2-methylthiazol-5-yl,
$R^8$, $R^9$, $R^{10}$, and $R^{11}$ each represent a hydrogen atom, and
$R^6$ and $R^7$ each represent a hydrogen atom; and (e) $R^1$ represents cyclopropylmethyl,
$R^3$ represents pyridin-3-yl, 6-methylpyridin-3-yl, 2-methylthiazol-5-yl, 6-chloropyridin-3-yl, or 3-cyanophenyl,
$R^6$ represents a hydrogen atom,
$R^8$, $R^9$, $R^{10}$, and $R^{11}$ each represent a hydrogen atom, and
$R^7$ represents trifluoromethyl)
or a pharmaceutically acceptable salt thereof.

(2) The nitrogen-containing heterocyclic compound or a pharmaceutically acceptable salt thereof according to (1), wherein $R^6$ represents a hydrogen atom.

(3) The nitrogen-containing heterocyclic compound or a pharmaceutically acceptable salt thereof according to (1) or (2), wherein $R^7$ represents lower alkyl substituted with fluorine.

(4) The nitrogen-containing heterocyclic compound or a pharmaceutically acceptable salt thereof according to (1) or (2), wherein $R^7$ represents trifluoromethyl.

(5) The nitrogen-containing heterocyclic compound or a pharmaceutically acceptable salt thereof according to any of (1) to (4), wherein $R^3$ represents an optionally substituted heterocyclic group.

(6) The nitrogen-containing heterocyclic compound or a pharmaceutically acceptable salt thereof according to any of (1) to (4), wherein $R^3$ represents optionally substituted pyridyl or an optionally substituted bicyclic aromatic heterocyclic group.

(7) The nitrogen-containing heterocyclic compound or a pharmaceutically acceptable salt thereof according to any of (1) to (4), wherein $R^3$ represents optionally substituted pyridin-3-yl.

(8) The nitrogen-containing heterocyclic compound or a pharmaceutically acceptable salt thereof according to (7), wherein the substituent of the optionally substituted pyridin-3-yl is a heterocyclic group which may be substituted with lower alkyl.

(9) The nitrogen-containing heterocyclic compound or a pharmaceutically acceptable salt thereof according to any of (1) to (8), wherein $R^9$, $R^9$, $R^{10}$, and $R^{11}$ may be the same or different and each represent a hydrogen atom, halogen, cyano, or lower alkynyl.

(10) The nitrogen-containing heterocyclic compound or a pharmaceutically acceptable salt thereof according to any of (1) to (8), wherein $R^8$, $R^{10}$, and $R^{11}$ each represent a hydrogen atom and $R^9$ represents halogen, cyano, or lower alkynyl.

(11) The nitrogen-containing heterocyclic compound or a pharmaceutically acceptable salt thereof according to any of (1) to (8), wherein $R^1$ is lower alkyl which may be substituted with cycloalkyl and $R^8$, $R^9$, $R^{10}$, and $R^{11}$ each represent a hydrogen atom.

(12) A pharmaceutical composition comprising, as an active ingredient, the nitrogen-containing heterocyclic compound or a pharmaceutically acceptable salt thereof described in any of (1) to (11).

(13) A kynurenine production inhibitor comprising, as an active ingredient, the nitrogen-containing heterocyclic compound or a pharmaceutically acceptable salt thereof described in any of (1) to (11).

(14) A method for inhibiting the production of kynurenine, comprising a step of administering an effective amount of the nitrogen-containing heterocyclic compound or a pharmaceutically acceptable salt thereof described in any of (1) to (11).

(15) Use of the nitrogen-containing heterocyclic compound or a pharmaceutically acceptable salt thereof described in any of (1) to (11) for the manufacture of a kynurenine production inhibitor.

(16) The nitrogen-containing heterocyclic compound or a pharmaceutically acceptable salt thereof according to any of (1) to (11) for use in inhibiting the production of kynurenine.

(17) A preventive or therapeutic agent for a disease involving the production of kynurenine, comprising, as an active ingredient, the nitrogen-containing heterocyclic compound or a pharmaceutically acceptable salt thereof described in any of (1) to (11).

(18) A method for preventing or treating a disease involving the production of kynurenine, comprising a step of administering an effective amount of the nitrogen-containing heterocyclic compound or a pharmaceutically acceptable salt thereof described in any of (1) to (11).

(19) Use of the nitrogen-containing heterocyclic compound or a pharmaceutically acceptable salt thereof described in any of (1) to (11) for the manufacture of a preventive or therapeutic agent for a disease involving the production of kynurenine.

(20) The nitrogen-containing heterocyclic compound or a pharmaceutically acceptable salt thereof according to any of (1) to (11) for use in preventing or treating a disease involving the production of kynurenine.

Effects of Invention

The present invention provides a nitrogen-containing heterocyclic compound having an inhibitory effect on the production of kynurenine or a pharmaceutically acceptable salt thereof; a kynurenine production inhibitor comprising one or more of said compound or salt thereof as an active ingredient; and the like.

MODE FOR CARRYING OUT THE INVENTION

Hereinafter, the compound represented by the above formula (I) is referred to as Compound (I). The same applies to the other compounds having different formula numbers.

The definitions of the respective groups in the formula (I) are as follows.

(i) Examples of the lower alkyl and the lower alkyl moieties of the lower alkyl substituted with fluorine and the lower alkoxy include linear or branched alkyl having 1 to 10 carbon atoms. More specific examples thereof include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, and the like.

(i-1) Examples of the lower alkenyl include linear or branched alkenyl having 2 to 10 carbon atoms. More specific examples thereof include vinyl, allyl, 1-propenyl, butenyl, pentenyl, hexenyl, heptenyl, octenyl, nonenyl, decenyl, and the like.

(i-2) Examples of the lower alkynyl include linear or branched alkynyl having 2 to 10 carbon atoms. More specific examples thereof include ethynyl, propynyl, butynyl, pentynyl, hexynyl, heptynyl, octynyl, nonynyl, decynyl, and the like.

(ii) Examples of the cycloalkyl include cycloalkyl having 3 to 10 carbon atoms. More specific examples thereof include cyclopropyl, cyclobutyl, cyclopentyl, cyclohexyl, cycloheptyl, cyclooctyl, cyclodecyl, noradamantyl, adamantyl, bicyclo[2,2,1]heptyl, bicyclo[2,2,2]octyl, bicyclo[3,3,0]octyl, bicyclo[3,3,1]nonyl, and the like.

(iii) Examples of the aryl include monocyclic aryl and fused aryl in which two or more rings are fused. More specific examples thereof include aryl having 6 to 14 ring carbon atoms, such as phenyl, naphthyl, indenyl, and anthranil.

(iv) Examples of the heterocyclic group include an aromatic heterocyclic group, an aliphatic heterocyclic group, and the like.

Examples of the aromatic heterocyclic group include a 5- or 6-membered monocyclic aromatic heterocyclic group which contains at least one heteroatom selected from a nitrogen atom, an oxygen atom and a sulfur atom; a bicyclic aromatic heterocyclic group in which 3- to 8-membered rings are fused and which contains at least one heteroatom selected from a nitrogen atom, an oxygen atom and a sulfur atom; a tricyclic aromatic heterocyclic group in which 3- to 8-membered rings are fused and which contains at least one heteroatom selected from a nitrogen atom, an oxygen atom and a sulfur atom; and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridyl-1-oxide, pyridazinyl, pyrimidinyl, pyrazinyl, triazinyl, benzofuranyl, benzothiophenyl, benzoxazolyl, benzoxadiazolyl benzothiazolyl, isoindolyl, indolyl, indazolyl, benzimidazolyl, benzotriazolyl, oxazolopyrimidinyl, thiazolopyrimidinyl, pyrrolopyridyl, pyrrolopyrimidinyl, imidazopyridyl, imidazopyrimidinyl, triazolopyridyl, triazolopyrimidinyl, purinyl, quinolinyl, isoquinolinyl, cinnolinyl, phthalazinyl, quinazolinyl, quinoxalinyl, naphthyridinyl, and the like. Among these, preferred as the bicyclic aromatic heterocyclic groups are benzofuranyl, benzothiophenyl, benzoxazolyl, benzoxadiazolyl, benzothiazolyl, isoindolyl, indolyl, indazolyl, benzimidazolyl, benzotriazolyl, oxazolopyrimidinyl, thiazolopyrimidinyl, pyrrolopyridyl, pyrrolopyrimidinyl, imidazopyridyl, imidazopyrimidinyl, triazolopyridyl, triazolopyrimidinyl, purinyl, quinolinyl, isoquinolinyl, cinnolinyl, phthalazinyl, quinazolinyl, quinoxalinyl, naphthyridinyl, and the like.

Examples of the aliphatic heterocyclic group include a 5- or 6-membered monocyclic aliphatic heterocyclic group which contains at least one heteroatom selected from a nitrogen atom, an oxygen atom and a sulfur atom; a bicyclic or tricyclic fused aliphatic heterocyclic group in which 3- to 8-membered rings are fused and which contains at least one heteroatom selected from a nitrogen atom, an oxygen atom and a sulfur atom; and the like. More specific examples thereof include aziridinyl, azetidinyl, pyrrolidinyl, piperidino, piperidinyl, quinuclidinyl, azepanyl, 1,2,5,6-tetrahydropyridyl, 1,2-dihydropyridyl, imidazolidinyl, pyrazolidinyl, piperazinyl, homopiperazinyl, pyrazolinyl, oxiranyl, oxetanyl, tetrahydrofuranyl, tetrahydro-2H-pyranyl, 5,6-dihydro-2H-pyranyl, 1,4-dioxanyl, 1,3-dioxanyl, tetrahydro-2H-thiopyranyl, tetrahydro-2H-thiopyranyl-1,1-dioxide, tetrahydro-2H-thiopyranyl-1-oxide, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, 3,4-dihydro-2H-benzo[b][1,4]oxazinyl, 2,3-dihydrobenzo[b][1,4]dioxinyl, benzo[d][1,3]dioxolyl, tetrahydroquinolyl, tetrahydroisoquinolyl, chromanyl, thiochromanyl, tetrahydroquinoxalinyl, tetrahydroquinazolinyl, and the like.

(v) Halogen means each atom of a fluorine atom, a chlorine atom, a bromine atom, and an iodine atom.

(x) The substituents of the optionally substituted lower alkyl, the optionally substituted lower alkenyl, the optionally substituted lower alkynyl, and the optionally substituted cycloalkyl may be the same or different and the number of the substituents of these groups is from 1 to the highest possible number of substitution, preferably 1 to 3, and examples of the substituents include a substituent selected from the group consisting of:

(x-a) halogen,
(x-b) hydroxy,
(x-c) cyano,
(x-d) carboxy,
(x-e) optionally substituted lower alkoxycarbonyl (the number of the substituents of the optionally substituted lower alkoxycarbonyl is 1 to 3 and examples of the substituents include a substituent selected from the group consisting of halogen, hydroxy, sulfanyl, nitro, cyano, carboxy, carbamoyl, cycloalkyl, aryl, an aliphatic heterocyclic group, an aromatic heterocyclic group, lower alkoxy, cycloalkoxy, aryloxy, aralkyloxy, lower alkanoyloxy, aroyloxy, lower alkylsulfanyl, —NR$^X$R$^Y$ (wherein R$^X$ and R$^Y$ may be the same or different and each represent a hydrogen atom, lower alkyl, cycloalkyl, aryl, an aromatic heterocyclic group, aralkyl, lower alkanoyl, aroyl, lower alkoxycarbonyl, aralkyloxycarbonyl, or the like), lower alkanoyl, aroyl, lower alkoxycarbonyl, aryloxycarbonyl, lower alkylcarbamoyl, di-lower alkylcarbamoyl, and the like), (x-f) optionally substituted cycloalkyl (the number of the substituents of the optionally substituted cycloalkyl is 1 to 3 and examples of the substituents include a substituent selected from the group consisting of oxo, halogen, hydroxy, sulfanyl, nitro, cyano, carboxy, carbamoyl, lower alkyl, trifluoromethyl, cycloalkyl, aryl, an aliphatic heterocyclic group, an aromatic heterocyclic group, lower alkoxy, cycloalkoxy, aryloxy, aralkyloxy, lower alkanoyloxy, aroyloxy, lower alkylsulfanyl, —NR$^{X1}$R$^{Y1}$ (wherein R$^{X1}$ and R$^{Y1}$ may be the same or different and each represent a hydrogen atom, lower alkyl, cycloalkyl, aryl, an aromatic heterocyclic group, aralkyl, lower alkanoyl, aroyl, lower alkoxycarbonyl, aralkyloxycarbonyl, or the like), lower alkanoyl, aroyl, lower alkoxycarbonyl, aryloxycarbonyl, lower alkylcarbamoyl, di-lower alkylcarbamoyl, and the like), (x-g) optionally substituted lower alkoxy (examples of the substituents of the optionally substituted lower alkoxy include the groups exemplified in the above substituents of the optionally substituted lower alkoxycarbonyl (x-e), and the like), (x-h) optionally substituted aryl (the number of the substituents of the optionally substituted aryl is 1 to 3 and examples of the substituents include a substituent selected from the group consisting of halogen, hydroxy, sulfanyl, nitro, cyano, carboxy, carbamoyl, lower alkyl, trifluoromethyl, cycloalkyl, an aliphatic heterocyclic group, an aromatic heterocyclic group, lower alkoxy, cycloalkoxy, aryloxy, aralkyloxy, lower alkanoyloxy, aroyloxy, lower alkylsulfanyl, lower alkylsulfinyl, lower alkylsulfonyl, —NR$^{X2}$R$^{Y2}$ (wherein —NR$^{X2}$ (wherein R$^{X2}$ and R$^{Y2}$ may be the same or different and each represent a hydrogen atom, lower alkyl, cycloalkyl, aryl, an aromatic heterocyclic group, aralkyl, lower alkanoyl, aroyl, lower alkoxycarbonyl, aralkyloxycarbonyl, or the like), lower alkanoyl, aroyl, lower alkoxycarbonyl, aryloxycarbonyl, lower alkylcarbamoyl, di-lower alkylcarbamoyl, and the like), (x-i) an optionally substituted heterocyclic group {examples of the substituents of the optionally substituted heterocyclic group include the groups exemplified in the substituents of the above optionally substituted aryl (x-h), and the like and, when the heterocyclic group of the optionally substituted heterocyclic group is an aliphatic heterocyclic group, the examples also include oxo, and the like}, (x-j) —NR$^{31}$R$^{32}$ {wherein R$^{31}$ and R$^{32}$ may be the same or different and each represent a hydrogen atom, lower alkoxycarbonyl, lower alkenyl, lower alkynyl, lower alkanoyl, optionally substituted lower alkyl (examples of the substituents of the optionally substituted lower alkyl include the groups exemplified in the substituents of the above optionally substituted lower alkoxycarbonyl (x-e), and the like), optionally substituted cycloalkyl (examples of the substituents of the optionally substituted cycloalkyl include the groups exemplified in the substituents of the above optionally substituted cycloalkyl (x-f), and the like), optionally substituted aryl (examples of the substituents of the optionally substituted aryl include the groups exemplified in the substituents of the above optionally substituted aryl (x-h), and the like), an optionally substituted heterocyclic group (examples of the substituents of the optionally substituted heterocyclic group include the groups exemplified in the substituents of the above optionally substituted heterocyclic group (x-i), and the like)}, (x-k) —CONR$^{33}$R$^{34}$ {wherein R$^{33}$ and R$^{34}$ may be the same or different and each represent a hydrogen atom, optionally substituted lower alkyl (examples of the substituents of the optionally substituted lower alkyl include the groups exemplified in the substituents of the above optionally substituted lower alkoxycarbonyl (x-e), and the like), optionally substituted cycloalkyl (examples of the substituents of the optionally substituted cycloalkyl include the groups exemplified in the substituents of the above optionally substituted cycloalkyl (x-f), and the like), lower alkanoyl, or the like; or $R^{33}$ and $R^{34}$ are combined together with the adjacent nitrogen atom to form a nitrogen-containing heterocyclic group}, (x-l) optionally substituted lower alkylsulfonyl (examples of the substituents of the optionally substituted lower alkylsulfonyl include the groups exemplified in the substituents of the above optionally substituted lower alkoxycarbonyl (x-e), and the like), and (x-m) tri(lower alkyl)silyloxy, and the like.

Examples of the substituents of the optionally substituted cycloalkyl also include lower alkyl, and the like in addition to the above substituents.

(xi) The substituents of the optionally substituted aryl, the optionally substituted pyridyl, the optionally substituted pyridin-3-yl, the optionally substituted bicyclic aromatic heterocyclic group, and the optionally substituted heterocyclic group may be the same or different and the number of the substituents of these groups is 1 to 3 and examples of the substituents include a substituent selected from the group consisting of:

(xi-a) halogen,
(xi-b) hydroxy,
(xi-c) cyano,
(xi-d) formyl,
(xi-e) carboxy,
(xi-f) optionally substituted lower alkoxycarbonyl (examples of the substituents of the optionally substituted lower alkoxycarbonyl include the groups exemplified in the substituents (x) of the above optionally substituted lower alkyl, and the like, and the like),
(xi-g) optionally substituted lower alkyl (examples of the substituents of the optionally substituted lower alkyl include the groups exemplified in the substituents (x) of the above optionally substituted lower alkyl, and the like, and the like),
(xi-h) optionally substituted lower alkoxy (examples of the substituents of the optionally substituted lower alkoxy include the groups exemplified in the substituents (x) of the above optionally substituted lower alkyl, and the like, and the like),
(xi-i) optionally substituted lower alkanoyl (examples of the substituents of the optionally substituted lower alkanoyl include the groups exemplified in the substituents (x) of the above optionally substituted lower alkyl, and the like, and the like),
(xi-j) optionally substituted lower alkylsulfanyl (examples of the substituents of the optionally substituted lower alkylsulfanyl include the groups exemplified in the substituents (x) of the above optionally substituted lower alkyl, and the like, and the like),
(xi-k) optionally substituted lower alkylsulfinyl (examples of the substituents of the optionally substituted lower alkylsulfinyl include the groups exemplified in the substituents (x) of the above optionally substituted lower alkyl, and the like, and the like),
(xi-l) optionally substituted lower alkylsulfonyl (examples of the substituents of the optionally substituted lower alkylsulfonyl include the groups exemplified in the substituents (x) of the above optionally substituted lower alkyl, and the like, and the like),
(xi-m) optionally substituted aryl (examples of the substituents of the optionally substituted aryl include the groups exemplified in the substituents of the above optionally substituted aryl (x-h), and the like),
(xi-n) an optionally substituted heterocyclic group (examples of the substituents of the optionally substituted heterocyclic group include the groups exemplified in the substituents of the above optionally substituted heterocyclic group (x-i), and the like),
(xi-o) —$NR^{35}R^{36}$ {wherein $R^{35}$ and $R^{36}$ may be the same or different and each represent a hydrogen atom, optionally substituted lower alkyl (examples of the substituents of the optionally substituted lower alkyl include the groups exemplified in the substituents (x) of the above optionally substituted lower alkyl, and the like, and the like), optionally substituted lower alkanoyl (examples of the substituents of the optionally substituted lower alkanoyl include the groups exemplified in the substituents (x) of the above optionally substituted lower alkyl, and the like, and the like), optionally substituted lower alkoxycarbonyl (examples of the substituents of the optionally substituted lower alkoxycarbonyl include the groups exemplified in the substituents (x) of the above optionally substituted lower alkyl, and the like, and the like), carbamoyl, optionally substituted lower alkylcarbamoyl (examples of the substituents of the optionally substituted lower alkylcarbamoyl include the groups exemplified in the substituents (x) of the above optionally substituted lower alkyl, and the like, and the like), optionally substituted di-lower alkylcarbamoyl (examples of the substituents of the optionally substituted di-lower alkylcarbamoyl include the groups exemplified in the substituents (x) of the above optionally substituted lower alkyl, and the like, and the like), optionally substituted aryl (examples of the substituents of the optionally substituted aryl include the groups exemplified in the substituents of the above optionally substituted aryl (x-h), and the like), or the like},
(xi-p) —$CONR^{37}R^{38}$ {wherein $R^{37}$ and $R^{38}$ may be the same or different and each represent a hydrogen atom, optionally substituted lower alkyl (examples of the substituents of the optionally substituted lower alkyl include the groups exemplified in the substituents (x) of the above optionally substituted lower alkyl, and the like, and the like), optionally substituted aryl (examples of the substituents of the optionally substituted aryl include the groups exemplified in the substituents of the above optionally substituted aryl (x-h), and the like), or the like; or $R^{37}$ and $R^{38}$ are combined together with the adjacent nitrogen atom to form an optionally substituted nitrogen-containing heterocyclic group (examples of the substituents of the optionally substituted nitrogen-containing heterocyclic group formed together with the adjacent nitrogen atom include the groups exemplified in the substituents of the above optionally substituted heterocyclic group (x-i), and the like)},
(xi-q) optionally substituted cycloalkyl (examples of the substituents of the optionally substituted cycloalkyl include the groups exemplified in the substituents (x-f) of the above optionally substituted cycloalkyl, and the like), and the like.

Examples of the substituents of the optionally substituted heterocycle group also include, in addition to the groups exemplified in the substituents of the above (xi-a) to (xi-q), the number of the substituents being 1 to 3,
(xi-r) oxo,
(xi-s) —$O(CR^{39}R^{40})_nO$— (wherein $R^{39}$ and $R^{40}$ may be the same or different and each represent a hydrogen atom, lower alkyl, or the like; n represents an integer of 1 to 3; and the two terminal oxygen atoms are bound to the same carbon atom in the heterocyclic group), and
(xi-t) optionally substituted cycloalkylcarbonyl (examples of the substituents of the optionally substituted cycloalkylcarbonyl include halogen, amino, hydroxy, and the like, the number of the substituents being 1 to 3).

(xii) Examples of the lower alkyl substituted with fluorine include lower alkyl substituted with a fluorine atom(s), the number of which is from 1 to the highest possible number of substitution, and the like. More specific examples thereof include trifluoromethyl, (1-fluoro-1-methyl) ethyl, 1,1,2,2,2-pentafluoroethyl, and the like.

In the groups exemplified in the above (x) to (xii), the lower alkyl and the lower alkyl moieties of the lower alkoxy, the lower alkoxycarbonyl, the lower alkanoyl, the lower alkanoyloxy, the lower alkylcarbamoyl, the di-lower alkylcarbamoyl, the lower alkylsulfanyl, the lower alkylsulfinyl, the lower alkylsulfonyl, and the tri-(lower alkyl) silyloxy have the same meanings as defined in the above lower alkyl (i). The two lower alkyl moieties of the di-lower alkyl carbamoyl may be the same or different, and the three lower alkyl moieties of the tri-(lower alkyl) silyloxy may be the same or different. The lower alkenyl has the same meaning as defined in the above (i-1) lower alkenyl. The lower alkynyl has the same meaning as defined in the above (i-2) lower alkynyl. The cycloalkyl and the cycloalkyl moieties of the cycloalkoxy and the cycloalkylcarbonyl have the same meanings as defined in the above cycloalkyl (ii). The aryl and the aryl moieties of the aryloxy, the aralkyl, the aralkyloxy, the aralkyloxycarbonyl, the aryloxycarbonyl, the aroyl, and the aroyloxy have the same meanings as defined in the above aryl (iii). Examples of the alkylene moieties of the aralkyl, the aralkyloxy, and the aralkyloxycarbonyl include an alkylene group which is derived from the groups exemplified in the above lower alkyl (i) by removing one hydrogen atom. The halogen has the same meaning as defined in the above halogen (v). The heterocyclic group has the same meaning as defined in the above heterocyclic group (iv). The aliphatic heterocyclic group refers to the aliphatic heterocyclic groups exemplified in the above heterocyclic group (iv). The aromatic heterocyclic group refers to the aromatic heterocyclic groups exemplified in the above heterocyclic group (iv). Examples of the nitrogen-containing heterocyclic group formed together with the adjacent nitrogen atom include a 5-or 6-membered monocyclic heterocyclic group which contains at least one nitrogen atom (the monocyclic heterocyclic group may contain a further nitrogen atom, an oxygen atom, or a sulfur atom), a bicyclic or tricyclic fused heterocyclic group in which 3- to 8-membered rings are fused and which contains at least one nitrogen atom (the fused heterocyclic group may contain a further nitrogen atom, an oxygen atom, or a sulfur atom), and the like. More specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridyl, pyrrolopyrimidinyl, imidazopyridyl, purinyl, and the like.

Examples of a pharmaceutically acceptable salt of Compound (I) include pharmaceutically acceptable acid addition salts, metal salts, ammonium salts, organic amine addition salts, amino acid addition salts, and the like. Examples of the acid addition salts include inorganic acid salts such as hydrochlorides, sulfates, and phosphates; organic acid salts such as acetates, trifluoroacetates, maleates, fumarates, tartrates, citrates, and lactates; and the like. Examples of the metal salts include alkali metal salts such as sodium salts and potassium salts; alkaline earth metal salts such as magnesium salts and calcium salts; aluminum salts; zinc salts; and the like. Examples of the ammonium salts include salts of ammonium, tetramethylammonium, and the like. Examples of the organic amine addition salts include addition salts of morpholine, piperidine, and the like. Examples of the amino acid addition salts include addition salts of lysine, glycine, phenylalanine, aspartic acid, glutamic acid, and the like.

When one or more of Compound (I) or a pharmaceutically acceptable salt thereof used in the present invention are (1) added to cells and the like in an in vitro system or (2) administered to a living body such as mammals, the production of kynurenine is inhibited in an in vitro system or a living body, in comparison with the case where the compound or a pharmaceutically acceptable salt thereof is not administered. That is, Compound (I) and a pharmaceutically acceptable salt thereof have an inhibitory effect on the production of kynurenine and consequently have an inhibitory effect on the increase in the kynurenine level. Compound (I) and a pharmaceutically acceptable salt thereof have an excellent inhibitory effect on the production of kynurenine and therefore are useful for, for example, prevention or treatment of a disease in which IDO and/or kynurenine is involved. Compound (I) and a pharmaceutically acceptable salt thereof are especially suitable as an active ingredient of a preventive or therapeutic agent for a disease involving the production of kynurenine, for example, a disease in which the local or systemic level of kynurenine is increased, and also as an active ingredient of a kynurenine production inhibitor. In particular, Compound (I) and a pharmaceutically acceptable salt thereof are suitable as an active ingredient of a preventive or therapeutic agent for diseases such as cancers (tumors), immune diseases, neurodegenerative diseases, and infections.

"Treatment" refers to alleviating or curing a condition or a disease and/or its accompanying symptom, and to alleviating the same. "Prevention" refers to delaying or preventing the development of a condition or a disease and its accompanying symptom, or to reducing the subject's risk of developing a condition or a disease.

Examples of the disease involving the production of IDO and/or kynurenine include cancers (tumors), immune diseases, neurodegenerative diseases, infections, and the like.

Examples of the cancers (tumors) include hematopoietic tumor, multiple myeloma, breast cancer, ovarian cancer, endometrial cancer, cervical cancer, prostate cancer, bladder cancer, renal cancer, gastric cancer, esophagus cancer, hepatic cancer, biliary tract cancer, colon cancer, rectal cancer, pancreatic cancer, lung cancer, head and neck cancer, osteosarcoma, melanoma, brain tumor, and the like. In particular, Compound (I) and a pharmaceutically acceptable salt thereof are suitable for prevention or treatment of gastric cancer, breast cancer, and the like.

Examples of the immune diseases include acquired immune deficiency syndrome (AIDS), bronchial asthma, pollen allergy, allergic rhinitis, atopic dermatitis, rheumatoid arthritis, ulcerative colitis, Crohn's disease, multiple sclerosis, amyotrophic lateral sclerosis, graft versus host disease, and the like.

Examples of the neurodegenerative diseases include AIDS dementia, Alzheimer's disease, depression, and the like.

Examples of the infections include viral infection, bacterial infection, fungal infection, chlamydial infection, rickettsial infection, and the like.

The above Compound (I) and a pharmaceutically acceptable salt thereof are especially suitable as an active ingredient for a preventive or therapeutic agent for cancers (tumors), and the like.

Hereinafter, production methods of Compound (I) will be described.

In the production methods described below, in cases where a defined group changes under the conditions of the implementation methods or is not suitable for carrying out the production methods, a method commonly used in synthetic organic chemistry for introducing and removing a protective group (for example, the method described in T. W. Greene, Protective Groups in Organic Synthesis, 3rd edition, John Wiley & Sons Inc. (1999), or the like), and the like may be used to produce a desired compound. The order of the reaction steps, such as introduction of a substituent, may be changed as necessary.

Compound (I) can be produced, for example, according to the following Production Methods 1 to 5.

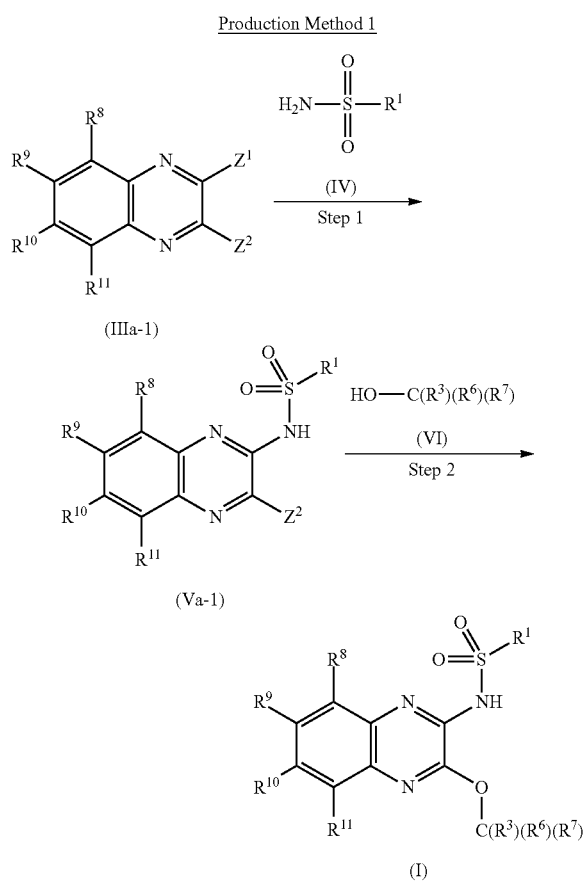

(In the formula, $R^1$, $R^3$, $R^6$, $R^7$, $R^8$, $R^9$, $R^{10}$ and $R^{11}$ have the same meanings as defined above, respectively, and $Z^1$ and $Z^2$ may be the same or different and each represent a leaving group, such as a chlorine atom, a bromine atom, an iodine atom, methanesulfonyloxy, p-toluenesulfonyloxy, and trifluoromethanesulfonyloxy.)

Step 1

Compound (Va-1) can be produced by reacting Compound (IIIa-1) with 1 to 10 equivalents, preferably 1 equivalent, of Compound (IV) in the absence of a solvent or in a solvent inert to the reaction in the presence of 1 to 100 equivalents, preferably 1 to 5 equivalents, of a suitable base at a temperature between −10° C. and 200° C., preferably between 30° C. and 180° C., for 5 minutes to 72 hours.

Examples of the solvent inert to the reaction include tetrahydrofuran (THF), dioxane, 1,2-dimethoxyethane, benzene, toluene, xylene, N, N-dimethyl formamide (DMF), N, N-dimethylacetamide (DMA), dimethyl sulfoxide (DMSO), N-methylpyrrolidone (NMP), pyridine, chloroform, dichloromethane, ethyl acetate, acetonitrile, and the like. These solvents can be used alone or as a mixture thereof. Among these, preferred is DMSO or DMF.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as lithium diisopropylamide (LDA) and lithium hexamethyldisilazane (LiHMDS); alkali metal salts, such as sodium hydroxide, potassium hydroxide, lithium hydroxide, sodium carbonate and potassium carbonate; organic bases, such as pyridine, triethylamine, diisopropylethylamine, 1,8-diazabicyclo[5,4,0]undec-7-ene (DBU), 1,5-diazabicyclo[4,3,0]non-5-ene (DBN), N,N-dimethylaminopyridine (DMAP) and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides, alkali metal salts, and the like. More preferred are sodium hydride, potassium carbonate, and the like.

Compound (IIIa-1) can be obtained, for example, as a commercial product, or according to known methods (for example, the method described in WO 2003/059893, Journal of Medicinal Chemistry, vol. 24, pp. 93-101 (1981), and the like).

Compound (IV) can be obtained, for example, as a commercial product.

Step 2

Compound (I) can be produced by reacting Compound (Va-1) with 1 to 20 equivalents, preferably 1 to 4 equivalents, of Compound (VI) in the absence of a solvent or in a solvent inert to the reaction in the presence of 1 to 100 equivalents, preferably 1 to 10 equivalents, of a suitable base at a temperature between −20° C. and 200° C., preferably between room temperature and 80° C., for 5 minutes to 72 hours.

Examples of the solvent inert to the reaction include THF, dioxane, 1,2-dimethoxyethane, benzene, toluene, xylene, DMF, DMA, NMP, pyridine, chloroform, dichloromethane, ethyl acetate, acetonitrile, and the like. These solvents can be used alone or as a mixture thereof. Among these, preferred is THF or DMF.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides, metal alkoxides, and the like. More preferred are sodium hydride, potassium tert-butoxide, and the like.

Compound (VI) can be obtained according to known methods (For example, Journal of the American Chemical Society, vol. 111, p. 393 (1989), and the like), or as a commercial product.

Production Method 2

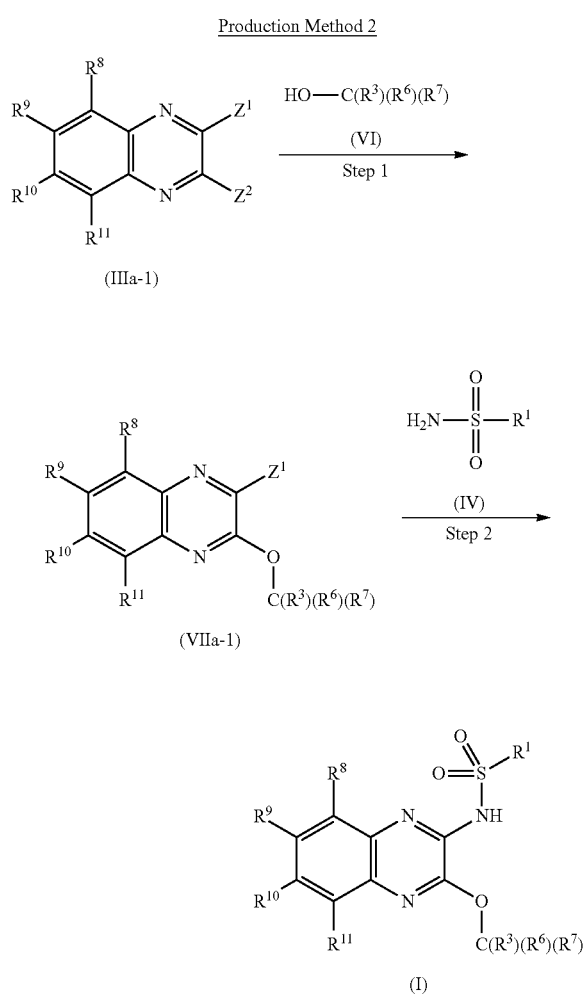

(In the formula, $R^1$, $R^3$, $R^6$, $R^7$, $R^8$, $R^9$, $R^{10}$, $R^{11}$, $Z^1$ and $Z^2$ have the same meanings as defined above, respectively.)

Step 1

Compound (VIIa-1) can be produced from Compound (IIIa-1) in the same manner as in Step 2 of Production Method 1.

Step 2

Compound (I) can be produced from Compound (VIIa-1) in the same manner as in Step 1 of Production Method 1.

Production Method 3

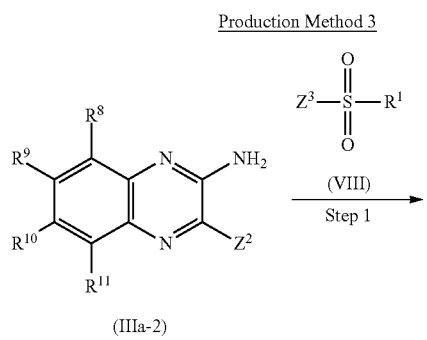

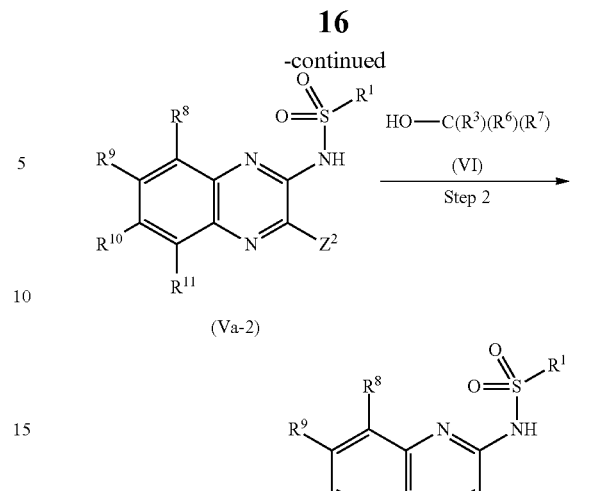

(In the formula, $R^1$, $R^3$, $R^6$, $R^7$, $R^8$, $R^9$, $R^{10}$, $R^{11}$ and $Z^2$ have the same meanings as defined above, respectively, and $Z^3$ represents a leaving group, such as a chlorine atom, a bromine atom, an iodine atom, methanesulfonyloxy, p-toluenesulfonyloxy, or trifluoromethanesulfonyloxy.)

Step 1

Compound (Va-2) can be produced by reacting Compound (IIIa-2) with 1 to 10 equivalents, preferably 1 equivalent, of Compound (VIII) in the absence of a solvent or in a solvent inert to the reaction in the presence of 1 to 100 equivalents, preferably 1 to 5 equivalents, of a suitable base at a temperature between −10° C. and 200° C., preferably between 30° C. and 180° C., for 5 minutes to 72 hours.

Examples of the solvent inert to the reaction include THF, dioxane, 1, 2-dimethoxyethane, benzene, toluene, xylene, DMF, DMA, DMSO, NMP, pyridine, chloroform, dichloromethane, ethyl acetate, acetonitrile, and the like. These solvents can be used alone or as a mixture thereof. Among these, preferred are DMSO, DMF, and the like.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides. More preferred is sodium hydride, or the like.

Compound (IIIa-2) can be obtained, for example, as a commercial product, or according to known methods (for example, the method described in U.S. Pat. No. 3,898,216, WO 2010124826, or the like).

Compound (VIII) can be obtained, for example, as a commercial product.

Step 2

Compound (I) can be produced by reacting Compound (Va-2) with 1 to 20 equivalents, preferably 1 to 4 equivalents, of Compound (VI) in the absence of a solvent or in a solvent inert to the reaction in the presence of 1 to 100 equivalents, preferably 1 to 10 equivalents, of a suitable base at a temperature between −20° C. and 200° C., preferably between room temperature and 80° C., for 5 minutes to 72 hours.

Examples of the solvent inert to the reaction include THF, dioxane, 1,2-dimethoxyethane, benzene, toluene, xylene, DMF, DMA, NMP, pyridine, chloroform, dichloromethane, ethyl acetate, acetonitrile, and the like. These solvents can be used alone or as a mixture thereof. Among these, preferred are THF, DMF, and the like.

Examples of the suitable base include alkali metal hydrides, such as sodium hydride and potassium hydride; metal alkoxides, such as sodium methoxide, sodium ethoxide and potassium tert-butoxide; organometallic bases, such as n-butyllithium, sec-butyllithium and tert-butyllithium; metal amides, such as LDA and LiHMDS; alkali metal salts, such as sodium hydroxide, potassium hydroxide, lithium hydroxide, sodium carbonate and potassium carbonate; organic bases, such as pyridine, triethylamine, diisopropylethylamine, DBU, DBN, DMAP and N-methylmorpholine; solid bases, such as AMBERLYST A-21 (Rohm and Haas Company), AG1-X8 (Bio-Rad Laboratories, Inc.), polyvinylpyridine and morpholinomethyl polystyrene; and the like. Among these, preferred are alkali metal hydrides, metal alkoxides, and the like. More preferred are sodium hydride, potassium tert-butoxide, and the like.

Production Method 4

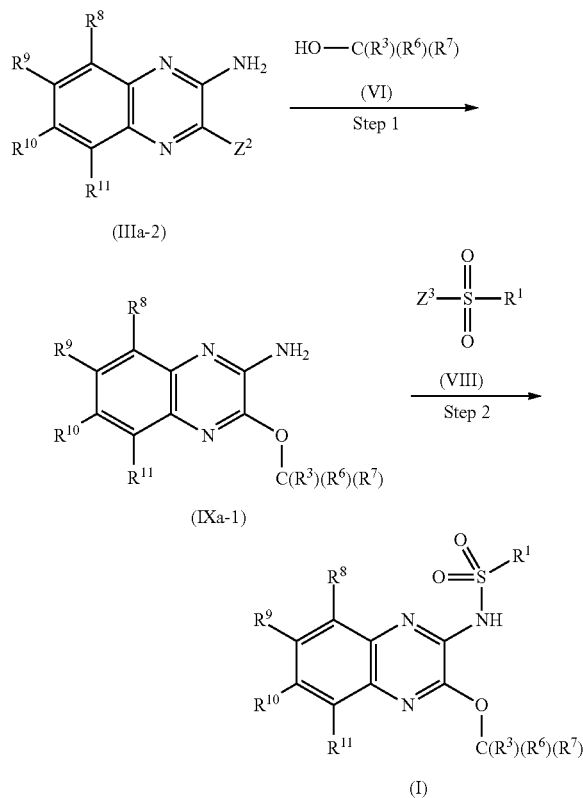

(In the formula, $R^1$, $R^3$, $R^6$, $R^7$, $R^8$, $R^9$, $R^{11}$, $Z^2$ and $Z^3$ have the same meanings as defined above, respectively.)

Step 1

Compound (IXa-1) can be produced from Compound (IIIa-2) in the same manner as in Step 2 of Production Method 3.

Step 2

Compound (I) can be produced from Compound (IXa-1) in the same manner as in Step 1 of Production Method 3.

Production Method 5

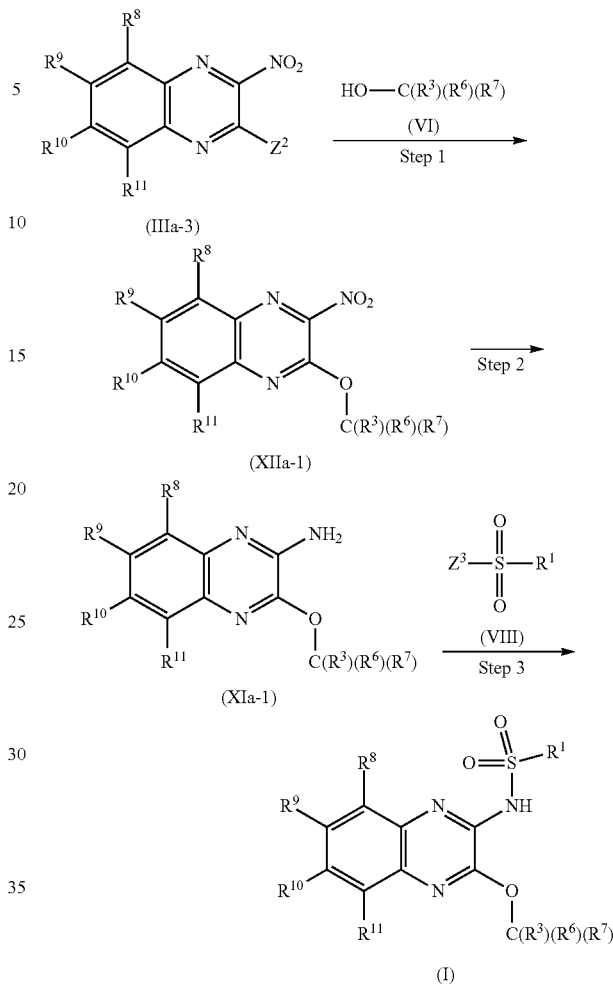

(In the formula, $R^1$, $R^3$, $R^6$, $R^7$, $R^8$, $R^9$, $R^{10}$, $R^{11}$, $Z^2$ and $Z^3$ have the same meanings as defined above, respectively.)

Step 1

Compound (XIIa-1) can be produced from Compound (IIIa-3) in the same manner as in Step 2 of Production Method 3.

Step 2

Compound (XIa-1) can be produced by treating Compound (XIIa-1) with 10 to 100% by weight of a reducing agent in the absence of a solvent or in a solvent inert to the reaction at a temperature between −20° C. and 200° C., preferably between room temperature and 80° C., for 5 minutes to 72 hours.

Examples of the solvent inert to the reaction include water, acetic acid, hydrochloric acid, trifluoroacetic acid, trifluoromethanesulfonic acid, methanol, ethanol, propanol, THF, dioxane, ether, 1,2-dimethoxyethane, benzene, toluene, xylene, DMF, DMA, NMP, pyridine, and the like. These solvents can be used alone or as a mixture thereof. Among these, preferred is water, acetic acid, or a combination thereof.

Examples of the reducing agent include iron(0), tin(0), tin(II) dichloride, tin(II) dichloride dihydrate, zinc, sodium hydrosulfite, and the like. Among these, preferred is iron (0), or the like.

Step 3

Compound (I) can be produced from Compound (XIa-1) in the same manner as in Step 1 of Production Method 3.

Production Method 6

Among Compounds (I), an enantiomer of Compound (I) having asymmetry in —C($R^3$) ($R^6$) ($R^7$) can be obtained by subjecting Compound (I) obtained by Production Methods 1 to 5 to chromatography using an optically active column. Alternatively, the enantiomer can be obtained by subjecting Compound (VIIa-1) obtained by Production Method 2, Compound (IXa-1) obtained by Production Method 4, or Compound (XIIa-1) obtained by Production Method 5 to chromatography using an optically active column to produce the corresponding enantiomer, and subjecting the resulting enantiomer to the next step of each Production Method.

Further alternatively, the enantiomer can be obtained by using an enantiomer of Compound (VI) in Production Methods 1 to 5. The enantiomer of Compound (VI) can be obtained as a commercial product, or according to known methods (for example, WO 98/42643 and the like).

Isolation and purification of the products in the above respective Production Methods can be performed by an appropriate combination of methods generally employed in organic synthesis, for example, filtration, extraction, washing, drying, concentration, crystallization, various types of chromatography, and the like. The intermediates can be subjected to the subsequent reaction without any particular purification.

Some of Compounds (I) exist as isomers such as stereoisomers, regioisomers, geometric isomers, optical isomers (enantiomers), and the like. All possible isomers and mixtures containing the isomers at any ratio are also included and used in the present invention.

A salt of Compound (I) can be obtained as follows. When Compound (I) is obtained in the form of a salt, the salt may be directly purified. When Compound (I) is obtained in a free form, the compound may be dissolved or suspended in a suitable solvent, and then an acid, a base, or the like may be added thereto for salt formation.

Compound (I) or a pharmaceutically acceptable salt thereof may exist in the form of adducts with water or any of various solvents in some cases, and these adducts are also included and used in the present invention.

Specific examples of the compounds used in the present invention are shown in Table 1. However, the scope of the present invention is not limited to these compounds. The compounds shown in Table 1 below are the ones produced in the respective Examples described later.

In the following Table, Me and Pr represent methyl and propyl, respectively.

TABLE 1

| Example No. | Compound No. | $R^1$ | O—C($R^3$)($R^6$)($R^7$) |
|---|---|---|---|
| 1 | 1 | Me (propyl) | Me, OH, Me (on pyridine) |
| 2 | 2 | Me (propyl) | Me, OH, Me (on pyridine N-oxide) |
| 3 | 3 | Me (propyl) | Me, Me, Me (on pyridine) |
| 4 | 4 | Me (propyl) | Me, Me, Me (on pyridine N-oxide) |
| 5 | 5 | Me (propyl) | cyclopropyl (on pyridine) |
| 6 | 6 | Me (propyl) | cyclopropyl (on pyridine N-oxide) |
| 7 | 7 | Me (propyl) | Me, F, Me (on pyridine) |
| 8 | 8 | Me (propyl) | Me, F, Me (on pyridine N-oxide) |
| 9 | 9 | Me (propyl) | O—Me (on pyridine) |

TABLE 1-continued
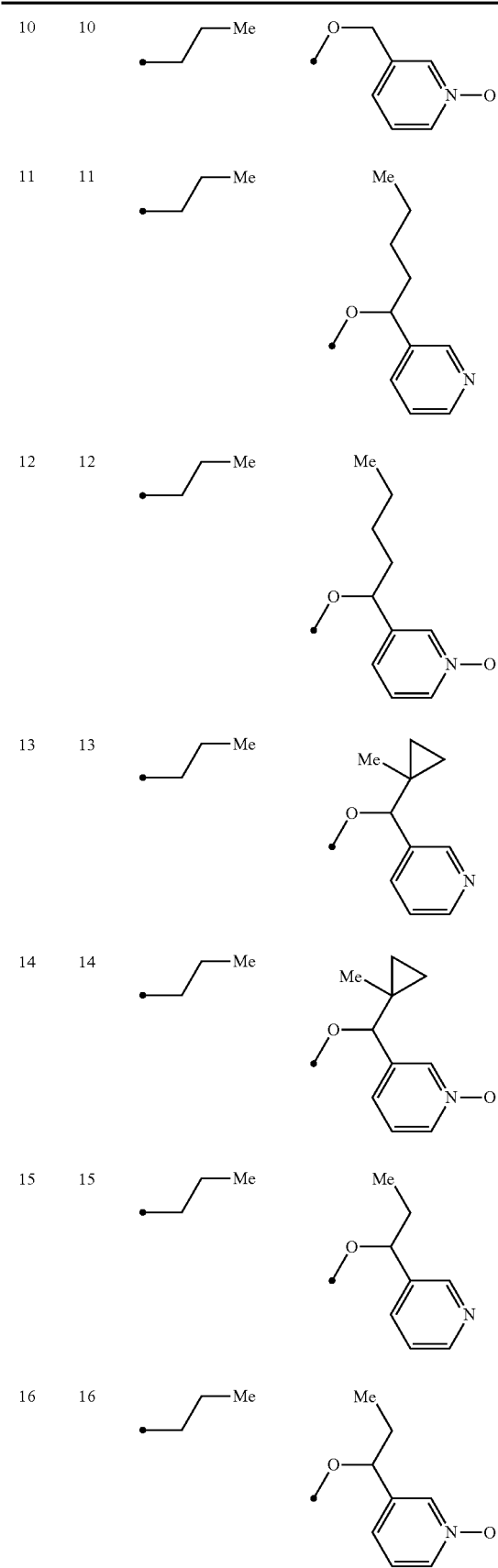
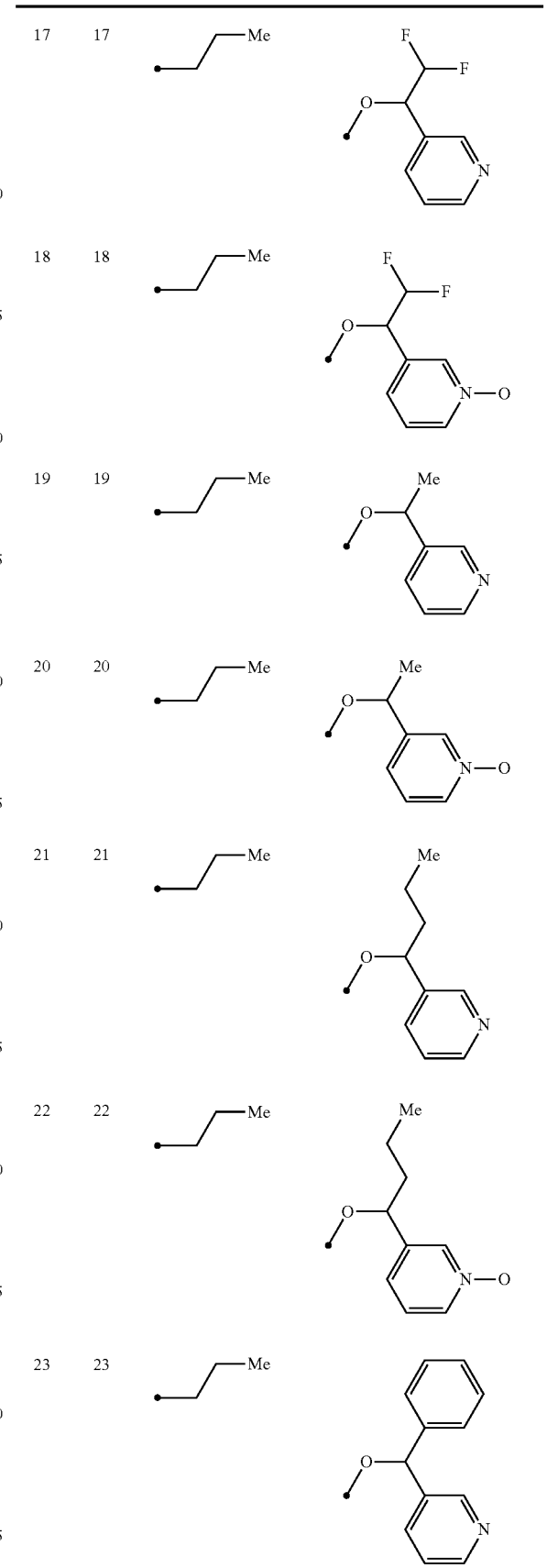

TABLE 1-continued
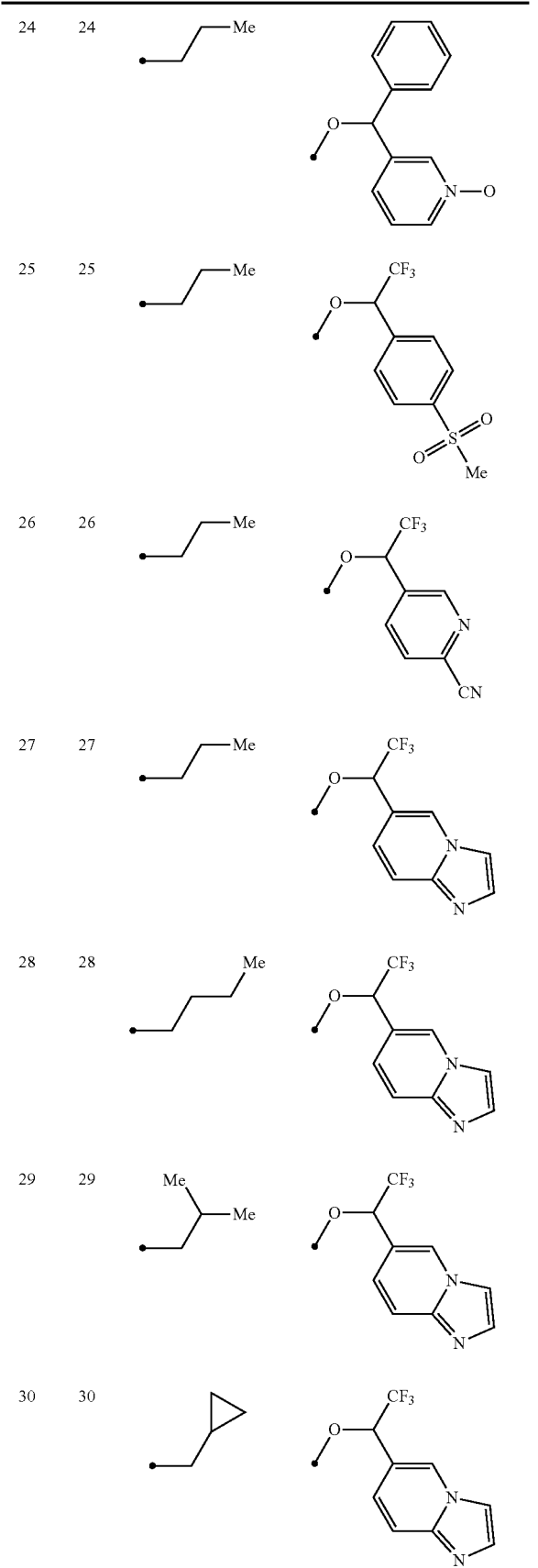
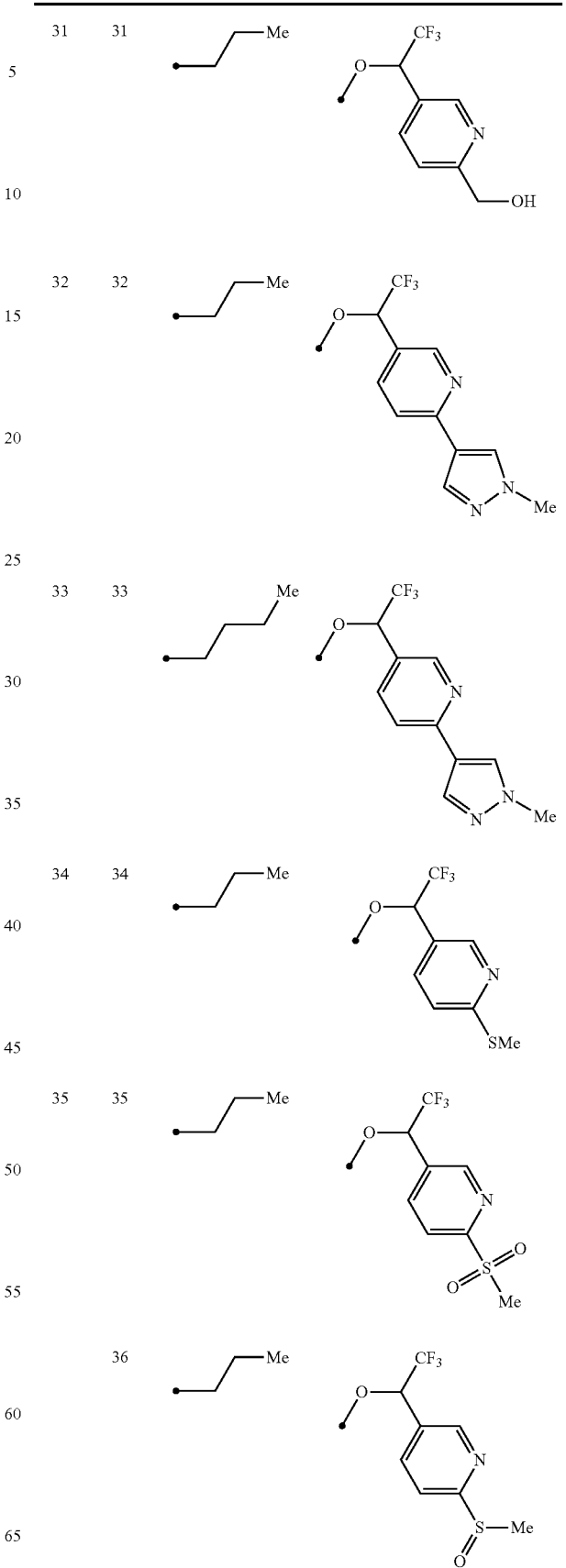

TABLE 1-continued
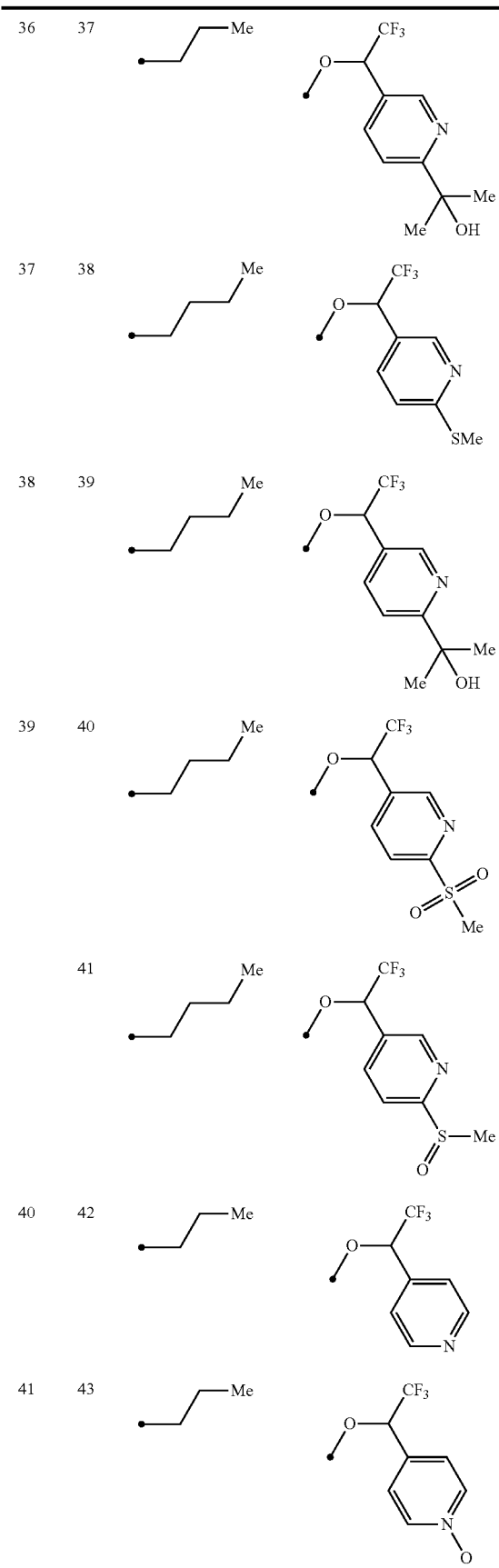
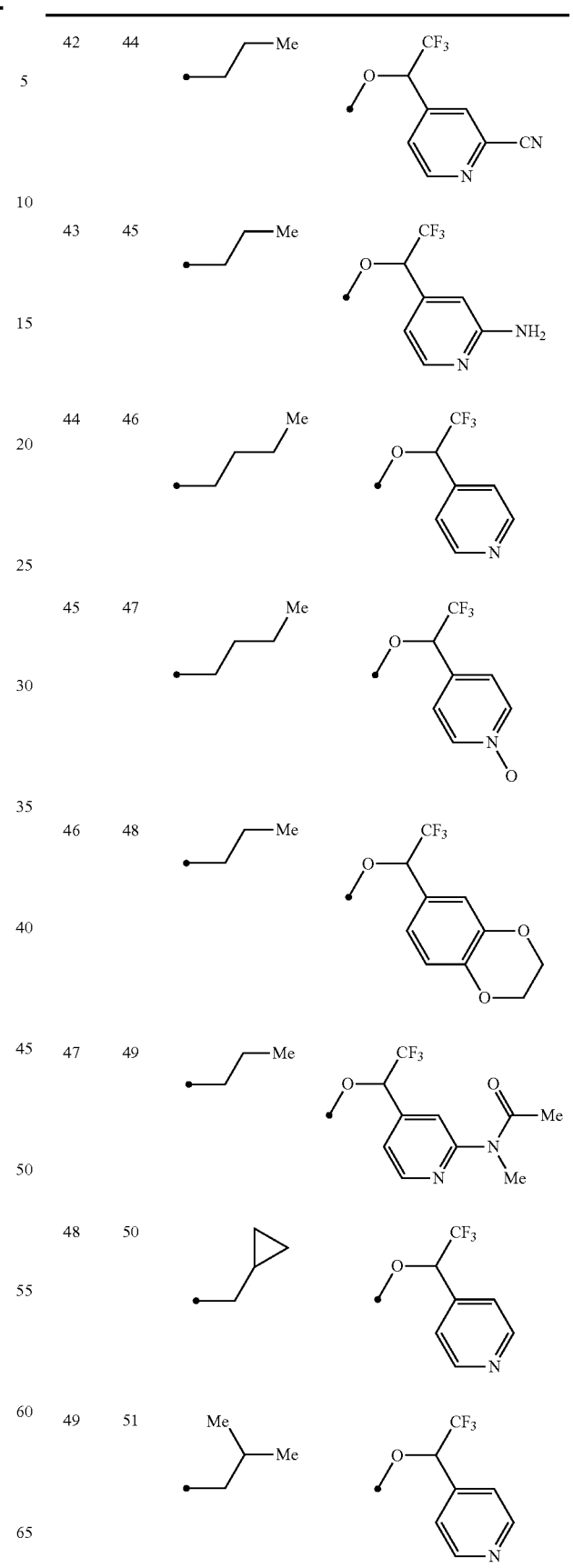

TABLE 1-continued
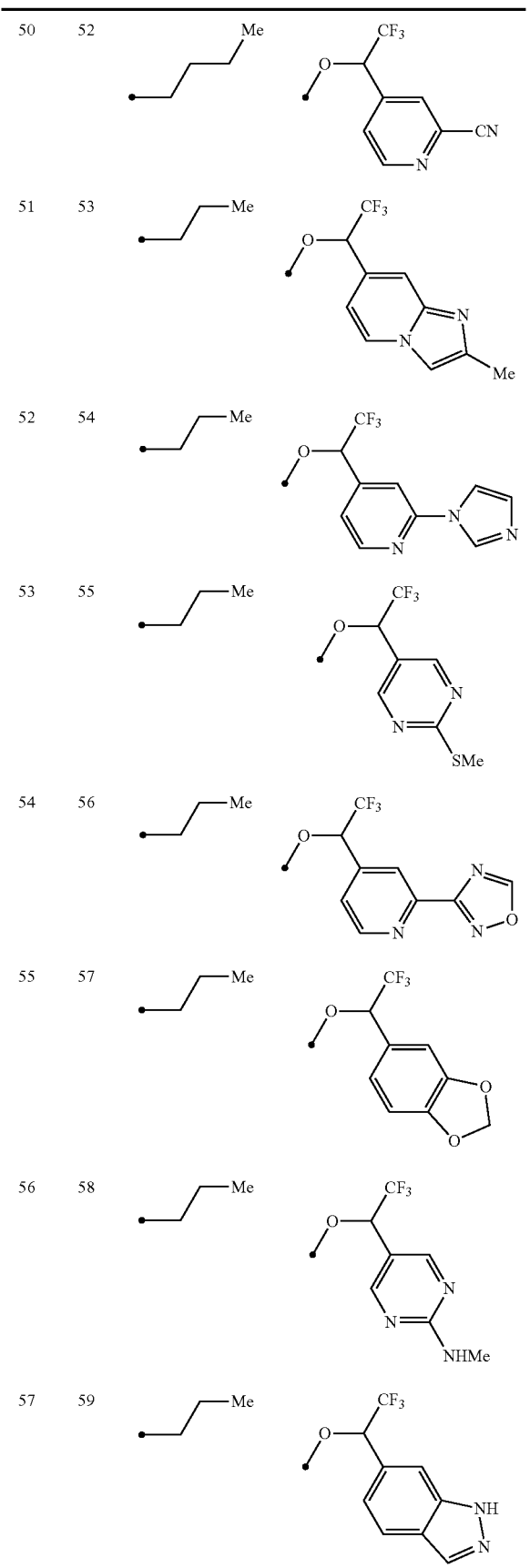
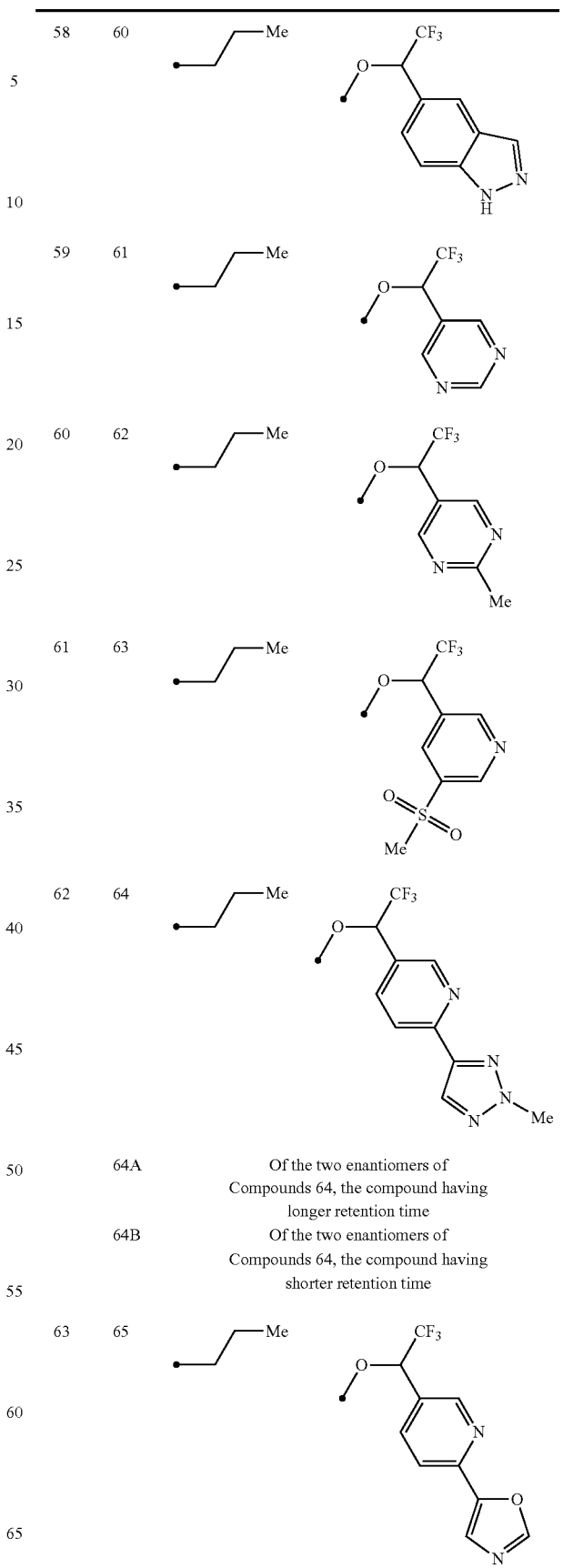
| 64A | Of the two enantiomers of Compounds 64, the compound having longer retention time |
| 64B | Of the two enantiomers of Compounds 64, the compound having shorter retention time |

TABLE 1-continued

| | | | |
|---|---|---|---|
| 64 | 66 | 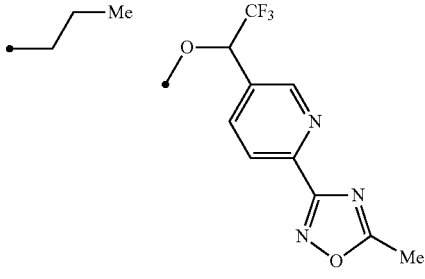 | |
| 65 | 67 | 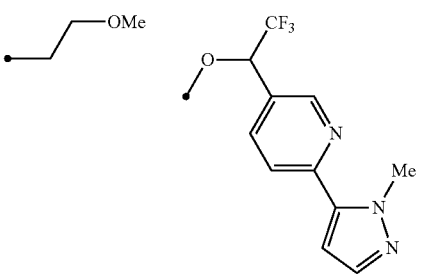 | |
| 66 | 68 | 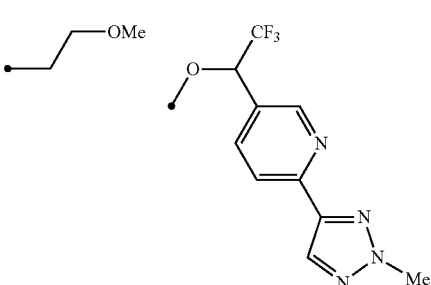 | |
| | 68A | Of the two enantiomers of Compounds 68, the compound having a retention time of 16 minutes | |
| | 68B | Of the two enantiomers of Compounds 68, the compound having a retention time of 30 minutes | |
| 67 | 69 | 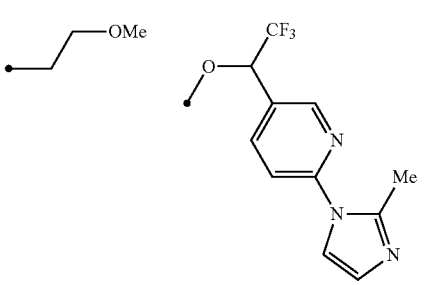 | |
| 68 | 70 | 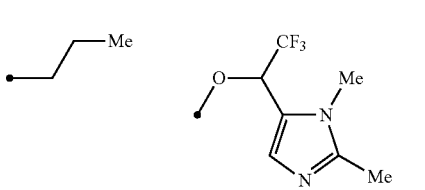 | |
| 69 | 71 | 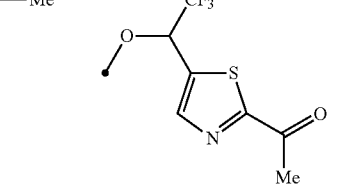 | |
| 70 | 72 | 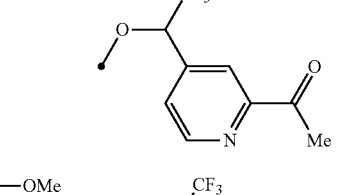 | |
| 71 | 73 | 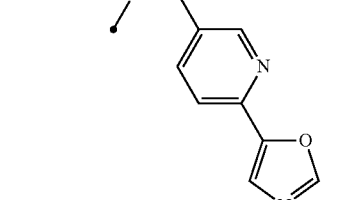 | |
| 72 | 74 | 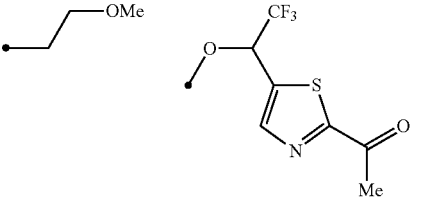 | |
| 73 | 75 | Of the two enantiomers of Compounds 32, the compound having shorter retention time | |
| | 76 | Of the two enantiomers of Compounds 32, the compound having longer retention time | |

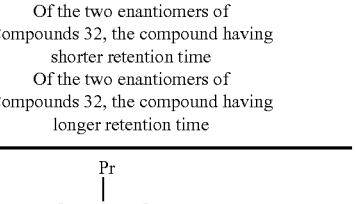

| Example No. | Compound No. | $R^9$ |
|---|---|---|
| 74 | 77 | I |
| 75 | 78 | 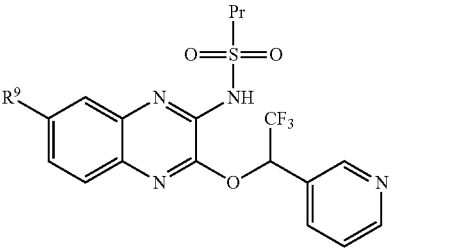 |
| 76 | 79 | 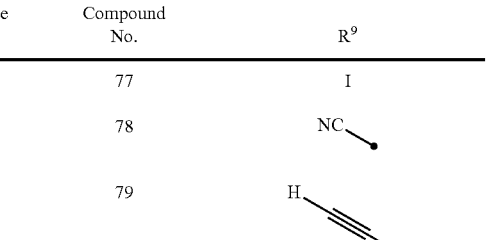 |

Next, pharmacological effects of Compound (I) will be described with reference to Test Examples.

TEST EXAMPLE 1

Inhibitory Activity on the Production of Kynurenine

This assay was performed by a modification of the method described in J. Biol. Chem., vol. 263, pp. 2041-2048 (1988). For culture of the human gastric cancer cell line KATO-III, RPMI 1640 (GIBCO, 11875) supplemented with 10 volt FBS (GIBCO, 10091-148, lot. 665285) was used. One µL of a test substance in a DMSO solution was diluted with 199 µL of the culture medium and placed in wells of a 384-well plate (10 µL/well). Next, IFN-γ (Sigma, 1-3265) was added to the culture medium to a concentration of 31.25 ng/mL, and KATO-III cells were suspended at 50,000 cells/mL in the culture medium. Forty µL of the suspension was added to each well (2,000 cells/well) and incubated under a 5% $CO_2$ atmosphere at 37° C. for 96 hours. The final concentration of DMSO was limited to 0.1 volt or less so that DMSO itself may not affect the kynurenine concentration measured by this assay. After the incubation, 10 µL of a 30 w/vt aqueous trichloroacetic acid solution was added to each well, and incubation was performed at 65° C. for 30 minutes. The plate was centrifuged at 2,500×g for 5 minutes and 15µL of the supernatant in each well was transferred into another 384-well plate. To the transferred supernatant, 15 µL of a 2 w/vt solution of p-dimethylaminobenzaldehyde in acetic acid was added, incubation was performed at 65° C. for 20 minutes and the absorbance was measured at 480 nm.

$$\text{Inhibition rate } (\%) = \frac{(\text{Control} - \text{Sample})}{(\text{Control} - \text{Blank})} \times 100$$

Sample: the absorbance value of the well to which a DMSO solution containing a test substance was added and in which the cells were treated with IFN-γ.

Blank: the absorbance value of the well to which DMSO not containing a test substance was added and in which the cells were treated with IFN-γ.

Control: the absorbance value of the well to which DMSO not containing a test substance was added and in which the cells were not treated with IFN-γ.

The results showed that, for example, the inhibition rates of Compounds 3, 4, 6 to 8, 11 to 17, 19, 21 to 33, 40 to 55, 64 to 79, 64A, 64B and 68A at a concentration of 10 µmol/L were 80% or more.

That is, the results revealed that Compounds (I) of the present invention have an inhibitory activity on the production of kynurenine.

In this assay, expression of IDO in KATO-III cells is induced by IFN-γ treatment and kynurenine in the culture medium is quantified. The kynurenine concentration in a culture medium is known to increase in proportion to the enzymatic activity of intracellular IDO (for example, J. Biol. Chem., vol. 263, pp. 2041-2048 (1988)). The compounds of the present invention showed an inhibitory effect on the production of kynurenine. The production of kynurenine is known to be inhibited by IDO inhibitors (for example, J. Clin. Invest., vol. 117, No. 5, pp. 1147-1154 (1988)), and thus it is speculated that Compounds (I) also have an inhibitory effect on IDO.

Compounds having an inhibitory effect on the production of kynurenine and/or on IDO are known to be useful as an antitumor agent, an anti-AIDS agent, an anti-AIDS dementia agent, an anti-Alzheimer's disease agent, an antidepressant, or the like (for example, J. Clin. Invest., vol. 117, pp. 1147-1154 (2007); J. Virol., vol. 81, pp. 11593-11603 (2007); Neuropathol. Appl. Neurobiol., vol. 31, pp. 395-404 (2005); Neurosci. Lett., vol. 187, pp. 9-12 (1995); and Neuropsychopharmacology, vol. 33, 2341-2351 (2008)). Such compounds are known to also have an immunostimulatory activity (for example, Nat. Immunol., vol. 2, pp. 64-68 (2001)). Therefore Compounds (I) of the present invention are useful as an antitumor agent, an anti-AIDS agent, an anti-AIDS dementia agent, an anti-Alzheimer's disease agent, an antidepressant, an immunostimulator, or the like.

Compound (I) or a pharmaceutically acceptable salt thereof can be used as it is or in various forms of pharmaceuticals depending on its pharmacological effect, the purpose of administration, and the like. A pharmaceutical composition of the present invention can be usually produced by homogeneously mixing an effective amount of Compound (I) or a pharmaceutically acceptable salt thereof as an active ingredient with a pharmaceutically acceptable carrier. The carrier can be in a wide range of forms depending on the dosage form suitable for administration. Preferably, the pharmaceutical composition is in a dosage unit form suitable for oral administration or parenteral administration such as injection, and the like.

For preparation of tablets, for example, excipients such as lactose and mannitol; disintegrants such as starch; lubricants such as magnesium stearate; binders such as polyvinyl alcohol and hydroxypropylcellulose; surfactants such as sucrose fatty acid ester and sorbitol fatty acid ester; and the like can be used in a usual manner. Preferably, 1 to 200 mg of the active ingredient is contained per tablet.

For preparation of injections, water; saline; vegetable oils such as olive oil and peanut oil; solvents such as ethyl oleate and propylene glycol; solubilizing agents such as sodium benzoate, sodium salicylate and urethane; tonicity agents such as salts and glucose; preservatives such as phenol, cresol, p-hydroxybenzoic acid esters and chlorobutanol; antioxidants such as ascorbic acid and sodium pyrosulfite; and the like can be used in a usual manner.

Compound (I) or a pharmaceutically acceptable salt thereof can be administered orally or parenterally (examples: injections, and the like). The effective dose and dose frequency vary depending on the dosage form, the age, body weight and condition of a patient, and the like, but in general, the daily dose is preferably 0.01 to 100 mg/kg.

Subjects to which Compound (I) or a pharmaceutically acceptable salt thereof is administered are preferably patients with the above-described diseases involving the production of kynurenine. Among these, patients with cancers (tumors), neurodegenerative diseases, infections, immune diseases, or the like are suitable, and patients with cancers (tumors) or the like are more suitable. These patients can be selected by a known diagnosis method. For prevention of the onset of these diseases, the above compound can also be administered to mammals which may develop the diseases. Compound (I) or a pharmaceutically acceptable salt thereof or a composition containing said compound or salt thereof can be administered orally or parenterally to humans and non-human mammals (examples: mice, rats, hamsters, guinea pigs, rabbits, cats, dogs, pigs, cows, horses, sheep, monkeys, and the like).

Hereinafter, the present invention will be illustrated in more detail by way of Examples and Reference Examples, but is not limited thereto.

Regarding a proton nuclear magnetic resonance spectrum ($^1$H-NMR), exchangeable hydrogens are not clearly observed in some compounds and on the measurement conditions. The multiplicity of the signals is denoted by notations which are generally employed, and the symbol "br" represents an apparent broad signal.

The instrumental data of the compounds in the respective Reference Examples and Examples below were measured with the following devices.

$^1$H-NMR: JEOL JNM-EX270 (270 MHz) or JEOL JNM-AL300 (300 MHz) MS: JEOL SX-102AQQ (FAB method), JEOL JMS-DX303 (FAB method), Micromass Quattro (APCI method) or Micromass LCT (ESI, APCI method)

Unless otherwise noted, the symbol "%" regarding the concentration means "% by mass", and the ratio of solvents means the volume ratio of the solvents.

Each compound was named using ChemBioDraw ver. 11.0 (Cambridge soft).

REFERENCE EXAMPLE 1

N-(3-chloroquinoxalin-2-yl)propane-1-sulfonamide (Compound A1)

In DMSO were dissolved 2,3-dichloroquinoxaline (5.00 g, 25.1 mmol) and propane-1-sulfonamide (3.09 g, 25.1 mmol). Potassium carbonate (3.47 g, 25.1 mmol) was added and the mixture was stirred at 150° C. for 1 hour. A 1% aqueous acetic acid solution was added to the reaction mixture and the mixture was stirred at room temperature for 3 hours. The resulting solid was separated by filtration, washed with water, and purified by slurrying in diisopropyl ether to give Compound A1 (6.01 g, 84% yield).

REFERENCE EXAMPLE 2

N-(3-chloroquinoxalin-2-yl)butane-1-sulfonamide (Compound A2)

According to Reference Example 1, Compound A2 was obtained from 2,3-dichloroquinoxaline and butane-1-sulfonamide

REFERENCE EXAMPLE 3

N-(3-chloroquinoxalin-2-yl)-2-methylpropane-1-sulfonamide (Compound A3)

According to Reference Example 1, Compound A3 was obtained from 2,3-dichloroquinoxaline and 2-methylpropane-1-sulfonamide.

REFERENCE EXAMPLE 4

N-(3-chloroquinoxalin-2-yl)-1-cyclopropylmethane-sulfonamide (Compound A4)

According to Reference Example 1, Compound A4 was obtained from 2,3-di chloroquinoxaline and 1-cyclopropyl methylsulfonamide.

REFERENCE EXAMPLE 5

N-(3-chloroquinoxalin-2-yl)-N-((2-(trimethylsilyl) ethoxy)methyl)propane-1-sulfonamide (Compound A5)

Compound A1 (1.22 g, 4.28 mmol) obtained in Reference Example 1 was dissolved in dichloromethane (12.0 mL). Diisopropylethylamine (1.5 mL, 8.6 mmol) and 2-(trimethylsilyl)ethoxymethyl chloride (1.10 mL, 6.40 mmol) were added and the mixture was stirred at room temperature for minutes. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=5/1) to give Compound A5 (1.68 g, 94% yield).

REFERENCE EXAMPLE 6

N-(3-chloroquinoxalin-2-yl)-N-((2-(trimethylsilyl) ethoxy)methyl)butane-1-sulfonamide (Compound A6)

According to Reference Example 5, Compound A6 (1.08 g, 75% yield) was obtained from Compound A2 (1.00 g, 3.34 mmol) obtained in Reference Example 2.

REFERENCE EXAMPLE 7

N-(3-chloroquinoxalin-2-yl)-N-((2-(trimethylsilyl) ethoxy)methyl)-2-methylpropane-1-sulfonamide (Compound A7)

According to Reference Example 5, Compound A7 (434 mg, 60%) was obtained from Compound A3 (500 mg, 1.67 mmol) obtained in Reference Example 3.

REFERENCE EXAMPLE 8

N-(3-chloroquinoxalin-2-yl)-1-cyclopropyl-N-((2-(trimethyl silyl)ethoxy)methyl)methanesulfonamide (Compound A8)

According to Reference Example 5, Compound A8 (425 mg, 98%) was obtained from Compound A4 (300 mg, 1.01 mmol) obtained in Reference Example 4.

REFERENCE EXAMPLE 9

2-chloro-3-((1-methylcyclopropyl)(pyridin-3-yl) methoxy) quinoxaline (Compound A9)

Step 1

To toluene (12 mL) were added dropwise at −78° C. n-butyllithium (2.76 mol/L solution in n-hexane, 4.14 mL, 11.4 mmol) and a solution of 3-bromopyridine (1.00 mL, 10.4 mmol) in toluene (4.0 mL), and the mixture was stirred at the same temperature for 30 minutes. THF (4.0 mL) was added to the resulting suspension. After stirring at −78° C. for 15 minutes, methacrolein (1.03 mL, 12.5 mmol) was added, and the mixture was stirred for 1 hour allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=3/7) to give 2-methyl-1-(pyridin-3-yl)prop-2-en-1-ol (1.08 g, 70% yield).

Step 2

In dichloromethane (40.0 mL) was dissolved 2-methyl-1-(pyridin-3-yl)prop-2-en-1-ol (1.04 g, 6.95 mmol) obtained in Step 1. Diethylzinc (1.09 mol/L solution in n-hexane, 31.9 mL, 34.7 mmol) and diiodomethane (2.80 mL, 34.7 mmol) were added dropwise at −10° C. and the mixture was stirred at 0° C. for 2.5 hours. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=3/7) to give (1-methylcyclopropyl)(pyridin-3-yl)methanol (888 mg, 78% yield).
Step 3

In THF (5.0 mL) were dissolved (1-methylcyclopropyl) (pyridin-3-yl)methanol (130 mg, 0.796 mmol) obtained in Step 2 and 2,3-dichloroquinoxaline (190 mg, 0.956 mmol). To the mixture was added 60% sodium hydride (in oil, 38.2 mg, 0.956 mmol) and the mixture was stirred at 50° C. for 1.5 hours. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=17/3) to give Compound A9 (147 mg, 57% yield).

REFERENCE EXAMPLE 10

2-chloro-3-(2,2,2-trifluoro-1-(4-(methylsulfonyl) phenyl)ethoxy)quinoxaline (Compound A10)

Step 1

In THF (10.0 mL) was dissolved 4-(methylsulfonyl)benzaldehyde (500 mg, 2.71 mmol). To the solution were added (trifluoromethyl)trimethylsilane (0.602 mL, 4.07 mmol) and tetrabutylammonium fluoride (1.0 mol/L solution in THF, 0.136 mL, 0.136 mmol), and the mixture was stirred at room temperature for 1 hour. To the mixture was added 1 mol/L hydrochloric acid and the mixture was stirred at room temperature for 5 minutes. A saturated aqueous sodium bicarbonate solution was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=1/1) to give 2,2,2-trifluoro-1-(4-(methylsulfonyl)phenyl)ethanol (454 mg, 66% yield).
Step 2

According to Step 3 of Reference Example 9, Compound A10 (244 mg, 32% yield) was obtained from 2,2,2-trifluoro-1-(4-(methylsulfonyl)phenyl)ethanol (454 mg, 1.78 mmol) obtained in Step 1.

REFERENCE EXAMPLE 11

5-(1-(3-chloroquinoxalin-2-yloxy)-2,2,2-trifluoroethyl) picolinonitrile (Compound A11)

Step 1

In toluene (100 mL) were suspended 6-bromo-3-pyridinecarboxyaldehyde (1.03 g, 5.54 mmol), ethylene glycol (370 μL, 6.65 mmol) and Amberlyst 15 (200 mg). The suspension was refluxed under a nitrogen atmosphere for 12 hours, during which produced water was removed with a Dean-Stark trap. After filtration of the reaction mixture, the filtrate was concentrated. The residue was purified by silica gel column chromatography (hexane/ethyl acetate=7/3) to give 2-bromo-5-(1,3-dioxolan-2-yl)pyridine (895 mg, 70% yield).
Step 2

In DMF (30 mL) were dissolved 2-bromo-5-(1,3-dioxolan-2-yl)pyridine (895 mg, 3.89 mmol) obtained in Step 1, zinc cyanide (1.14 g, 5.83 mmol) and tetrakis(triphenylphosphine)palladium (899 mg, 0.778 mmol) and the mixture was stirred under a nitrogen atmosphere at 80° C. for 12 hours. The reaction mixture was concentrated and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=7/3) to give 5-(1,3-dioxolan-2-yl)picolinonitrile (506 mg, 740 yield).
Step 3

In THF (5.0 mL) was dissolved 5-(1,3-dioxolan-2-yl)picolinonitrile (478 mg, 2.71 mmol) obtained in Step 2, and 1 mol/L hydrochloric acid (5.0 mL) was added under a nitrogen atmosphere at room temperature. The mixture was stirred at the same temperature for 16 hours and further stirred at 50° C. for 13 hours. The reaction mixture was neutralized with a saturated aqueous sodium bicarbonate solution. Extraction with ethyl acetate, washing with saturated brine and drying over anhydrous sodium sulfate were performed. After filtration, the solvent in the filtrate was evaporated under reduced pressure to give 5-formylpicolinonitrile (364 mg, 100% yield).
Step 4

According to Step 1 of Reference Example 10, 5-(2,2,2-trifluoro-1-hydroxyethyl)picolinonitrile (455 mg, 82% yield) was obtained from 5-formylpicolinonitrile (364 mg, 2.76 mmol) obtained in Step 3.
Step 5

According to Step 3 of Reference Example 9, Compound A11 (292 mg, 38% yield) was obtained from 5-(2,2,2-trifluoro-1-hydroxyethyl)picolinonitrile (424 mg, 2.10 mmol) obtained in Step 3.

REFERENCE EXAMPLE 12

2-(5-(1-(3-chloroquinoxalin-2-yloxy)-2,2,2-trifluoroethyl)pyridin-2-yl)propan-2-ol (Compound A12)

Step 1

According to Step 1 of Reference Example 10, 1-(6-bromopyridin-3-yl)-2,2,2-trifluoroethanol (3.69 g, 90% yield) was obtained from 6-bromonicotinaldehyde (3.00 g, 16.1 mmol).
Step 2

In n-propanol (3.0 mL) and DMF (3.0 mL) was dissolved 1-(6-bromopyridin-3-yl)-2,2,2-trifluoroethanol (300 mg, 1.17 mmol) obtained in Step 1. To the solution were added [1,1'-bis(diphenylphosphino)ferrocene]palladium (II) chloride-dichloromethane complex (85.6 mg, 0.117 mmol), 1,1'-bis(diphenylphosphino)ferrocene (130 mg, 0.234 mmol) and triethylamine (1.63 mL, 11.7 mL). The mixture was stirred under a carbon monoxide atmosphere at 80° C. for 18 hours. The solvent was evaporated under reduced pressure and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=1/1) and further purified by preparative thin-layer chromatography (hexane/ethyl acetate=1/1) to give propyl 5-(2,2,2-trifluoro-1-hydroxyethyl)picolinate (284 mg, 92% yield).

Step 3

In THF (5.0 mL) was dissolved propyl 5-(2,2,2-trifluoro-1-hydroxyethyl)picolinate (284 mg, 1.08 mmol) obtained in Step 2. Methylmagnesium bromide (0.93 mol/L solution in THF, 5.80 mL, 5.39 mmol) was added dropwise at −78° C., and the mixture was stirred for 1 hour allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=1/1) to give 2-(5-(2,2,2-trifluoro-1-hydroxyethyl)pyridin-2-yl)propan-2-ol (222 mg, 87% yield).

Step 4

According to Step 3 of Reference Example 9, Compound A12 (179 mg, 73% yield) was obtained from 2-(5-(2,2,2-trifluoro-1-hydroxyethyl)pyridin-2-yl)propan-2-ol (162 mg, 0.615 mmol) obtained in Step 3.

REFERENCE EXAMPLE 13

2-chloro-3-(2,2,2-trifluoro-1-(5-(methylsulfonyl)pyridin-3-yl)ethoxy)quinoxaline (Compound A13)

Step 1

In diethyl ether (42.0 mL) was dissolved 3,5-dibromopyridine (1.00 g, 4.22 mmol). n-Butyllithium (2.76 mol/L solution in n-hexane, 1.61 mL, 4.43 mmol) was added dropwise at −78° C., and the mixture was stirred at the same temperature for 30 minutes. Further, DMF (0.98 mL, 12.7 mmol) was added and the mixture was stirred for 3 hours allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=7/3) to give 5-bromonicotinaldehyde (314 mg, 40%).

Step 2

According to Step 1 of Reference Example 10, 1-(5-bromopyridin-3-yl)-2,2,2-trifluoroethanol (390 mg, 90% yield) was obtained from 5-bromonicotinaldehyde (314 mg, 1.69 mmol) obtained in Step 1.

Step 3

In pyridine (2.0 mL) was dissolved 1-(5-bromopyridin-3-yl)-2,2,2-trifluoroethanol (390 mg, 1.52 mmol) obtained in Step 2. Acetic anhydride (2.0 mL) was added and the mixture was stirred at room temperature for 18 hours. The solvent was evaporated under reduced pressure and a saturated aqueous sodium bicarbonate solution and water were added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=1/1) and further purified by preparative thin-layer chromatography (hexane/ethyl acetate=4/1) to give 1-(5-bromopyridin-3-yl)-2,2,2-trifluoroethyl acetate (429 mg, 95% yield).

Step 4

In DMSO (3.0 mL) was dissolved 1-(5-bromopyridin-3-yl)-2,2,2-trifluoroethyl acetate (429 mg, 1.44 mmol) obtained in Step 3. To the solution were added sodium methanesulfinate (176 mg, 1.73 mmol), copper iodide (I) (41.1 mg, 0.216 mmol), L-proline (49.7 mg, 0.432 mmol) and sodium bicarbonate (36.3 mg, 0.432 mg) and the mixture was stirred at 95° C. for 72 hours. Water was added to the reaction mixture. Extraction with ethyl acetate, washing with saturated brine and drying over anhydrous sodium sulfate were performed. After filtration, the solvent in the filtrate was evaporated under reduced pressure and the residue was dissolved in methanol (10.0 mL). Potassium carbonate (597 mg, 4.32 mmol) was added and the mixture was stirred at room temperature for 1 hour. The solvent was evaporated under reduced pressure and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=3/7) to give 2,2,2-trifluoro-1-(5-(methylsulfonyl)pyridin-3-yl)ethanol (61.4 mg, 17% yield).

Step 5

According to Step 3 of Reference Example 9, Compound A13 (69.1 mg, 69% yield) was obtained from 2,2,2-trifluoro-1-(5-(methylsulfonyl)pyridin-3-yl)ethanol (61.4 mg, 0.241 mmol) obtained in Step 4.

REFERENCE EXAMPLE 14

2-methyl-1-(pyridin-3-yl)propane-1,2-diol (Compound A14)

Step 1

Nicotinaldehyde (1.00 mL, 9.66 mmol) was dissolved in dichloromethane (20 mL). To the solution were added trimethylsilyl cyanide (0.129 mL, 9.66 mmol) and triphenylmethylphosphonium iodide (437 mg, 9.66 mmol) and the mixture was stirred at room temperature for 18 hours. Water was added to the reaction mixture. Extraction with dichloromethane and drying over anhydrous sodium sulfate were performed. After filtration, the solvent in the filtrate was evaporated under reduced pressure. The residue was purified by silica gel column chromatography (hexane/ethyl acetate=7/3) to give 2-(pyridin-3-yl)-2-(trimethylsilyloxy)acetonitrile (650 mg, 33%).

Step 2

A 10% hydrogen chloride/methanol solution (6 . 5 mL) was added to 2-(pyridin-3-yl)-2-(trimethylsilyloxy)acetonitrile (650 mg, 3.15 mmol) obtained in Step 1 and the mixture was stirred at room temperature for 4 hours. The solvent was evaporated under reduced pressure and a saturated aqueous sodium bicarbonate solution was added. Extraction with ethyl acetate, washing with saturated brine and drying over anhydrous sodium sulfate were performed. After filtration, the solvent in the filtrate was evaporated under reduced pressure. The residue was purified by silica gel column chromatography (ethyl acetate: 100%) to give methyl 2-hydroxy-2-(pyridin-3-yl)acetate (415 mg, 79% yield).

Step 3

Methyl 2-hydroxy-2-(pyridin-3-yl)acetate (415 mg, 2.48 mmol) obtained in Step 2 was dissolved in THF (3.0 mL). Methylmagnesium bromide (0.87 mol/L solution in THF, 14.3 mL, 12.4 mmol) was added dropwise at 0° C. and the mixture was stirred for 2 hours allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=9/1) to give Compound A14 (206 mg, 50% yield).

REFERENCE EXAMPLE 15

2,2-dimethyl-1-(pyridin-3-yl)propan-1-ol (Compound A15)

According to Step 1 of Reference Example 9, Compound A15 (1.58 mg, 92% yield) was obtained from 3-bromopyridine (1.00 mL, 10.4 mmol) and pivalaldehyde (1.36 mL, 12.5 mmol).

REFERENCE EXAMPLE 16

1-cyclopropyl-1-(pyridin-3-yl)methanol (Compound A16)

According to Step 1 of Reference Example 9, Compound A16 (1.25 mg, 81% yield) was obtained from 3-bromopyridine (1.00 mL, 10.4 mmol) and cyclopropanecarbaldehyde (0.934 mL, 12.5 mmol).

REFERENCE EXAMPLE 17

2-fluoro-2-methyl-1-(pyridin-3-yl)propan-1-ol (Compound A17)

Step 1
According to Step 1 of Reference Example 9, 2-methyl-1-(pyridin-3-yl)propan-1-ol (2.43 g, 52% yield) was obtained from 3-bromopyridine (3.00 mL, 31.1 mmol) and isobutyraldehyde (3.41 mL, 37.3 mmol).
Step 2
In dichloromethane (60.0 mL) was dissolved 2-methyl-1-(pyridin-3-yl)propan-1-ol (2.16 g, 14.3 mmol) obtained in Step 1. Manganese dioxide (107 g) was added and the mixture was stirred at room temperature for 7 hours. After the reaction mixture was filtered through Celite, the solvent in the filtrate was evaporated under reduced pressure. The residue was purified by silica gel column chromatography (hexane/ethyl acetate=1/1) to give 2-methyl-1-(pyridin-3-yl)propan-1-one (1.72 g, 81% yield).
Step 3
A solution of 2-methyl-1-(pyridin-3-yl)propan-1-one (1.72 g, 11.5 mmol) obtained in Step 2 in THF (20 mL) was slowly added dropwise to lithium bis(trimethylsilyl)amide (1.0 mol/L solution in THF, 13.8 mL, 13.8 mmol) at −78° C. and the mixture was stirred at the same temperature for 30 minutes. Further, N-fluorobenzenesulfonimide (4.36 g, 13.8 mmol) was added and the mixture was stirred for 1.5 hours allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give 2-fluoro-2-methyl-1-(pyridin-3-yl)propan-1-one (1.73 g, 89% yield).
Step 4
In methanol (30.0 mL) was dissolved 2-fluoro-2-methyl-1-(pyridin-3-yl)propan-1-one (1.73 g, 10.3 mmol) obtained in Step 3. Sodium borohydride (584 mg, 15.4 mmol) was added and the mixture was stirred at 0° C. for 30 minutes. The solvent was evaporated under reduced pressure and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=1/1) and further purified by preparative thin-layer chromatography (hexane/ethyl acetate=3/7) to give Compound A11 (1.54 g, 89% yield).

REFERENCE EXAMPLE 18

1-(pyridin-3-yl)pentan-1-ol (Compound A18)

Nicotinaldehyde (0.500 mL, 4.83 mmol) was dissolved in THF (7.0 mL). n-Butyllithium (2.76 mol/L solution in n-hexane, 2.63 mL, 7.25 mmol) was added at −78° C. and the mixture was stirred at the same temperature for 10 minutes. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give Compound A18 (597 mg, 75% yield).

REFERENCE EXAMPLE 19

1-(pyridin-3-yl)propan-1-ol (Compound A19)

A solution of nicotinaldehyde (0.200 mL, 0.12 mmol) in THF (2.0 mL) was slowly added to ethylmagnesium bromide (1.0 mol/L solution in THF, 3.18 mL, 3.18 mmol) at 0° C. The mixture was stirred at the same temperature for 1 hour and a saturated aqueous ammonium chloride solution was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (chloroform/methanol=9/1) to give Compound A19 (194 mg, 67% yield).

REFERENCE EXAMPLE 20

2,2-difluoro-1-(pyridin-3-yl)ethanol (Compound A20)

Step 1
To toluene (7.0 mL) were added dropwise at −78° C. n-butyllithium (2.76 mol/L solution in n-hexane, 2.60 mL, 7.19 mmol) and a solution of 3-bromopyridine (1.00 mL, 10.4 mmol) in toluene (2.5 mL), and the mixture was stirred at the same temperature for 30 minutes. THF (4.0 mL) was added to the resulting suspension and the mixture was stirred at −78° C. for 15 minutes. To the mixture was added 2,2-difluoro-N-methoxy-N-methylacetamide (1.00 g, 7.19 mmol) and the mixture was stirred for 3 hours allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=3/7) to give 2,2-difluoro-1-(pyridin-3-yl)ethanone (868 mg, 91% yield).
Step 2

According to Step 4 of Reference Example 17, Compound A20 (724 mg, 83% yield) was obtained from 2,2-difluoro-1-(pyridin-3-yl)ethanone (864 mg, 5.50 mmol) obtained in Step 1.

REFERENCE EXAMPLE 21

1-(pyridin-3-yl)ethanol (Compound A21)

According to Step 4 of Reference Example 17, Compound A21 (724 mg, 83% yield) was obtained from 1-(pyridin-3-yl)ethanone (0.500 mL, 4.56 mmol).

REFERENCE EXAMPLE 22

1-(pyridin-3-yl)butan-1-ol (Compound A22)

According to Step 1 of Reference Example 9, Compound A22 (403 mg, 27% yield) was obtained from 3-bromopyridine (1.00 mL, 10.4 mmol) and n-butyraldehyde (1.13 mL, 12.5 mmol).

REFERENCE EXAMPLE 23

Phenyl(pyridin-3-yl)methanol (Compound A23)

According to Step 4 of Reference Example 17, Compound A23 (425 mg, 84% yield) was obtained from phenyl(pyridin-3-yl)methanone (0.500 mL, 2.73 mmol).

REFERENCE EXAMPLE 24

2,2,2-trifluoro-1-(imidazo[1,2-a]pyridin-6-yl)ethanol (Compound A24)

According to Step 1 of Reference Example 10, Compound A24 (224 mg, 59% yield) was obtained from imidazo[1,2-a]pyridine-6-carbaldehyde (258 mg, 1.77 mmol).

REFERENCE EXAMPLE 25

2,2,2-trifluoro-1-(6-methylpyridin-3-yl)ethanol (Compound A25)

According to Step 1 of Reference Example 10, Compound A25 (2.25 g, 83% yield) was obtained from 6-methylnicotinaldehyde (1.72 g, 14.2 mmol).

REFERENCE EXAMPLE 26

2,2,2-trifluoro-1-(6-(1-methyl-1H-pyrazol-4-yl)pyridin-3-yl)ethanol (Compound A26)

In 1,4-dioxane (2.0 mL) was dissolved 1-(6-bromopyridin-3-yl)-2,2,2-trifluoroethanol (98.6 mg, 0.385 mmol). To the solution were added 1-methyl-4-(4,4,5,5-tetramethyl-1,3,2-dioxaborolan-2-yl)-1H-pyrazole (120 mg, 0.578 mmol), cesium carbonate (188 mg, 0.578 mmol), tris(dibenzylideneacetone)dipalladium (5.3 mg, 0.0058 mmol), tricyclohexylphosphine (3.9 mg, 0.0139 mmol) and water (0.2 mL), and the mixture was stirred at 80° C. for 2 hours. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (chloroform/methanol=19/1) to give Compound A26 (94.5 mg, 950 yield).

REFERENCE EXAMPLE 27

2,2,2-trifluoro-1-(6-(methylthio)pyridin-3-yl)ethanol (Compound A27)

Step 1

In DMF (5.0 mL) was dissolved 6-chloronicotinaldehyde (300 mg, 2.12 mmol). Sodium thiomethoxide (178 mg, 2.54 mmol) was added and the mixture was stirred at room temperature for 2 hours. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give 6-(methylthio)nicotinaldehyde (239 mg, 74%).
Step 2

According to Step 1 of Reference Example 10, Compound A27 (326 mg, 94% yield) was obtained from 6-(methylthio)nicotinaldehyde (238 mg, 1.55 mmol) obtained in Step 1.

REFERENCE EXAMPLE 28

2,2,2-trifluoro-1-(pyridin-4-yl)ethanol (Compound A28)

According to Step 1 of Reference Example 10, Compound A28 (1.68 g, 94%) was obtained from isonicotinaldehyde (1.22 g, 4.28 mmol).

ESIMS m/z: 178 (M+H)$^+$.

REFERENCE EXAMPLE 29

1-(2,3-dihydrobenzo[b][1,4]dioxin-6-yl)-2,2,2-trifluoroethanol (Compound A29)

According to Step 1 of Reference Example 10, Compound A29 (639 mg, 89% yield) was obtained from 2,3-dihydrobenzo[b][1,4]dioxin-6-carbaldehyde (503 mg, 3.06 mmol).

REFERENCE EXAMPLE 30

2,2,2-trifluoro-1-(2-methylimidazo[1,2-a]pyridin-7-yl)ethanol (Compound A30)

Step 1

Compound A28 (1.00 g, 5.65 mmol) obtained in Reference Example 28 was dissolved in acetic anhydride (5.0 mL) and pyridine (5 mL) and the mixture was stirred at room temperature for 1 hour. The solvent was evaporated under reduced pressure. The residue was dissolved in dichloromethane (10.0 mL) and 65% meta-chloroperbenzoic acid (650 mg, 2.82 mmol) was added at 0° C. The mixture was stirred at room temperature for 3 hours and a 20% aqueous sodium thiosulfate solution was added to the reaction mixture. Extraction with chloroform and drying over anhydrous sodium sulfate were performed. After filtration, the solvent in the filtrate was evaporated under reduced pressure. The residue was purified by silica gel column chromatography (chloroform/methanol=10/1) to give 4-(1-acetoxy-2,2,2-trifluoroethyl)pyridine 1-oxide (1.09 g, 82% yield).

Step 2

According to Example 43, 1-(2-aminopyridin-4-yl)-2,2,2-trifluoroethyl acetate (53.2 mg, 27% yield) was obtained from 4-(1-acetoxy-2,2,2-trifluoroethyl)pyridine 1-oxide (197 mg, 0.838 mmol) obtained in Step 1.

Step 3

In n-butanol (2 mL) was dissolved 1-(2-aminopyridin-4-yl)-2,2,2-trifluoroethyl acetate (53.2 mg, 0.227 mmol) obtained in Step 2. Bromoacetone (0.042 mL, 0.45 mmol) was added and the mixture was stirred at 130° C. for 24 hours. A saturated aqueous sodium bicarbonate solution and water were added to the reaction mixture. Extraction with ethyl acetate and drying over anhydrous sodium sulfate were performed. After filtration, the solvent in the filtrate was evaporated under reduced pressure and the residue was dissolved in methanol (2.0 mL). Potassium carbonate (31.4 mg, 0.227 mmol) was added and the mixture was stirred at room temperature for 18 hours. A saturated aqueous ammonium chloride solution was added to the reaction mixture. Extraction with ethyl acetate and drying over anhydrous sodium sulfate were performed. After filtration, the solvent in the filtrate was evaporated under reduced pressure. The residue was purified by silica gel column chromatography (chloroform/methanol=5/1) to give Compound A30 (20.7 mg, 40% yield).

ESIMS m/z: 218 (M+H)$^+$.

REFERENCE EXAMPLE 31

2,2,2-trifluoro-1-(2-(methylthio)pyrimidin-5-yl)ethanol (compound A31)

According to Step 1 of Reference Example 10, Compound A31 (245 mg, 84% yield) was obtained from 2-(methylthio)pyrimidine-5-carbaldehyde (200 mg, 1.30 mmol).

ESIMS m/z: 225 (M+H)$^+$.

REFERENCE EXAMPLE 32

1-(benzo[d][1,3]dioxol-5-yl)-2,2,2-trifluoroethanol (Compound A32)

According to Step 1 of Reference Example 10, Compound A32 (614 mg, 82% yield) was obtained from benzo[d][1,3]dioxole-5-carbaldehyde (510 mg, 3.40 mmol).

REFERENCE EXAMPLE 33 tert-butyl 6-(2,2,2-trifluoro-1-hydroxyethyl)-1H-indazole-1-carboxylate (Compound A33)

Step 1

In dichloromethane (3.0 mL) was suspended 1H-indazole-6-carbaldehyde (231 mg, 1.75 mmol). Di-tert-butyl dicarbonate (0.45 mL, 1.9 mmol) and 4-dimethylaminopyridine (18.4 mg, 0.151 mmol) were added and the mixture was stirred at room temperature for 30 minutes. The solvent was evaporated under reduced pressure. The residue was purified by silica gel column chromatography (hexane/ethyl acetate=1/1) to give tert-butyl 6-formyl-1H-indazole-1-carboxylate (389 mg, 90% yield).

Step 2

According to Step 1 of Reference Example 10, Compound A33 (278 mg, 56% yield) was obtained from tert-butyl 6-formyl-1H-indazole-1-carboxylate (389 mg, 1.58 mmol) obtained in Step 1.

ESIMS m/z: 317 (M+H)$^+$.

REFERENCE EXAMPLE 34 tert-butyl 5-(2,2,2-trifluoro-1-hydroxyethyl)-1H-indazole-1-carboxylate (Compound A34)

According to Reference Example 33, Compound A34 (235 mg, steps 56-% yield) was obtained from tert-butyl 5-formyl-1H-indazole-1-carboxylate (193 mg, 1.32 mmol).

ESIMS m/z: 317 (M+H)$^+$.

REFERENCE EXAMPLE 35

2,2,2-trifluoro-1-(pyrimidin-5-yl)ethanol (Compound A35)

According to Step 1 of Reference Example 10, Compound A35 (342 mg, 69% yield) was obtained from pyrimidine-5-carbaldehyde (300 mg, 2.46 mmol).

ESIMS m/z: 179 (M+H)$^+$.

REFERENCE EXAMPLE 36

2,2,2-trifluoro-1-(2-methylpyrimidin-5-yl)ethanol (Compound A36)

According to Step 1 of Reference Example 10, Compound A36 (672 mg, 85% yield) was obtained from 2-methylpyrimidine-5-carbaldehyde (500 mg, 4.09 mmol).

ESIMS m/z: 193 (M+H)$^+$.

REFERENCE EXAMPLE 37

N-(3-chloroquinoxalin-2-yl)-2-methoxy-N-((2-(trimethylsilyl)ethoxy)methyl)ethanesulfonamide (Compound A37)

Step 1

In water (16 mL) was suspended 1-bromo-2-methoxyethane (2.00 mL, 21.3 mmol). Sodium sulfite (2.95 g, 23.4 mmol) was added and the mixture was refluxed for 24 hours. The solvent in the reaction mixture was evaporated under reduced pressure and the residue was purified by slurrying in chloroform to give a white solid (6.11 g). To the white solid were added thionyl chloride (15.5 mL, 213 mmol) and DMF (0.082 mL, 1.06 mmol) and the mixture was stirred at 100° C. for 3 hours. The solvent in the reaction mixture was evaporated under reduced pressure. Chloroform was added, insoluble substance was filtered off, and the solvent in the filtrate was evaporated under reduced pressure. A 25% aqueous ammonia solution (10 mL) was added to the resulting residue and the mixture was stirred at room temperature for 3 hours. The solvent in the reaction mixture was evaporated under reduced pressure. Chloroform was added, insoluble substance was filtered off, and the solvent in the filtrate was evaporated under reduced pressure. The residue was purified by silica gel column chromatography (hexane/ethyl acetate=3/7) to give 2-methoxyethanesulfonamide (1.36 g, 46% yield).

Step 2

According to Reference Example 1, N-(3-chloroquinoxalin-2-yl)-2-methoxyethanesulfonamide (537 mg, 80% yield) was obtained from 2-methoxyethanesulfonamide (308 mg, 2.21 mmol) obtained in Step 1.

Step 3

According to Reference Example 5, Compound A37 (1.38 g, 96% yield) was obtained from N-(3-chloroquinoxalin-2-yl)-2-methoxyethanesulfonamide (1.00 g, 3.31 mmol) obtained in Step 2.

REFERENCE EXAMPLE 38

3-(5-(1-(3-chloroquinoxalin-2-yloxy)-2,2,2-trifluoro-ethyl)pyridin-2-yl)-5-methyl-1,2,4-oxadiazole (Compound A38)

Step 1

According to Step 2 of Reference Example 11, 5-(diethoxymethyl)picolinonitrile (884 mg, 59% yield) was obtained from 2-bromo-5-(diethoxymethyl)pyridine (1.89 g, 7.27 mmol) obtained in Step 1 of Reference Example 43.

Step 2

In ethanol (5 mL) was dissolved 5-(diethoxymethyl)picolinonitrile (230 mg, 1.12 mmol) obtained in Step 1. A 50% aqueous hydroxylamine solution (0.368 g, 5.58 mmol) was added and the mixture was stirred at room temperature for 1 hour. Water was added to the reaction mixture. Extraction with ethyl acetate, washing with saturated brine and drying over anhydrous sodium sulfate were performed. After filtration, the solvent in the filtrate was evaporated under reduced pressure. The resulting white solid was dissolved in pyridine (5 mL). Acetyl chloride (0.396 mL, 5.58 mmol) was added and the mixture was stirred at 100° C. for 12 hours. The solvent in the reaction mixture was evaporated under reduced pressure and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=3/7) to give 6-(5-methyl-1,2,4-oxadiazol-3-yl)nicotinaldehyde (200 mg, 95% yield).

Step 3

According to Step 1 of Reference Example 10, 2,2,2-trifluoro-1-(6-(5-methyl-1,2,4-oxadiazol-3-yl)pyridin-3-yl)ethanol (189 mg, 69% yield) was obtained from 6-(5-methyl-1,2,4-oxadiazol-3-yl)nicotinaldehyde (200 mg, 1.05 mmol) obtained in. Step 2.

Step 4

According to Step 3 of Reference Example 9, Compound A38 (146 mg, 48% yield) was obtained from 2,2,2-trifluoro-1-(6-(5-methyl-1,2,4-oxadiazol-3-yl)pyridin-3-yl)ethanol (189 mg, 0.729 mg) obtained in Step 3.

REFERENCE EXAMPLE 39

2-chloro-3-(2,2,2-trifluoro-1-(6-(1-methyl-1H-pyrazol-5-yl)pyridin-3-yl)ethoxy)quinoxaline (Compound A39)

Step 1

According to Reference Example 26, 2,2,2-trifluoro-1-(6-(1-methyl-1H-pyrazol-5-yl)pyridin-3-yl)ethanol (777 mg, 77% yield) was obtained from 1-(6-bromopyridin-3-yl)-2,2,2-trifluoroethanol (1.00 g, 3.91 mmol) and 1-methyl-5-(4,4,5,5-tetramethyl-1,3,2-dioxaborolan-2-yl)-1H-pyrazole (1.12 mg, 5.86 mmol).

Step 2

According to Step 3 of Reference Example 9, Compound A39 (144 mg, 88% yield) was obtained from 2,2,2-trifluoro-1-(6-(1-methyl-1H-pyrazol-5-yl)pyridin-3-yl)ethanol (100 mg, 0.389 mg) obtained in Step 1.

REFERENCE EXAMPLE 40

2-chloro-3-(2,2,2-trifluoro-1-(6-(2-methyl-2H-1,2,3-triazol-4-yl)pyridin-3-yl)ethoxy)quinoxaline (Compound A40)

According to Step 3 of Reference Example 9, Compound A40 (528 mg, 80%. yield) was obtained from Compound A43 (406 mg, 1.57 mmol) in Reference Example 43.

REFERENCE EXAMPLE 41

2-chloro-3-(2,2,2-trifluoro-1-(6-(2-methyl-1H-imidazol-1-yl)pyridin-3-yl)ethoxy)quinoxaline (Compound A41)

Step 1

In DMSO (5 mL) was dissolved 2-methyl-1H-imidazole (575 mg, 7.00 mmol). To the solution 60% sodium hydride (in oil) (323 mg, 8.08 mmol) was added at 0° C. and the mixture was stirred at room temperature for 30 minutes. Ethyl 6-chloronicotinate (1.00 g, 5.39 mmol) was added and the mixture was stirred at room temperature for 30 minutes. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (chloroform/methanol=97/3) to give ethyl 6-(2-methyl-1H-imidazol-1-yl)nicotinate (455 mg, 37% yield).

Step 2

Lithium aluminum hydride (164 mg, 4.33 mmol) was suspended in THF (5 mL). A solution of ethyl 6-(2-methyl-1H-imidazol-1-yl)nicotinate (455 mg, 1.96 mmol) obtained in Step 1 in THF (5 mL) was added at 0° C. and the mixture was stirred at 0° C. for 30 minutes. To the reaction mixture were sequentially added water (0.146 mL), a 15% aqueous sodium hydroxide solution (0.146 mL), and water (0.492 mL), and the mixture was stirred at room temperature for 1 hour. The reaction mixture was filtered through Celite. The solvent in the filtrate was evaporated under reduced pressure. The residue was purified by silica gel column chromatography (chloroform/methanol=97/3) to give (6-(2-methyl-1H-imidazol-1-yl)pyridin-3-yl)methanol (341 mg, 92% yield).

Step 3

In dichloromethane (5 mL) was dissolved (6-(2-methyl-1H-imidazol-1-yl)pyridin-3-yl)methanol (340 mg, 1.80 mmol) obtained in Step 2. Dess-Martin periodinane (915 mg, 2.16 mmol) was added and the mixture was stirred at room temperature for 1 hour. To the reaction mixture were added a saturated aqueous sodium bicarbonate solution and a saturated aqueous sodium thiosulfate solution and the mixture was stirred at room temperature for 1 hour. Extraction with dichloromethane and drying over anhydrous sodium sulfate were performed. After filtration, the solvent in the filtrate was evaporated under reduced pressure. The residue was purified by silica gel column chromatography (chloroform/methanol=19/1) to give 6-(2-methyl-1H-imidazol-1-yl)nicotinaldehyde (292 mg, 87% yield).

Step 4

According to Step 1 of Reference Example 10, 2,2,2-trifluoro-1-(6-(2-methyl-1H-imidazol-1-yl)pyridin-3-yl)ethanol (272 mg, 68% yield) was obtained from 6-(2-methyl-1H-imidazol-1-yl)nicotinaldehyde (292 mg, 1.56 mmol) obtained in Step 2.
Step 5
According to Step 3 of Reference Example 9, Compound A41 (104 mg, 89% yield) was obtained from 2,2,2-trifluoro-1-(6-(2-methyl-1H-imidazol-1-yl)pyridin-3-yl)ethanol (72.0 mg, 0.280 mg) obtained in Step 4.

REFERENCE EXAMPLE 42

1-(4-(1-(3-chloroquinoxalin-2-yloxy)-2,2,2-trifluoroethyl) pyridin-2-yl)ethanone (Compound A42)

Step 1
According to Step 1 of Reference Example 10, 1-(2-bromopyridin-4-yl)-2,2,2-trifluoroethanol (7.96 g, 58% yield) was obtained from 2-bromoisonicotinaldehyde (9.90 g, 53.2 mmol).
Step 2
In dichloromethane (50 mL) was dissolved 1-(2-bromopyridin-4-yl)-2,2,2-trifluoroethanol (5.00 g, 19.5 mmol) obtained in Step 1. Triethylamine (10.2 mL, 73.2 mmol) and tert-butyldimethylsilyl trifluoromethanesulfonate (7.41 mL, 32.3 mmol) were added under ice-cooling and the mixture was stirred at room temperature for 9.5 hours. Water was added to the reaction mixture. Extraction with ethyl acetate and drying over anhydrous magnesium sulfate were performed. After filtration, the solvent in the filtrate was evaporated under reduced pressure. The residue was purified by silica gel column chromatography (hexane/ethyl acetate=4/1) to give 2-bromo-4-(1-(tert-butyldimethylsilyloxy)-2,2,2-trifluoroethyl)pyridine (6.43 g, 89% yield).
Step 3
To toluene (9 mL) were added dropwise at −78° C. n-butyllithium (2.66 mol/L solution in n-hexane, 1.12 mL, 2.97 mmol) and a solution of 2-bromo-4-(1-(tert-butyldimethylsilyloxy)-2,2,2-trifluoroethyl)pyridine (1.00 g, 2.70 mmol) obtained in Step 2 in toluene (3.0 mL), and the mixture was stirred at the same temperature for 30 minutes. THF (3.0 mL) was added to the resulting solution and the mixture was stirred at −78° C. for 30 minutes. N-methoxy-N-methylacetamide (1.38 mL, 13.5 mmol) was added and the mixture was stirred for 2 hours allowing the temperature to rise slowly to room temperature. A saturated aqueous ammonium chloride solution and water were added to the reaction mixture. Extraction with ethyl acetate and drying over anhydrous magnesium sulfate were performed. After filtration, the solvent in the filtrate was evaporated under reduced pressure. The residue was purified by silica gel column chromatography (hexane/ethyl acetate=4/1) to give 1-(4-(1-(tert-butyldimethylsilyloxy)-2,2,2-trifluoroethyl)pyridin-2-yl)ethanone (645 mg, 72% yield).
Step 4
In THF (6 mL) was dissolved 1-(4-(1-(tert-butyldimethylsilyloxy)-2,2,2-trifluoroethyl)pyridin-2-yl)ethanone (645 mg, 1.93 mmol) obtained in Step 3. Tetrabutylammonium fluoride (1.0 mol/L solution in THF, 0.556 mL, 0.556 mmol) was added and the mixture was stirred at room temperature for 1 hour. A saturated aqueous ammonium chloride solution was added to the reaction mixture. Extraction with ethyl acetate and drying over anhydrous magnesium sulfate were performed. After filtration, the solvent in the filtrate was evaporated under reduced pressure. The residue was purified by silica gel column chromatography (hexane/ethyl acetate=1/1) to give 1-(4-(2,2,2-trifluoro-1-hydroxyethyl)pyridin-2-yl)ethanone (406 mg, 96% yield).
Step 5
According to Step 3 of Reference Example 9, Compound A42 (227 mg, 37% yield) was obtained from 1-(4-(2,2,2-trifluoro-1-hydroxyethyl)pyridin-2-yl)ethanone (350 mg, 1.60 mmol) obtained in Step 4.

REFERENCE EXAMPLE 43

2,2,2-trifluoro-1-(6-(2-methyl-2H-1,2,3-triazol-4-yl) pyridin-3-yl)ethanol (Compound A43)

Step 1
In ethanol (60 mL) was dissolved 6-bromonicotinaldehyde (2.00 g, 10.8 mmol). Triethyl orthoformate (5.37 mL, 32.3 mmol) and p-toluenesulfonic acid monohydrate (102 mg, 0.538 mmol) were added and the mixture was refluxed for 2 hours. The solvent in the reaction mixture was evaporated under reduced pressure, and a saturated aqueous sodium bicarbonate solution and water were added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=9/1) to give 2-bromo-5-(diethoxymethyl)pyridine (2.59 g, 92% yield).
Step 2
In THF (10 mL) was dissolved 2-bromo-5-(diethoxymethyl)pyridine (1.00 g, 3.84 mmol) obtained in Step 1. To the solution were added trimethylsilyl acetylene (1.09 mL, 7.69 mmol), copper iodide (I) (37.0 mg, 0.192 mmol), (bistriphenylphosphine) palladium (II) chloride (135 mg, 0.192 mmol), and triethylamine (1.07 mL, 7.69 mmol), and the mixture was stirred at 70° C. for 6 hours. The solvent in the reaction mixture was evaporated under reduced pressure, and water and ethyl acetate were added. The mixture was filtered through Celite and the filtrate was extracted with ethyl acetate. Washing with saturated brine and drying over anhydrous sodium sulfate were performed. After filtration, the solvent in the filtrate was evaporated under reduced pressure. The residue was purified by silica gel column chromatography (hexane/ethyl acetate=9/1) to give 5-(diethoxymethyl)-2-((trimethylsilyl)ethynyl)pyridine (1.07 g). In methanol (10 mL) was dissolved 5-(diethoxymethyl)-2-((trimethylsilyl) ethynyl)pyridine obtained. Potassium carbonate (1.06 g, 7.69 mmol) was added, and the mixture was stirred at room temperature for 1 hour. The solvent in the reaction mixture was evaporated under reduced pressure, and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give 5-(diethoxymethyl)-2-ethynylpyridine (703 mg, 89% yield).
Step 3
In tert-butanol (10 mL) was dissolved 5-(diethoxymethyl)-2-ethynylpyridine (1.41 g, 6.87 mmol) obtained in Step 2. To the solution were added azidomethyl pivalate (1.08 g, 6.87 mmol), water (10 mL), copper (II) sulfate pentahydrate (86.0 mg, 0.343 mmol) and sodium ascorbate (408 mg, 0.343 mmol), and the mixture was stirred at room temperature for 3 hours. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give (4-(5-(diethoxymethyl)pyridin-2-yl)-1H-1,2,3-triazol-1-yl)methyl pivalate (2.27 g, 91% yield).
Step 4
In methanol (12 mL) was dissolved (4-(5-(diethoxymethyl)pyridin-2-yl)-1H-1,2,3-triazol-1-yl)methyl pivalate (1.96 g, 5.41 mmol) obtained in Step 3. To the solution was added a 1 mol/L aqueous sodium hydroxide solution (11.9 mL, 11.9 mmol) and the mixture was stirred at room temperature for 5 minutes. To the reaction mixture were added 1 mol/L hydrochloric acid (11.9 mL) and water. Extraction with ethyl acetate, washing with saturated brine and drying over anhydrous sodium sulfate were performed. After filtration, the solvent in the filtrate was evaporated under reduced pressure to give 5-(diethoxymethyl)-2-(1H-1,2,3-triazol-4-yl) pyridine (1.34 g, 100% yield).
Step 5
In acetonitrile (25 mL) was dissolved 5-(diethoxymethyl)-2-(1H-1,2,3-triazol-4-yl) pyridine (1.34 g, 5.40 mmol) obtained in Step 4. To the solution were added potassium carbonate (2.24 g, 5.40 mmol) and iodomethane (0.405 mL, 6.48 mmol) and the mixture was stirred at room temperature for 5 hours. The reaction mixture was concentrated under reduced pressure and water was added. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=4/1) to give 5-(diethoxymethyl)-2-(2-methyl-2H-1,2,3-triazol-4-yl)pyridine (698 mg, 49% yield).
Step 6
In THF (6.5 mL) was dissolved 5-(diethoxymethyl)-2-(2-methyl-2H-1,2,3-triazol-4 yl)pyridine (672 mg, 2.56 mmol) obtained in Step 5. To the solution was added 1 mol/L hydrochloric acid (6.40 mL, 6.40 mmol) and the mixture was stirred at room temperature for 2 hours. A saturated aqueous sodium bicarbonate solution was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate 7/3) to give 6-(2-methyl-2H-1,2,3-triazol-4-yl)nicotinaldehyde (473 mg, 98% yield).
Step 7
According to Step 1 of Reference Example 10, Compound A43 (672 mg, 85% yield) was obtained from 6-(2-methyl-2H-1,2,3-triazol-4-yl)nicotinaldehyde (453 mg, 2.41 mmol) obtained in Step 6.

REFERENCE EXAMPLE 44

2,2,2-trifluoro-1-(6-(oxazol-5-yl)pyridin-3-yl)ethanol (Compound A44)

Step 1
To toluene (3 mL) were added dropwise at −78° C. n-butyllithium (2.6 mol/L solution in n-hexane, 0.94 mL, 2.43 mmol) and a solution of 2-bromo-5-(diethoxymethyl)pyridine (575 mg, 2.21 mmol) obtained in Step 1 of Reference Example 42 in toluene (2 mL), and the mixture was stirred at −78° C. for 30 minutes. THF (2 mL) was added to the resulting suspension and the mixture was stirred at −78° C. for 30 minutes. DMF (0.51 mL, 6.63 mmol) was added and the mixture was stirred for 30 minutes allowing the temperature to rise slowly to room temperature. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=9/1) to give 5-(diethoxymethyl)picolinaldehyde (149 mg, 32% yield).
Step 2
In methanol (5 mL) was dissolved 5-(diethoxymethyl)picolinaldehyde (148 mg, 0.707 mmol) obtained in Step 1. To the solution were added toluene-4-sulfonylmethylisocyanide (345 mg, 1.77 mmol) and potassium carbonate (244 mg, 1.77 mmol) and the mixture was stirred at room temperature for 8 hours. Water was added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=7/3) to give 5-(5-(diethoxymethyl)pyridin-2-yl)oxazole (161 mg, 92% yield).
Step 3
According to Step 6 of Reference Example 43, 6-(oxazol-5-yl)nicotinaldehyde (98.1 mg, 88% yield) was obtained from 5-(5-(diethoxymethyl)pyridin-2-yl)oxazole (160 mg, 0.647 mmol) obtained in Step 2.
Step 4
According to Step 1 of Reference Example 10, Compound A44 (124 mg, 90% yield) was obtained from 6-(oxazol-5-yl) nicotinaldehyde (98.2 mg, 0.564 mmol) obtained in Step 3.

REFERENCE EXAMPLE 45

1-(1,2-dimethyl-1H-imidazol-5-yl)-2,2,2-trifluoroethanol (Compound A45)

Step 1
In DMF (10 mL) was dissolved 2-methyl-1H-imidazole-5-carbaldehyde (1.00 g, 9.08 mmol). Potassium carbonate (2.51 g, 18.2 mmol) and methyl p-toluenesulfonate (2.06 mL, 13.6 mmol) were added under ice-cooling and the mixture was stirred at room temperature for 6 hours. A 1 mol/L aqueous sodium hydroxide solution and water were added to the reaction mixture. Extraction with ethyl acetate, washing with a 1 mol/L aqueous sodium hydroxide solution and drying over anhydrous magnesium sulfate were performed. After filtration, the solvent in the filtrate was evaporated under reduced pressure. The residue was purified by silica gel column chromatography (chloroform/methanol=19/1) to give 1,2-dimethyl-1H-imidazole-5-carbaldehyde (180 mg, 16% yield).
Step 2
According to Step 1 of Reference Example 10, Compound A45 (232 mg, 85%) was obtained from 1,2-dimethyl-1H-imidazole-5-carbaldehyde (180 mg, 1.45 mmol) obtained in Step 1.

REFERENCE EXAMPLE 46

1-(5-(2,2,2-trifluoro-1-hydroxyethyl)thiazol-2-yl) ethanone (Compound A46)

Step 1
According to Step 1 of Reference Example 10, 1-(2-bromothiazol-5-yl)-2,2,2-trifluoroethanol (413 mg, 25%) was obtained from 2-bromothiazole-5-carbaldehyde (1.20 g, 6.25 mmol).

Step 2

According to Step 2 of Reference Example 42, 2-bromo-5-(1-(tert-butyldimethylsilyloxy)-2,2,2-trifluoroethyl)thiazole (524 mg, 88%) was obtained from 1-(2-bromothiazol-5-yl)-2,2,2-trifluoroethanol (413 mg, 1.58 mmol) obtained in Step 1.

Step 3

In THF (5 mL) was dissolved 2-bromo-5-(1-(tert-butyldimethylsilyloxy)-2,2,2-trifluoroethyl)thiazole (515 mg, 1.37 mmol) obtained in Step 2. n-Butyllithium (1.65 mol/L solution in n-hexane, 1.24 mL, 2.05 mmol) was added dropwise at −78° C. and the mixture was stirred at −78° C. for 30 minutes. A solution of N-methoxy-N-methylacetamide (1.38 mL, 13.7 mmol) in THF (1 mL) was added to the reaction mixture and the mixture was stirred at −78° C. for 2 hours. A saturated aqueous ammonium chloride solution and water were added to the reaction mixture. Extraction with ethyl acetate and drying over anhydrous magnesium sulfate were performed. After filtration, the solvent in the filtrate was evaporated under reduced pressure. The residue was purified by silica gel column chromatography (hexane/ethyl acetate=4/1) to give 1-(5-(1-(tert-butyldimethylsilyloxy)-2,2,2-trifluoroethyl) thiazol-2-yl)ethanone (437 mg, 94%).

Step 4

In THF (3 mL) was dissolved 1-(5-(1-(tert-butyldimethylsilyloxy)-2,2,2-trifluoroethyl) thiazol-2-yl)ethanone (356 mg, 1.05 mmol) obtained in Step 3. To the solution were added acetic acid (0.072 mL, 1.26 mmol) and tetrabutylammonium fluoride (1.0 mol/L solution in THF, 1.26 mL, 1.26 mmol) and the mixture was stirred at room temperature for 1 hour. A saturated aqueous sodium carbonate solution was added to the reaction mixture. Extraction with ethyl acetate, washing with a saturated aqueous ammonium chloride solution and drying over anhydrous magnesium sulfate were performed. After filtration, the solvent in the filtrate was evaporated under reduced pressure. The residue was purified by silica gel column chromatography (hexane/ethyl acetate=1/1) to give Compound A46 (214 mg, 91%).

REFERENCE EXAMPLE 47

3-chloro-6-iodo-2-(2,2,2-trifluoro-1-(pyridin-3-yl)ethoxy) quinoxaline (Compound A47)

Step 1

According to Step 1 of Reference Example 10, 2,2,2-trifluoro-1-(pyridin-3-yl)ethanol (16.6 g, 99% yield) was obtained from nicotinaldehyde (9.00 mL, 95.4 mmol).

Step 2

In THF (200 mL) was dissolved 2,3-dichloro-6-nitroquinoxaline (4.00 g, 16.4 mmol) and the mixture was cooled to −78° C. To the solution were added 2,2,2-trifluoro-1-(pyridin-3-yl)ethanol (3.05 g, 17.2 mmol) obtained in Step 1 and sodium hydride (1.31 g, 32.8 mmol) and the mixture was stirred at −78° C. allowing the temperature to rise slowly to −30° C. over 1 hour. A saturated aqueous ammonium chloride solution was added to the reaction mixture. Extraction with ethyl acetate, washing with saturated brine and drying over anhydrous magnesium sulfate were performed. After filtration, the solvent in the filtrate was evaporated under reduced pressure. The residue was purified by silica gel column chromatography (hexane/ethyl acetate=1/0 to 3/2) to give 3-chloro-6-nitro-2-(2,2,2-trifluoro-1-(pyridin-3-yl)ethoxy) quinoxaline (3.98 g, 63% yield).
ESIMS m/z: 385 (M+H)$^+$.

Step 3

In a mixed solvent of ethanol (19.5 mL) and water (9.75 mL) was dissolved 3-chloro-6-nitro-2-(2,2,2-trifluoro-1-(pyridin-3-yl)ethoxy)quinoxaline (975 mg, 2.53 mmol) obtained in Step 2. To the solution were added iron (0) (425 mg, 7.60 mmol) and ammonium chloride (68.0 mg, 1.27 mmol) and the mixture was stirred at 80° C. for 1 hour. The reaction mixture was filtered through Celite and the filtrate was extracted with ethyl acetate. Washing with saturated brine and drying over anhydrous magnesium sulfate were performed. After filtration, the solvent in the filtrate was evaporated under reduced pressure. The residue was purified by silica gel column chromatography (hexane/ethyl acetate=1/0 to 0/1) to give 3-chloro-2-(2,2,2-trifluoro-1-(pyridin-3-yl)ethoxy) quinoxaline-6-amine (555 mg, 62% yield).
ESIMS m/z: 355 (M+H)$^+$.

Step 4

In 2.0 mol/L hydrochloric acid (50.0 mL) was dissolved 3-chloro-2-(2,2,2-trifluoro-1-(pyridin-3-yl)ethoxy) quinoxaline-6-amine (2.00 g, 5.64 mmol) obtained in Step 3 and the mixture was cooled to 0° C. Sodium nitrite (506 mg, 7.33 mmol) was added and the mixture was stirred at 0° C. for 10 minutes. Urea (508 mg, 8.46 mmol) was added to the reaction mixture and the mixture was stirred at 0° C. for 10 minutes. Potassium iodide (2.34 g, 14.1 mmol) dissolved in water (10.0 mL) was slowly added and the mixture was stirred at room temperature for 30 minutes. A saturated aqueous sodium bicarbonate solution and a saturated aqueous sodium thiosulfate solution were added to the reaction mixture. Extraction with ethyl acetate, washing with saturated brine and drying over anhydrous magnesium sulfate were performed. After filtration, the solvent in the filtrate was evaporated under reduced pressure. The residue was purified by silica gel column chromatography (hexane/ethyl acetate=1/0 to 3/2) to give Compound A47 (868 mg, 33% yield).
ESIMS m/z: 466 (M+H)$^+$.

EXAMPLE 1

N-(3-(2-hydroxy-2-methyl-1-(pyridin-3-yl)propoxy)quinoxalin-2-yl)propane-1-sulfonamide (Compound 1)

In THF (5 mL) were dissolved Compound A1 (235 mg, 0.821 mmol) obtained in Reference Example 1 and Compound A14 (206 mg, 1.23 mmol) obtained in Reference Example 14. To the mixture was added 60% sodium hydride (in oil, 82.1 mg, 2.05 mmol) and the mixture was stirred at 50° C. for 9 hours. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (ethyl acetate: 100%) to give Compound 1 (279 mg, 82% yield).
ESIMS m/z: 417 (M+H)$^+$.

EXAMPLE 2

3-(2-hydroxy-2-methyl-1-(3-(propylsulfonamido)quinoxalin-2-yloxy)propyl)pyridine 1-oxide (Compound 2)

Compound 1 (89.6 mg, 0.215 mmol) obtained in Example 1 was dissolved in dichloromethane (5.0 mL). To the solution was added 65% meta-chloroperbenzoic acid (85.7 mg, 0.323 mmol) and the mixture was stirred at room temperature for 2 hours. The solvent was evaporated under reduced pressure. The residue was purified by preparative thin-layer chromatography (chloroform/methanol=9/1) to give Compound 2 (47.7 mg, 51% yield).

ESIMS m/z: 433 (M+H)$^+$.

EXAMPLE 3

N-(3-(2,2-dimethyl-1-(pyridin-3-yl)propoxy)quinoxalin-2-yl) propane-1-sulfonamide (Compound 3)

According to Example 1, Compound 3 (189 mg, 65% yield) was obtained from Compound A1 (200 mg, 0.700 mmol) obtained in Reference Example 1 and Compound A15 (173 mg, 1.05 mmol) obtained in Reference Example 15.

ESIMS m/z: 415 (M+H)$^+$.

EXAMPLE 4

3-(2,2-dimethyl-1-(3-(propylsulfonamido)quinoxalin-2-yloxy) propyl)pyridine 1-oxide (Compound 4)

According to Example 2, Compound 4 (135 mg, 97% yield) was obtained from Compound 3 (134 mg, 0.323 mmol) obtained in Example 3.

ESIMS m/z: 431 (M+H)$^+$.

EXAMPLE 5

N-(3-(cyclopropyl(pyridin-3-yl)methoxy)quinoxalin-2-yl) propane-1-sulfonamide (Compound 5)

According to Example 1, Compound 5 (209 mg, 75% yield) was obtained from Compound A1 (200 mg, 0.700 mmol) obtained in Reference Example 1 and Compound A16 (157 mg, 1.05 mmol) obtained in Reference Example 16.

ESIMS m/z: 399 (M+H)$^+$.

EXAMPLE 6

3-(cyclopropyl(3-(propylsulfonamido)quinoxalin-2-yloxy)methyl)pyridine 1-oxide (Compound 6)

According to Example 2, Compound 6 (135 mg, 93% yield) was obtained from Compound 5 (140 mg, 0.351 mmol) obtained in Example 5.

ESIMS m/z: 415 (M+H)$^+$.

EXAMPLE 7

N-(3-(2-fluoro-2-methyl-1-(pyridin-3-yl)propoxy)quinoxalin-2-yl)propane-1-sulfonamide (Compound 7)

According to Example 1, Compound 7 (274 mg, 93% yield) was obtained from Compound A1 (200 mg, 0.700 mmol) obtained in Reference Example 1 and Compound A17 (178 mg, 1.05 mmol) obtained in Reference Example 17.

ESIMS m/z: 419 (M+H)$^+$.

EXAMPLE 8

3-(2-fluoro-2-methyl-1-(3-(propylsulfonamido)quinoxalin-2-yloxy)propyl)pyridine 1-oxide (Compound 8)

According to Example 2, Compound 8 (197 mg, 98% yield) was obtained from Compound 7 (194 mg, 0.464 mmol) obtained in Example 7.

ESIMS m/z: 435 (M+H)$^+$.

$^1$H-NMR (300 MHz, CDCl$_3$, δ): 1.12 (t, J=7.7 Hz, 3H), 1.39-1.64 (m, 6H), 1.93-2.05 (m, 2H), 3.77 (s, 2H), 6.26 (d, J=20.2 Hz, 1H), 7.28-7.89 (m, 6H), 8.57 (dd, J=1.8, 4.8 Hz, 1H), 8.77 (d, J=1.8 Hz, 1H).

EXAMPLE 9

N-(3-(pyridin-3-ylmethoxy)quinoxalin-2-yl)propane-1-sulfonamide (Compound 9)

According to Example 1, Compound 9 (102 mg, 81% yield) was obtained from Compound A1 (100 mg, 0.350 mmol) obtained in Reference Example 1 and 3-pyridinemethanol (57.3 mg, 0.525 mmol).

ESIMS m/z: 359 (M+H)$^+$.

EXAMPLE 10

3-((3-(propylsulfonamido)quinoxalin-2-yloxy)methyl)pyridine 1-oxide (Compound 10)

According to Example 2, Compound 10 (51.0 mg, 92% yield) was obtained from Compound 9 (53.1 mg, 0.148 mmol) obtained in Example 9.

ESIMS m/z: 375 (M+H)$^+$.

EXAMPLE 11

N-(3-(1-(pyridin-3-yl)pentyloxy)quinoxalin-2-yl)propane-1-sulfonamide (Compound 11)

According to Example 1, Compound 11 (202 mg, 93% yield) was obtained from Compound A1 (150 mg, 0.525 mmol) obtained in Reference Example 1 and Compound A18 (130 mg, 0.787 mmol) obtained in Reference Example 18.

ESIMS m/z: 415 (M+H)$^+$.

EXAMPLE 12

3-(1-(3-(propylsulfonamido)quinoxalin-2-yloxy)pentyl)pyridine 1-oxide (Compound 12)

According to Example 2, Compound 12 (81.5 mg, 77% yield) was obtained from Compound 11 (102 mg, 0.246 mmol) obtained in Example 11.

ESIMS m/z: 431 (M+H)$^+$.

EXAMPLE 13

N-(3-((1-methylcyclopropyl)(pyridin-3-yl)methoxy)quinoxalin-2-yl)propane-1-sulfonamide (Compound 13)

Compound A9 (147 mg, 0.451 mmol) obtained in Reference Example 9 and propane-1-sulfonamide (61.1 mg, 0.496 mol) were dissolved in DMSO (3.0 mL). Potassium carbonate (68 . 6 mg, 0.496 mmol) was added, and the mixture was stirred at 150° C. for 1 hour. A saturated aqueous ammonium chloride solution and water were added to the reaction mixture. Extraction with ethyl acetate, washing with saturated brine and drying over anhydrous sodium sulfate were performed. After filtration, the solvent in the filtrate was evaporated under reduced pressure. The residue was purified by silica gel column chromatography (hexane/ethyl acetate=7/3) to give Compound 13 (136 mg, 73% yield).

ESIMS m/z: 413 (M+H)$^+$.

EXAMPLE 14

3-((1-methylcyclopropyl)(3-(propylsulfonamido)quinoxalin-2-yloxy)methyl)pyridine 1-oxide (Compound 14)

According to Example 2, Compound 14 (84.5 mg, 81% yield) was obtained from Compound 13 (100 mg, 0.242 mmol) obtained in Example 13.
ESIMS m/z: 429 (M+H)$^+$.

EXAMPLE 15

N-(3-(1-(pyridin-3-yl)propoxy)quinoxalin-2-yl)propane-1-sulfonamide (Compound 15)

According to Example 1, Compound 15 (163 mg, 80% yield) was obtained from Compound A1 (150 mg, 0.525 mmol) obtained in Reference Example 1 and Compound A19 (103 mg, 0.752 mmol) obtained in Reference Example 19.
ESIMS m/z: 387 (M+H)$^+$.

EXAMPLE 16

3-(1-(3-(propylsulfonamido)quinoxalin-2-yloxy)propyl)pyridine 1-oxide (Compound 16)

According to Example 2, Compound 16 (95.6 mg, 92% yield) was obtained from Compound 15 (100 mg, 0.259 mmol) obtained in Example 15.
ESIMS m/z: 402 (M+H)$^+$.

EXAMPLE 17

N-(3-(2,2-difluoro-1-(pyridin-3-yl)ethoxy)quinoxalin-2-yl) propane-1-sulfonamide (Compound 17)

According to Example 1, Compound 17 (159 mg, 74% yield) was obtained from Compound A1 (150 mg, 0.525 mmol) obtained in Reference Example 1 and Compound A20 (121 mg, 0.760 mmol) obtained in Reference Example 20.
ESIMS m/z: 409 (M+H)$^+$.

EXAMPLE 18

3-(2,2-difluoro-1-(3-(propylsulfonamido)quinoxalin-2-yloxy)ethyl)pyridine 1-oxide (Compound 18)

According to Example 2, Compound 18 (97.5 mg, 96% yield) was obtained from Compound 17 (100 mg, 0.245 mmol) obtained in Example 17.
ESIMS m/z: 424 (M+H)$^+$.

EXAMPLE 19

N-(3-(1-(pyridin-3-yl)ethoxy)quinoxalin-2-yl)propane-1-sulfonamide (Compound 19)

According to Example 1, Compound 19 (128 mg, 65% yield) was obtained from Compound A1 (150 mg, 0.525 mmol) obtained in Reference Example 1 and Compound A21 (96.7 mg, 0.787 mmol) obtained in Reference Example 21.
ESIMS m/z: 373 (M+H)$^+$.

EXAMPLE 20

3-(1-(3-(propylsulfonamido)quinoxalin-2-yloxy)ethyl)pyridine 1-oxide (Compound 20)

According to Example 2, Compound 20 (87.3 mg, 100% yield) was obtained from Compound 19 (73.3 mg, 0.197 mmol) obtained in Example 19.
ESIMS m/z: 389 (M+H)$^+$.

EXAMPLE 21

N-(3-(1-(pyridin-3-yl)butoxy)quinoxalin-2-yl)propane-1-sulfonamide (Compound 21)

According to Example 1, Compound 21 (179 mg, 85% yield) was obtained from Compound A1 (150 mg, 0.525 mmol) obtained in Reference Example 1 and Compound A22 (119 mg, 0.787 mmol) obtained in Reference Example 22.
ESIMS m/z: 401 (M+H)$^+$.

EXAMPLE 22

3-(1-(3-(propylsulfonamido)quinoxalin-2-yloxy)butyl)pyridine 1-oxide (Compound 22)

According to Example 2, Compound 22 (112 mg, 81% yield) was obtained from Compound 21 (120 mg, 0.300 mmol) obtained in Example 21.
ESIMS m/z: 417 (M+H)$^+$.

EXAMPLE 23

N-(3-(phenyl(pyridin-3-yl)methoxy)quinoxalin-2-yl)propane-1-sulfonamide (Compound 23)

According to Example 1, Compound 23 (155 mg, 100% yield) was obtained from Compound A1 (150 mg, 0.525 mmol) obtained in Reference Example 1 and Compound A23 (144 mg, 0.787 mmol) obtained in Reference Example 23.
ESIMS m/z: 435 (M+H)$^+$.

EXAMPLE 24

3-(phenyl(3-(propylsulfonamido)quinoxalin-2-yloxy)methyl)pyridine 1-oxide (Compound 24)

According to Example 2, Compound 24 (89.8 mg, 89% yield) was obtained from Compound 23 (97.7 mg, 0.225 mmol) obtained in Example 23.
ESIMS m/z: 451 (M+H)$^+$.

EXAMPLE 25

N-(3-(2,2,2-trifluoro-1-(4-(methylsulfonyl)phenyl)ethoxy) quinoxalin-2-yl)propane-1-sulfonamide (Compound 25)

According to Example 13, Compound 25 (59.2 mg, 49% yield) was obtained from Compound A10 (100 mg, 0.240 mmol) obtained in Reference Example 10.
ESIMS m/z: 504 (M+H)$^+$.

EXAMPLE 26

N-(3-(1-(6-cyanopyridin-3-yl)-2,2,2-trifluoroethoxy) quinoxalin-2-yl)propane-1-sulfonamide (Compound 26)

According to Example 13, Compound 26 (23.5 mg, 14% yield) was obtained from Compound A11 (133 mg, 0.362 mmol) obtained in Reference Example 11.

ESIMS m/z: 452 (M+H)$^+$.

EXAMPLE 27

N-(3-(2,2,2-trifluoro-1-(imidazo[1,2-a]pyridin-6-yl) ethoxy) quinoxalin-2-yl)propane-1-sulfonamide (Compound 27)

According to Example 1, Compound 27 (82.4 mg, 77% yield) was obtained from Compound A1 (66.1 mg, 0.231 mmol) obtained in Reference Example 1 and Compound A24 (50.0 mg, 0.231 mmol) obtained in Reference Example 24.

ESIMS m/z: 467 (M+H)$^+$.

EXAMPLE 28

N-(3-(2,2,2-trifluoro-1-(imidazo[1,2-a]pyridin-6-yl) ethoxy) quinoxalin-2-yl)butane-1-sulfonamide (Compound 28)

According to Example 1, Compound 28 (69.6 mg, 63% yield) was obtained from Compound A2 (69.2 mg, 0.231 mmol) obtained in Reference Example 2 and Compound A24 (50.0 mg, 0.231 mmol) obtained in Reference Example 24.

ESIMS m/z: 480 (M+H)$^+$.

EXAMPLE 29

2-methyl-N-(3-(2,2,2-trifluoro-1-(imidazo[1,2-a] pyridin-6-yl)ethoxy)quinoxalin-2-yl)propane-1-sulfonamide (Compound 29)

According to Example 1, Compound 29 (60.4 mg, 55% yield) was obtained from Compound A3 (69.2 mg, 0.231 mmol) obtained in Reference Example 3 and Compound A24 (50.0 mg, 0.231 mmol) obtained in Reference Example 24.

ESIMS m/z: 480 (M+H)$^+$.

EXAMPLE 30

1-cyclopropyl-N-(3-(2,2,2-trifluoro-1-(imidazo[1,2-a]pyridin-6-yl)ethoxy)quinoxalin-2-yl)methanesulfonamide (Compound 30)

According to Example 1, Compound 30 (102 mg, 92% yield) was obtained from Compound A4 (68.8 mg, 0.231 mmol) obtained in Reference Example 4 and Compound A24 (50.0 mg, 0.231 mmol) obtained in Reference Example 24.

ESIMS m/z: 478 (M+H)$^+$.

EXAMPLE 31

N-(3-(2,2,2-trifluoro-1-(6-(hydroxymethyl)pyridin-3-yl)ethoxy)quinoxalin-2-yl)propane-1-sulfonamide (Compound 31)

Step 1

N-(3-(2,2,2-trifluoro-1-(6-methylpyridin-3-yl) ethoxy) quinoxalin-2-yl)propane-1-sulfonamide (Compound B1)

According to Example 1, Compound B1 (690 mg, 64% yield) was obtained from Compound A1 (703 mg, 2.46 mmol) obtained in Reference Example 1 and Compound A25 (470 mg, 2.46 mmol) obtained in Reference Example 25.

Step 2

2-methyl-5-(2,2,2-trifluoro-1-(3-(propylsulfonamido) quinoxalin-2-yloxy)ethyl)pyridine 1-oxide (Compound B2)

According to Example 2, Compound B2 (707 mg, 99% yield) was obtained from Compound B1 (690 mg, 1.57 mmol) obtained in Step 1.

Step 3

N-(3-(2,2,2-trifluoro-1-(6-(hydroxymethyl)pyridin-3-yl)ethoxy) quinoxalin-2-yl)propane-1-sulfonamide (Compound 31)

Compound B2 (103 mg, 0.226 mmol) obtained in Step 2 was suspended in acetic anhydride (1.0 mL) and the suspension was stirred at 100° C. for 1.5 hours. Water was added to the reaction mixture. Extraction with ethyl acetate, washing with saturated brine and drying over anhydrous sodium sulfate were performed. The solvent was evaporated under reduced pressure and the resulting residue was dissolved in methanol (2.0 mL). Potassium carbonate (93.7 mg, 0.678 mmol) was added and the mixture was stirred at room temperature for 30 minutes. The solvent was evaporated under reduced pressure, and a saturated aqueous ammonium chloride solution and water were added. Extraction with ethyl acetate, washing with saturated brine and drying over anhydrous sodium sulfate were performed. The solvent was evaporated under reduced pressure. The residue was purified by silica gel column chromatography (hexane/ethyl acetate=1/1) and further purified by preparative thin-layer chromatography (hexane/ethyl acetate=1/1) to give Compound 31 (30.8 mg, 30% yield).

ESIMS m/z: 457 (M+H)$^+$.

$^1$H-NMR (300 MHz, CDCl$_3$, δ): 1.12 (t, J=7.3 Hz, 3H), 1.93-2.06 (m, 2H), 3.49-3.78 (m, 3H), 4.79 (s, 2H), 6.79 (brs, 1H), 7.35-7.98 (m, 6H), 8.83 (d, J=1.8 Hz, 1H).

EXAMPLE 32

N-(3-(2,2,2-trifluoro-1-(6-(1-methyl-1H-pyrazol-4-yl)pyridin-3-yl)ethoxy)quinoxalin-2-yl)propane-1-sulfonamide (Compound 32)

According to Example 1, Compound 32 (48.9 mg, 47% yield) was obtained from Compound A1 (59.1 mg, 0.207 mmol) obtained in Reference Example 1 and Compound A26 (53.2 mg, 0.207 mmol) obtained in Reference Example 26.

ESIMS m/z: 507 (M+H)$^+$.

EXAMPLE 33

N-(3-(2,2,2-trifluoro-1-(6-(1-methyl-1H-pyrazol-4-yl)pyridin-3-yl)ethoxy)quinoxalin-2-yl)butane-1-sulfonamide (Compound 33)

According to Example 1, Compound 33 (52.8 mg, 49% yield) was obtained from Compound A2 (62.1 mg, 0.207 mmol) obtained in Reference Example 2 and Compound A26 (53.2 mg, 0.207 mmol) obtained in Reference Example 26.
ESIMS m/z: 521 (M+H)$^+$.
$^1$H-NMR (300 MHz, CDCl$_3$, δ): 0.97 (t, J=7.3 Hz, 3H), 1.46-1.59 (m, 2H), 1.89-1.99 (m, 2H), 3.81 (s, 2H), 3.95 (s, 3H), 6.78 (brs, 1H), 7.48-7.95 (m, 8H), 8.79 (d, J=1.8 Hz, 1H).

EXAMPLE 34

N-(3-(2,2,2-trifluoro-1-(6-(methylthio)pyridin-3-yl)ethoxy) quinoxalin-2-yl)propane-1-sulfonamide (Compound 34)

According to Example 1, Compound 34 (278 mg, 77% yield) was obtained from Compound A1 (218 mg, 0.763 mmol) obtained in Reference Example 1 and Compound A27 (170 mg, 0.763 mmol) obtained in Reference Example 27.
ESIMS m/z: 473 (M+H)$^+$.

EXAMPLE 35

N-(3-(2,2,2-trifluoro-1-(6-(methylsulfonyl)pyridin-3-yl)ethoxy)quinoxalin-2-yl)propane-1-sulfonamide (Compound 35) N-(3-(2,2,2-trifluoro-1-(6-(methylsulfinyl)pyridin-3-yl)ethoxy)quinoxalin-2-yl)propane-1-sulfonamide (Compound 36)

Compound 34 (222 mg, 0.470 mmol) obtained in Example 34 was dissolved in dichloromethane (5.0 mL), meta-chloroperbenzoic acid (67.8 mg, 1.17 mmol) was added, and the mixture was stirred at room temperature for 2 hours. A saturated aqueous sodium thiosulfate solution and water were added to the reaction mixture. Extraction with dichloromethane, washing with saturated brine and drying over anhydrous sodium sulfate were performed. After filtration, the solvent in the filtrate was evaporated under reduced pressure. The residue was purified by silica gel column chromatography (chloroform/methanol=1/1) to give Compound 35 (114 mg, 48% yield) and Compound 36 (110 mg, 48% yield).
Compound 35: ESIMS m/z: 505 (M+H)$^+$.
$^1$H-NMR (300 MHz, CDCl$_3$, δ): 1.13 (t, J=6.9 Hz, 3H), 1.94-2.04 (m, 2H), 3.25 (s, 3H), 4.12 (brs, 2H), 6.87 (brs, 1H), 7.56-7.30 (m, 6H), 9.00 (s, 1H).
Compound 36: ESIMS m/z: 489 (M+H)$^+$.

EXAMPLE 36

N-(3-(2,2,2-trifluoro-1-(6-(2-hydroxypropan-2-yl)pyridin-3-yl)ethoxy)quinoxalin-2-yl)propane-1-sulfonamide (Compound 37)

According to Example 13, Compound 37 (63.0 mg, 61% yield) was obtained from Compound A12 (83.1 mg, 0.209 mmol) obtained in Reference Example 12.
ESIMS m/z: 490 (M+H)$^+$.

EXAMPLE 37

N-(3-(2,2,2-trifluoro-1-(6-(methylthio)pyridin-3-yl)ethoxy) quinoxalin-2-yl)butane-1-sulfonamide (Compound 38)

According to Example 1, Compound 38 (179 mg, 57% yield) was obtained from Compound A2 (195 mg, 0.650 mmol) obtained in Reference Example 2 and Compound A27 (145 mg, 0.650 mmol) obtained in Reference Example 27.
ESIMS m/z: 487 (M+H)$^+$.

EXAMPLE 38

N-(3-(2,2,2-trifluoro-1-(6-(2-hydroxypropan-2-yl)pyridin-3-yl)ethoxy)quinoxalin-2-yl)butane-1-sulfonamide (Compound 39)

According to Example 13, Compound 39 (67.9 mg, 55% yield) was obtained from Compound A12 (98.5 mg, 0.248 mmol) obtained in Reference Example 12.
ESIMS m/z: 499 (M+H)$^+$.

EXAMPLE 39

N-(3-(2,2,2-trifluoro-1-(6-(methylsulfonyl)pyridin-3-yl)ethoxy)quinoxalin-2-yl)butane-1-sulfonamide (Compound 40)

N-(3-(2,2,2-trifluoro-1-(6-(methylsulfinyl)pyridin-3-yl)ethoxy)quinoxalin-2-yl)butane-1-sulfonamide (Compound 41)

According to Example 35, Compound 40 (70.6 mg, 44% yield) and Compound 41 (85.1 mg, 55% yield) were obtained from Compound 38 (149 mg, 0.306 mmol) obtained in Example 37.
Compound 40: ESIMS m/z: 519 (M+H)$^+$.
Compound 41: ESIMS m/z: 503 (M+H)$^+$.

EXAMPLE 40

N-(3-(2,2,2-trifluoro-1-(pyridin-4-yl)ethoxy)quinoxalin-2-yl)propane-1-sulfonamide (Compound 42)

Step 1

N-(3-(2,2,2-trifluoro-1-(pyridin-4-yl)ethoxy)quinoxalin-2-yl)-N-((2-(trimethylsilyl)ethoxy)methyl)propane-1-sulfonamide (Compound B3)

According to Example 1, Compound B3 (251 mg, 80% yield) was obtained from Compound A5 (258 mg, 0.621 mmol) obtained in Reference Example 5 and Compound A28 (100 mg, 0.565 mmol) obtained in Reference Example 28.
ESIMS m/z: 557 (M+H)$^+$.

Step 2

N-(3-(2,2,2-trifluoro-1-(pyridin-4-yl)ethoxy)quinoxalin-2-yl)propane-1-sulfonamide (Compound 42)

Compound B3 (48.9 mg, 0.0880 mmol) obtained in Step 1 was dissolved in trifluoroacetic acid (1.0 mL) and the solution was stirred at room temperature for 20 minutes. The solvent was evaporated under reduced pressure. The residue was purified by silica gel column chromatography (hexane/ethyl acetate=1/1) to give Compound 42 (38.6 mg, 100% yield).
ESIMS m/z: 427 (M+H)$^+$.

EXAMPLE 41

4-(2,2,2-trifluoro-1-(3-(propylsulfonamido)quinoxalin-2-yloxy)ethyl)pyridine 1-oxide (Compound 43)

According to Example 2, Compound 43 (41.0 mg, 68% yield) was obtained from Compound 42 (58.5 mg, 0.137 mmol) obtained in Example 40.
ESIMS m/z: 443 (M+H)$^+$.
$^1$H-NMR (270 MHz, CDCl$_3$, δ): 1.14 (t, J=7.7 Hz, 3H), 1.93-2.07 (m, 2H), 3.72-3.86 (m, 2H), 6.55-6.76 (m, 1H), 7.42-7.96 (m, 6H), 8.24 (d, J=7.0 Hz, 2H).

EXAMPLE 42

N-(3-(1-(2-cyanopyridin-4-yl)-2,2,2-trifluoroethoxy)quinoxalin-2-yl)propane-1-sulfonamide (Compound 44)

Step 1

4-(2,2,2-trifluoro-1-(3-(N-((2-(trimethylsilyl)ethoxy)methyl) propylsulfonamido)quinoxalin-2-yloxy)ethyl)pyridine 1-oxide (Compound B4)

According to Example 2, Compound B4 (185 mg, 88% yield) was obtained from Compound B3 (205 mg, 0.368 mmol) obtained in Step 1 of Example 40.
ESIMS m/z: 573 (M+H)$^+$.
Step 2

N-(3-(1-(2-cyanopyridin-4-yl)-2,2,2-trifluoroethoxy)quinoxalin-2-yl)-N-((2-(trimethylsilyl)ethoxy)methyl) propane-1-sulfonamide (Compound B5)

Compound B4 (210 mg, 0.367 mmol) obtained in Step 1 was dissolved in dichloromethane (4 mL). To the solution were added trimethylsilyl cyanide (0.25 mL, 1.8 mmol) and dimethylcarbamoyl chloride (0.17 mL, 1.8 mmol), and the mixture was refluxed for 24 hours. A saturated aqueous sodium bicarbonate solution and water were added to the reaction mixture. Extraction with ethyl acetate and drying over anhydrous sodium sulfate were performed. After filtration, the solvent in the filtrate was evaporated under reduced pressure. The residue was purified by silica gel column chromatography (hexane/ethyl acetate=1/1) to give Compound B5 (218 mg, 100% yield).
Step 3

N-(3-(1-(2-cyanopyridin-4-yl)-2,2,2-trifluoroethoxy)quinoxalin-2-yl)propane-1-sulfonamide (Compound 44)

According to Step 2 of Example 40, Compound 44 (27.7 mg, 87% yield) was obtained from Compound B5 (41.0 mg, 0.0700 mmol) obtained in Step 2.
ESIMS m/z: 452 (M+H)$^+$.

$^1$H-NMR (270 MHz, CDCl$_3$, δ): 1.15 (t, J=7.7 Hz, 3H), 1.95-2.08 (m, 2H), 3.81 (t, J=7.7 Hz, 2H), 6.64-6.79 (m, 1H), 7.32-7.96 (m, 6H), 8.83 (d, J=5.1 Hz, 1H).

EXAMPLE 43

N-(3-(1-(2-aminopyridin-4-yl)-2,2,2-trifluoroethoxy)quinoxalin-2-yl)propane-1-sulfonamide (Compound 45)

Compound B4 (200 mg, 0.349 mmol) obtained in Step 1 of Example 42 was suspended in benzotrifluoride (10 mL). To the suspension were added tert-butylamine (0.19 mL, 1.7 mmol) and p-toluenesulfonic anhydride (228 mg, 0.698 mmol), and the mixture was stirred at room temperature for 18 hours. To the reaction mixture were added tert-butylamine (0.19 mL, 1.7 mmol) and p-toluenesulfonic anhydride (228 mg, 0.698 mmol) and the mixture was further stirred at room temperature for 18 hours. Further, to the reaction mixture were added tert-butylamine (0.19 mL, 1.7 mmol) and p-toluenesulfonic anhydride (228 mg, 0.698 mmol) and the mixture was further stirred at room temperature for 18 hours. A saturated aqueous sodium bicarbonate solution and water were added to the reaction mixture. Extraction with ethyl acetate and drying over anhydrous sodium sulfate were performed. After filtration, the solvent in the filtrate was evaporated under reduced pressure. The residue was dissolved in benzotrifluoride (2.0 mL) and trifluoroacetic acid (2.0 mL) and the solution was stirred at 70° C. for 18 hours. The solvent was evaporated under reduced pressure, and a saturated aqueous sodium bicarbonate solution and water were added to the residue. Extraction with ethyl acetate and drying over anhydrous sodium sulfate were performed. After filtration, the solvent in the filtrate was evaporated under reduced pressure. The residue was purified by silica gel column chromatography (chloroform/methanol=1/10) to give Compound 45 (83.2 mg, 54% yield).
ESIMS m/z: 442 (M+H)$^+$.
$^1$H-NMR (270 MHz, CDCl$_3$, δ): 1.13 (t, J=7.4 Hz, 3H), 1.96-2.06 (m, 2H), 4.55-4.59 (m, 2H), 6.69 (s, 1H), 6.58-6.70 (m, 1H), 6.83 (d, J=5.3 Hz, 1H), 7.42-7.73 (m, 4H), 8.13 (d, J=5.3 Hz, 1H).

EXAMPLE 44

N-(3-(2,2,2-trifluoro-1-(pyridin-4-yl)ethoxy)quinoxalin-2-yl)butane-1-sulfonamide (Compound 46)

Step 1

N-(3-(2,2,2-trifluoro-1-(pyridin-4-yl)ethoxy)quinoxalin-2-yl)-N-((2-(trimethylsilyl)ethoxy)methyl) butane-1-sulfonamide (Compound B6)

According to Example 1, Compound B6 (410 mg, 31% yield) was obtained from compound A6 (1.08 g, 2.52 mmol) obtained in Reference Example 6 and Compound A28 (405 mg, 2.29 mmol) obtained in Reference Example 28.
Step 2

N-(3-(2,2,2-trifluoro-1-(pyridin-4-yl)ethoxy)quinoxalin-2-yl)butane-1-sulfonamide (Compound 46)

According to the method in Step 2 of Example 40, Compound 46 (91.8 mg, 74% yield) was obtained from Compound B6 (160 mg, 0.280 mmol) obtained in Step 1.
ESIMS m/z: 441 (M+H)$^+$.

EXAMPLE 45

4-(1-(3-(butylsulfonamido)quinoxalin-2-yloxy)-2,2,2-trifluoroethyl)pyridine 1-oxide (Compound 47)

According to Example 2, Compound 47 (35.4 mg, 63% yield) was obtained from Compound 46 (54.0 mg, 0.123 mmol) obtained in Example 44.
ESIMS m/z: 457 (M+H)$^+$.

EXAMPLE 46

N-(3-(1-(2,3-dihydrobenzo[b][1,4]dioxin-6-yl)-2,2,2-trifluoroethoxy)quinoxalin-2-yl)propane-1-sulfonamide (Compound 48)

According to Example 1, Compound 48 (77.6 mg, 75% yield) was obtained from Compound A1 (67.1 mg, 0.235 mmol) obtained in Reference Example 1 and Compound A29 (50.0 mg, 0.214 mmol) obtained in Reference Example 29.
ESIMS m/z: 484 (M+H)$^+$.

EXAMPLE 47

N-methyl-N-(4-(2,2,2-trifluoro-1-(3-(propylsulfonamido)quinoxalin-2-yloxy)ethyl)pyridin-2-yl)acetamide (Compound 49)

Step 1

N-methyl-N-(4-(2,2,2-trifluoro-1-(3-(N-((2-(trimethylsilyl)ethoxy)methyl)propylsulfonamido)quinoxalin-2-yloxy)ethyl)pyridin-2-yl)acetamide (Compound B7)

N-methylacetamide (0.097 mL, 1.30 mmol) was dissolved in dichloromethane (1.0 mL). To the solution were added at 0° C. 2,6-lutidine (0.30 mL, 2.5 mmol) and oxalyl dichloride (0.11 mL, 1.30 mmol). After stirring at the same temperature for 15 minutes, a solution of Compound B4 (145 mg, 0.253 mmol) obtained in Step 1 of Example 42 in dichloromethane (1.0 mL) was added and the mixture was further stirred at room temperature for 18 hours. A saturated aqueous sodium bicarbonate solution and water were added to the reaction mixture. Extraction with ethyl acetate and drying over anhydrous sodium sulfate were performed. After filtration, the solvent in the filtrate was evaporated under reduced pressure. The residue was purified by silica gel column chromatography (chloroform/methanol=1/10) to give Compound B7 (157 mg, 99% yield).
ESIMS m/z: 628 (M+H)$^+$.
Step 2

N-methyl-N-(4-(2,2,2-trifluoro-1-(3-(propylsulfonamido)quinoxalin-2-yloxy)ethyl)pyridin-2-yl)acetamide (Compound 49)

According to the method in Step 2 of Example 40, Compound 49 (98.8 mg, 79% yield) was obtained from Compound B7 (157 mg, 0.250 mmol) obtained in Step 1.
ESIMS m/z: 498 (M+H)$^+$.
$^1$H-NMR (270 MHz, CDCl$_3$, δ): 1.13 (t, J=7.3 Hz, 3H), 1.95-2.07 (m, 2H), 2.18 (s, 3H), 3.44 (s, 3H), 3.80 (t, J=7.0 Hz, 2H), 6.76 (q, J=6.6 Hz, 1H), 7.31-7.94 (m, 6H), 8.53 (d, J=5.1 Hz, 1H).

EXAMPLE 48

1-cyclopropyl-N-(3-(2,2,2-trifluoro-1-(pyridin-4-yl)ethoxy)quinoxalin-2-yl)methanesulfonamide (Compound 50)

According to the method in Example 40, Compound 50 (33.5 mg, 2 steps 64% yield) was obtained from Compound A8 (55.8 mg, 0.130 mmol) obtained in Reference Example 8 and Compound A28 (21.0 mg, 0.119 mmol) obtained in Reference Example 28.
ESIMS m/z: 439 (M+H)$^+$.

EXAMPLE 49

2-methyl-N-(3-(2,2,2-trifluoro-1-(pyridin-4-yl)ethoxy)quinoxalin-2-yl)propane-1-sulfonamide (Compound 51)

According to the method in Example 40, Compound 51 (37.3 mg, 2 steps 66% yield) was obtained from Compound A7 (61.5 mg, 0.143 mmol) obtained in Reference Example 7 and Compound A28 (23.0 mg, 0.130 mmol) obtained in Reference Example 28.
ESIMS m/z: 441 (M+H)$^+$.

EXAMPLE 50

N-(3-(1-(2-cyanopyridin-4-yl)-2,2,2-trifluoroethoxy)quinoxalin-2-yl)butane-1-sulfonamide (Compound 52)

According to the method in Example 42, Compound 52 (51.6 mg, 3 steps 70% yield) was obtained from Compound B6 (89.7 mg, 0.157 mmol) obtained in Step 1 of Example 44.
ESIMS m/z: 466 (M+H)$^+$.

EXAMPLE 51

N-(3-(2,2,2-trifluoro-1-(2-methylimidazo[1,2-a]pyridin-7-yl)ethoxy)quinoxalin-2-yl)propane-1-sulfonamide (Compound 53)

According to Example 40, Compound 53 (7.2 mg, 2 steps 40% yield) was obtained from Compound A5 (35.8 mg, 0.0860 mmol) obtained in Reference Example 5 and Compound A30 (18.0 mg, 0.0780 mmol) obtained in Reference Example 30.
ESIMS m/z: 480 (M+H)$^+$.

EXAMPLE 52

N-(3-(1-(2-(1H-imidazol-1-yl)pyridin-4-yl)-2,2,2-trifluoroethoxy)quinoxalin-2-yl)propane-1-sulfonamide (Compound 54)

Step 1

N-(3-(1-(2-(1H-imidazol-1-yl)pyridin-4-yl)-2,2,2-trifluoroethoxy)quinoxalin-2-yl)-N-((2-(trimethylsilyl)ethoxy)methyl)propane-1-sulfonamide (Compound B8)

Compound B4 (137 mg, 0.240 mmol) obtained in Step 1 of Example 42 was suspended in toluene (2.4 mL), 1,1'-sulfonyldiimidazole (190 mg, 0.960 mmol) was added, and the mixture was refluxed for 6 days. A 1 mol/L aqueous sodium hydroxide solution was added to the reaction mixture. Extraction with dichloromethane and drying over anhydrous sodium sulfate were performed. After filtration, the solvent in the filtrate was evaporated under reduced pressure. The residue was purified by silica gel column chromatography (ethyl acetate: 100%) to give Compound B8 (19.3 mg, 13% yield).
Step 2

N-(3-(1-(2-(1H-imidazol-1-yl)pyridin-4-yl)-2,2,2-trifluoroethoxy)quinoxalin-2-yl)propane-1-sulfonamide (Compound 54)

According to the method in Step 2 of Example 40, Compound 54 (13.1 mg, 97%) was obtained from Compound B8 (17.0 mg, 0.0270 mmol) obtained in Step 1.
ESIMS m/z: 493 (M+H)$^+$.

EXAMPLE 53

N-(3-(2,2,2-trifluoro-1-(2-(methylthio)pyrimidin-5-yl)ethoxy)quinoxalin-2-yl)propane-1-sulfonamide (Compound 55)

According to Example 1, Compound 55 (37.0 mg, 31% yield) was obtained from Compound A1 (81.0 mg, 0.282 mmol) obtained in Reference Example 1 and Compound A31 (57.5 mg, 0.256 mmol) obtained in Reference Example 31.
ESIMS m/z: 474 (M+H)$^+$.

EXAMPLE 54

N-(3-(1-(2-(1,2,4-oxadiazol-3-yl)pyridin-4-yl)-2,2,2-trifluoroethoxy)quinoxalin-2-yl)propane-1-sulfonamide (Compound 56)

Step 1

N-(3(1-(2-(1,2,4-oxadiazol-3-yl)pyridin-4-yl)-2,2,2-trifluoroethoxy)quinoxalin-2-yl)-N-((2-(trimethylsilyl)ethoxy)methyl)propane-1-sulfonamide (Compound B9)

Compound B5 (90.5 mg, 0.156 mmol) obtained in Step 2 of Example 42 was dissolved in a 50% aqueous hydroxylamine solution (1.0 mL) and ethanol (1.0 mL) and the solution was stirred at room temperature for 30 minutes. The solvent was evaporated under reduced pressure and the residue was dissolved in triethyl orthoformate (1.0 mL). The mixture was stirred at 100° C. for 23 hours and further stirred at 130° C. for 18 hours. The solvent was evaporated under reduced pressure. The residue was purified by silica gel column chromatography (hexane/ethyl acetate=1/1) to give Compound B9 (67.7 mg, 70% yield).
Step 2

N-(3-(1-(2-(1,2,4-oxadiazol-3-yl)pyridin-4-yl)-2,2,2-trifluoroethoxy)quinoxalin-2-yl)propane-1-sulfonamide (Compound 56)

According to the method in Step 2 of Example 40, Compound 56 (34.0 mg, 64% yield) was obtained from Compound B9 (67.7 mg, 0.108 mmol) obtained in Step 1.
ESIMS m/z: 495 (M+H)$^+$.

EXAMPLE 55

N-(3-(1-(benzo[d][1,3]dioxol-5-yl)-2,2,2-trifluoroethoxy)quinoxalin-2-yl)propane-1-sulfonamide (Compound 57)

According to Example 1, Compound 57 (65.0 mg, 32% yield) was obtained from Compound A1 (138 mg, 0.482 mmol) obtained in Reference Example 1 and Compound A32 (96.4 mg, 0.438 mmol) obtained in Reference Example 32.
ESIMS m/z: 470 (M+H)$^+$.

EXAMPLE 56

N-(3-(2,2,2-trifluoro-1-(2-(methylamino)pyrimidin-5-yl)ethoxy)quinoxalin-2-yl)propane-1-sulfonamide (Compound 58)

Step 1

N-(3-(2,2,2-trifluoro-1-(2-(methylthio)pyrimidin-5-yl)ethoxy)quinoxalin-2-yl)-N-((2-(trimethylsilyl)ethoxy)methyl)propane-1-sulfonamide (Compound B10)

According to Example 1, Compound B10 (132 mg, 95%) was obtained from Compound A5 (106 mg, 0.254 mmol) obtained in Reference Example 5 and Compound A31 (51.8 mg, 0.231 mmol) obtained in Reference Example 31.
ESIMS m/z: 604 (M+H)$^+$.
Step 2

N-(3-(2,2,2-trifluoro-1-(2-(methylamino)pyrimidin-5-yl)ethoxy)quinoxalin-2-yl)-N-((2-(trimethylsilyl)ethoxy)methyl) propane-1-sulfonamide (Compound B11)

Compound B10 (51.0 mg, 0.0840 mmol) obtained in Step 1 was dissolved in dichloromethane (1.0 mL), 65%-metachloroperbenzoic acid (38.9 mg, 0.169 mmol) was added at 0° C., and the mixture was stirred at room temperature for 1 hour. A saturated aqueous sodium bicarbonate solution was added to the reaction mixture. Extraction with chloroform and drying over anhydrous sodium sulfate were performed. After filtration, the solvent in the filtrate was evaporated under reduced pressure and the residue was dissolved in THF (1.0 mL). Methylamine (2 mol/L solution in THF, 1.0 mL) was added and the mixture was stirred at room temperature for 18 hours. The solvent was evaporated under reduced pressure. The residue was purified by silica gel column chromatography (hexane/ethyl acetate=1/1) to give Compound B11 (44.3 mg, 89% yield).
ESIMS m/z: 587 (M+H)$^+$.
Step 3

N-(3-(2,2,2-trifluoro-1-(2-(methylamino)pyrimidin-5-yl)ethoxy)quinoxalin-2-yl)propane-1-sulfonamide (Compound 58)

According to the method in Step 2 of Example 40, Compound 58 (25.0 mg, 73% yield) was obtained from Compound B11 (44.3 mg, 0.076 mmol) obtained in Step 2.
ESIMS m/z: 457 (M+H)$^+$.

EXAMPLE 57

N-(3-(2,2,2-trifluoro-1-(1H-indazol-6-yl)ethoxy)quinoxalin-2-yl)propane-1-sulfonamide (Compound 59)

Step 1

Tert-butyl 6-(2,2,2-trifluoro-1-(3-(N-((2-(trimethylsilyl)ethoxy)methyl)propylsulfonamido)quinoxalin-2-yloxy)ethyl)-1H-indazole-1-carboxylate (Compound B12)

According to the method in Step 1 of Example 40, Compound B12 (74.9 mg, 68% yield) was obtained from Compound A5 (72.3 mg, 0.174 mmol) obtained in Reference Example 5 and Compound A33 (50.0 mg, 0.158 mmol) obtained in Reference Example 33.

Step 2

N-(3-(2,2,2-trifluoro-1-(1H-indazol-6-yl)ethoxy)quinoxalin-2-yl)propane-1-sulfonamide (Compound 59)

Compound B12 (74.9 mg, 0.108 mmol) obtained in Step 1 was dissolved in dichloromethane (1 mL). Triethylsilane (0.52 mL, 3.2 mmol) and trifluoroacetic acid (0.25 mL, 3.2 mmol) were added at 0° C. and the mixture was stirred at room temperature for 18 hours. A saturated aqueous sodium bicarbonate solution and water were added to the reaction mixture. Extraction with ethyl acetate and drying over anhydrous sodium sulfate were performed. After filtration, the solvent in the filtrate was evaporated under reduced pressure. The residue was purified by silica gel column chromatography (hexane/ethyl acetate=1/1) to give Compound 59 (40.3 mg, 80. % yield).

ESIMS m/z: 466 (M+H)$^+$.

EXAMPLE 58

N-(3-(2,2,2-trifluoro-1-(1H-indazol-5-yl)ethoxy)quinoxalin-2-yl)propane-1-sulfonamide (Compound 60)

According to Example 57, Compound 60 (34.8 mg, 2 steps 69% yield) was obtained from Compound A5 (72.3 mg, 0.174 mmol) obtained in Reference Example 5 and Compound A34 (50.0 mg, 0.158 mmol) obtained in Reference Example 34.

ESIMS m/z: 466 (M+H)$^+$.

EXAMPLE 59

N-(3-(2,2,2-trifluoro-1-(pyrimidin-5-yl)ethoxy)quinoxalin-2-yl)propane-1-sulfonamide (Compound 61)

According to Example 40, Compound 61 (63.6 mg, 2 steps 810 yield) was obtained from Compound A5 (84.5 mg, 0.203 mmol) obtained in Reference Example 5 and Compound A35 (32.8 mg, 0.184 mmol) obtained in Reference Example 35.

ESIMS m/z: 428 (M+H)$^+$.

EXAMPLE 60

N-(3-(2,2,2-trifluoro-1-(2-methylpyrimidin-5-yl)ethoxy) quinoxalin-2-yl)propane-1-sulfonamide (Compound 62)

According to Example 40, Compound 62 (57.9 mg, 2 steps 77% yield) was obtained from Compound A5 (124 mg, 0.298 mmol) obtained in Reference Example 5 and Compound A36 (52.0 mg, 0.271 mmol) obtained in Reference Example 36.

ESIMS m/z: 442 (M+H)$^+$.

EXAMPLE 61

N-(3-(2,2,2-trifluoro-1-(5-(methylsulfonyl)pyridin-3-yl)ethoxy)quinoxalin-2-yl)propane-1-sulfonamide (Compound 63)

According to Example 13, Compound 63 (42.9 mg, 52% yield) was obtained from Compound A13 (69.0 mg, 0.165 mmol) obtained in Reference Example 13.

ESIMS m/z: 505 (M+H)$^+$.

EXAMPLE 62

N-(3-(2,2,2-trifluoro-1-(6-(2-methyl-2H-1,2,3-triazol-4-yl)pyridin-3-yl)ethoxy)quinoxalin-2-yl)propane-1-sulfonamide (Compounds 64, 64A, and 64B)

According to Example 1, Compound 64 (451 mg, 39% yield) was obtained from Compound A1 (656 mg, 2.30 mmol) obtained in Reference Example 1 and Compound A43 (593 mg, 2.30 mmol) obtained in Reference Example 43.

Separation of Compound 64 by preparative high performance liquid chromatography in the same manner as in Example 66 gave the enantiomers, Compound 64A and Compound 64B. The compound with a shorter retention time is defined as Compound 64B, and the compound with a longer retention time is defined as Compound 64A.

Compound 64: ESIMS m/z: 508 (M+H)$^+$.
Compound 64A: ESIMS m/z: 508 (M'+H)$^+$.
Compound 64B: ESIMS m/z: 508 (M+H)$^+$.

EXAMPLE 63

N-(3-(2,2,2-trifluoro-1-(6-(oxazol-5-yl)pyridin-3-yl)ethoxy) quinoxalin-2-yl)propane-1-sulfonamide (Compound 65)

According to Example 1, Compound 65 (23.0 mg, 18% yield) was obtained from compound A1 (72.0 mg, 0.251 mmol) obtained in Reference Example 1 and Compound A44 (61.4 mg, 0.251 mmol) obtained in Reference Example 44.

ESIMS m/z: 494 (M+H)$^+$.

EXAMPLE 64

N-(3-(2,2,2-trifluoro-1-(6-(5-methyl-1,2,4-oxadiazol-3-yl)pyridin-3-yl)ethoxy)quinoxalin-2-yl)propane-1-sulfonamide (Compound 66)

According to Example 13, Compound 66 (54.5 mg, 32% yield) was obtained from Compound A38 (143 mg, 0.339 mmol) obtained in Reference Example 38.

ESIMS m/z: 509 (M+H)$^+$.

EXAMPLE 65

2-methoxy-N-(3-(2,2,2-trifluoro-1-(6-(1-methyl-1H-pyrazol-5-yl)pyridin-3-yl)ethoxy)quinoxalin-2-yl)ethanesulfonamide (Compound 67)

According to Example 13, Compound 67 (108 mg, 59% yield) was obtained from Compound A39 (144 mg, 0.343 mmol) obtained in Reference Example 39.

ESIMS m/z: 523 (M+H)$^+$.

EXAMPLE 66

2-methoxy-N-(3-(2,2,2-trifluoro-1-(6-(2-methyl-2H-1,2,3-triazol-4-yl)pyridin-3-yl)ethoxy)quinoxalin-2-yl)ethanesulfonamide (Compounds 68, 68A, and 68B)

According to Example 13, Compound 68 (449 mg, 68% yield) was obtained from Compound A40 (528 mg, 1.26 mmol) obtained in Reference Example 40.

Separation of Compound 68 (980 mg) by preparative high performance liquid chromatography [CHIRALPAK (registered trademark) IC (Daicel Chemical Industries, Ltd.); particle size: 5 μm; 2 cm (internal diameter)×25 cm (length); chloroform: 100%; flow rate: 5.7 mL/min; column oven temperature: 40° C.; detection wavelength: 304 nm] gave the enantiomers, Compound 68A (440 mg) and Compound 68B (450 mg). The compound with 16 minutes retention time is defined as Compound 68A, and the compound with 30 minutes retention time is defined as Compound 68B.

Compound 68: ESIMS m/z: 524 $(M+H)^+$.
Compound 68A: ESIMS m/z: 524 $(M+H)^+$.
Compound 68B: ESIMS m/z: 524 $(M+H)^+$.

EXAMPLE 67

2-methoxy-N-(3-(2,2,2-trifluoro-1-(6-(2-methyl-1H-imidazol-1-yl)pyridin-3-yl)ethoxy)quinoxalin-2-yl)ethanesulfonamide (Compound 69)

According to Example 13, Compound 69 (23.9 mg, 18% yield) was obtained from Compound A41 (104 mg, 0.248 mmol) obtained in Reference Example 41.
ESIMS m/z: 523 $(M+H)^+$.

EXAMPLE 68

N-(3-(1-(1,2-dimethyl-1H-imidazol-5-yl)-2,2,2-trifluoroethoxy)quinoxalin-2-yl)propane-1-sulfonamide (Compound 70)

According to Example 1, Compound 70 (38.9 mg, 320) was obtained from Compound A1 (82.0 mg, 0.286 mmol) obtained in Reference Example 1 and Compound A45 (52.8 mg, 0.272 mmol) obtained in Reference Example 45.
ESIMS m/z: 444 $(M+H)^+$.

EXAMPLE 69

N-(3-(1-(2-acetylthiazol-5-yl)-2,2,2-trifluoroethoxy)quinoxalin-2-yl)propane-1-sulfonamide (Compound 71)

Step 1

N-(3-(1-(2-acetylthiazol-5-yl)-2,2,2-trifluoroethoxy)quinoxalin-2-yl)-N-((2-(trimethylsilyl)ethoxy)methyl) propane-1-sulfonamide (Compound B13)

According to Example 1, Compound B13 (55.8 mg, 400) was obtained from Compound A5 (105 mg, 0.253 mmol) obtained in Reference Example 5 and Compound A46 (51.7 mg, 0.230 mmol) obtained in Reference Example 46.

Step 2

N-(3-(1-(2-acetylthiazol-5-yl)-2,2,2-trifluoroethoxy)quinoxalin-2-yl)propane-1-sulfonamide (Compound 71)

According to Step 2 of Example 40, Compound 71 (43.2 mg, 99%) was obtained from Compound B13 (55.8 mg, 0.092 mmol) obtained in Step 1.
ESIMS m/z: 475 $(M+H)^+$.

EXAMPLE 70

N-(3-(1-(2-acetylpyridin-4-yl)-2,2,2-trifluoroethoxy)quinoxalin-2-yl)-2-methoxyethanesulfonamide (Compound 72)

According to Example 13, Compound 72 (78.1 mg, 29%) was obtained from Compound A42 (211 mg, 0.552 mmol) obtained in Reference Example 42 and 2-methoxyethanesulfonamide (115 mg, 0.828 mmol) obtained in Step 1 of Reference Example 37.
ESIMS m/z: 485 $(M+H)^+$.

EXAMPLE 71

2-methoxy-N-(3-(2,2,2-trifluoro-1-(6-(oxazol-5-yl)pyridin-3-yl)ethoxy)quinoxalin-2-yl)ethanesulfonamide (Compound 73)

Step 1

2-methoxy-N-(3-(2,2,2-trifluoro-1-(6-(oxazol-5-yl)pyridin-3-yl)ethoxy)quinoxalin-2-yl)-N-((2-(trimethylsilyl)ethoxy)methyl)ethanesulfonamide (Compound B14)

According to Example 1, Compound B14 (193 mg, 92%) was obtained from Compound A37 (156 mg, 0.360 mmol) obtained in Reference Example 37 and Compound A44 (80.0 mg, 0.328 mmol) obtained in Reference Example 44.

Step 2

2-methoxy-N-(3-(2,2,2-trifluoro-1-(6-(oxazol-5-yl)pyridin-3-yl)ethoxy)quinoxalin-2-yl)ethanesulfonamide (Compound 73)

According to Step 2 of Example 40, Compound 73 (146 mg, 95%) was obtained from Compound B14 (193 mg, 0.302 mmol) obtained in Step 1.
ESIMS m/z: 510 $(M+H)^+$.

EXAMPLE 72

N-(3-(1-(2-acetylthiazol-5-yl)-2,2,2-trifluoroethoxy)quinoxalin-2-yl)-2-methoxyethanesulfonamide (Compound 74)

Step 1

N-(3-(1-(2-acetylthiazol-5-yl)-2,2,2-trifluoroethoxy)quinoxalin-2-yl)-2-methoxy-N-((2-(trimethylsilyl)ethoxy)methyl)ethanesulfonamide (Compound B15)

According to Example 1, Compound B15 (93.0 mg, 48%) was obtained from Compound A5 (109 mg, 0.253 mmol)

obtained in Reference Example 5 and Compound A46 (51.7 mg, 0.230 mmol) obtained in Reference Example 46.

Step 2

N-(3-(1-(2-acetylthiazol-5-yl)-2,2,2-trifluoroethoxy) quinoxalin-2-yl)-2-methoxyethanesulfonamide (Compound 74)

According to Step 2 of Example 40, Compound 74 (55.4 mg, 49%) was obtained from Compound B15 (143 mg, 0.230 mmol) obtained in Step 1.

ESIMS m/z: 491 (M+H)$^+$.

EXAMPLE 73

N-(3-(2,2,2-trifluoro-1-(6-(1-methyl-1H-pyrazol-4-yl)pyridin-3-yl)ethoxy)quinoxalin-2-yl)propane-1-sulfonamide (Compounds 75 and 76)

Separation of Compound 32 obtained in Example 32 by preparative high performance liquid chromatography in the same manner as in Example 66 gave the enantiomers, Compounds 75 and
76. The compound with a shorter retention time is defined as Compound 75, and the compound with a longer retention time is defined as Compound 76.

Compound 75: ESIMS m/z: 507 (M+H)$^+$.
Compound 76: ESIMS m/z: 507 (M+H)$^+$.

EXAMPLE 74

N-(7-iodo-3-(2,2,2-trifluoro-1-(pyridin-3-yl)ethoxy) quinoxalin-2-yl)propane-1-sulfonamide (Compound 77)

According to Example 13, Compound 77 (725 mg, 73% yield) was obtained from Compound A47 (222 mg, 1.81 mmol) obtained in Reference Example 47.

ESIMS m/z: 553 (M+H)$^+$; $^1$H-NMR (270 MHz, CDCl$_3$, δ): 1.13 (t, J=7.3 Hz, 3H), 1.93-2.05 (m, 2H), 3.66-3.85 (m, 2H), 6.76 (q, J=6.5 Hz, 1H), 7.35-7.47 (m, 2H), 7.73-7.85 (m, 1H), 7.94 (d, J=8.1 Hz, 1H), 8.22-8.34 (m, 1H), 8.69 (dd, J=4.9, 1.8 Hz, 1H), 8.87 (d, J=1.8 Hz, 1H).

EXAMPLE 75

N-(7-cyano-3-(2,2,2-trifluoro-1-(pyridin-3-yl) ethoxy) quinoxalin-2-yl)propane-1-sulfonamide (Compound 78)

Compound 77 (41.0 mg, 0.074 mmol) obtained in Example 74 was dissolved in DMA (1.60 mL). To the solution were added zinc cyanide (21.8 mg, 1.11 mmol), zinc (1.17 mg, 0.018 mmol), tris(dibenzylideneacetone)dipalladium (2.72 mg, 0.003 mmol) and 1,1'-bis(diphenylphosphino)ferrocene (2.67 mg, 0.005 mmol), and the mixture was stirred at 120° C. for 1 hour. Water was added to the reaction mixture and the mixture was filtered through Celite. The filtrate was extracted with ethyl acetate. Washing with saturated brine and drying over anhydrous magnesium sulfate were performed. After filtration, the solvent in the filtrate was evaporated under reduced pressure. The residue was purified by silica gel column chromatography (hexane/ethyl acetate=1/0 to 2/3) to give Compound 78 (14.0 mg, 42% yield).

ESIMS m/z: 452 (M+H)$^+$; $^1$H-NMR (270 MHz, CDCl$_3$, δ): 1.14 (t, J=7.3 Hz, 3H), 1.93-2.09 (m, 2H), 3.68-3.84 (m, 2H), 6.79 (q, J=6.4 Hz, 1H), 7.42 (dd, J=7.9, 4.9 Hz, 1H), 7.69-7.85 (m, 2H), 7.95 (d, J=7.9 Hz, 1H), 8.19-8.28 (m, 1H), 8.71 (dd, J=4.9, 1.8 Hz, 1H), 8.88 (d, J=1.8 Hz, 1H).

EXAMPLE 76

N-(7-ethynyl-3-(2,2,2-trifluoro-1-(pyridin-3-yl) ethoxy) quinoxalin-2-yl)propane-1-sulfonamide (Compound 79)

Compound 77 (70.0 mg, 0.127 mmol) obtained in Example 74 was dissolved in DMF (2.00 mL). To the solution were added trimethylsilylacetylene (0.089 mL, 0.634 mmol), triethylamine (0.088 mL, 0.634 mmol), copper iodide (I) (9.66 mg, 0.051 mmol), and tetrakis (triphenylphosphine)palladium (29.3 mg, 0.025 mmol), and the mixture was stirred at 120° C. for 30 minutes. Water was added to the reaction mixture and the mixture was filtered through Celite. The filtrate was extracted with ethyl acetate. Washing with saturated brine and drying over anhydrous magnesium sulfate were performed. After filtration, the solvent in the filtrate was evaporated under reduced pressure. The resulting residue was purified by silica gel column chromatography (hexane/ethyl acetate=1/0 to 2/3). The obtained purified product was dissolved in THF (1.80 mL). Tetrabutylammonium fluoride (1.0 mol/L solution in THF, 0.107 mL, 0.107 mmol) was added and the mixture was stirred at room temperature for 2 hours. Water was added to the reaction mixture. Extraction with ethyl acetate, washing with saturated brine and drying over anhydrous magnesium sulfate were performed. After filtration, the solvent in the filtrate was evaporated under reduced pressure. The resulting residue was purified by silica gel column chromatography (hexane/ethyl acetate=1/0 to 1/1) to give Compound 79 (25.7 mg, 46% yield).

ESIMS m/z: 451 (M+H)$^+$; $^1$H-NMR (270 MHz, CDCl$_3$, δ): 1.13 (t, J=7.5 Hz, 3H), 1.92-2.07 (m, 2H), 3.20 (s, 1H), 3.69-3.84 (m, 2H), 6.78 (q, J=6.0 Hz, 1H), 7.32-7.50 (m, 1H), 7.55-7.72 (m, 2H), 7.95 (d, J=8.4 Hz, 1H), 8.00-8.08 (m, 1H), 8.45-9.10 (m, 2H).

EXAMPLE 77

Tablets having the following composition are prepared in a usual manner. An amount of 40 g of Compound 3 is mixed with 286.8 g of lactose and 60 g of potato starch. To the mixture is added 120 g of a 10% aqueous hydroxypropyl cellulose solution. This mixture is kneaded, granulated, dried, and fine-granulated in a usual manner to prepare granules for tableting. To the mixture is added 1.2 g of magnesium stearate and the mixture is mixed in a usual manner. The mixture is tableted with a tableting machine (Kikusui, Model RT-15) equipped with a pestle, whose diameter is 8 mm, to give tablets (containing 20 mg of the active ingredient per tablet).

| Formula | |
|---|---|
| Compound 3 | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 78

Injections having the following composition are prepared in a usual manner. An amount of 1 g of Compound 8 is added to distilled water for injection and mixed. The pH is adjusted to 7 by adding hydrochloric acid and an aqueous sodium hydroxide solution, and the total volume is made up to 1000 mL with distilled water for injection. Two mL of the mixture is aseptically packed into each glass vial, and thus injections (containing 2 mg of the active ingredient per vial) are obtained.

| Formula | |
|---|---|
| Compound 8 | 2 mg |
| Hydrochloric acid | q.s. |
| Aqueous sodium hydroxide solution | q.s. |
| Distilled water for injection | q.s. |
| | 2.00 mL |

INDUSTRIAL APPLICABILITY

The present invention provides a nitrogen-containing heterocyclic compound having an inhibitory effect on the production of kynurenine or a pharmaceutically acceptable salt thereof; a kynurenine production inhibitor comprising one or more of said compound or salt thereof as an active ingredient; and the like.

The invention claimed is:

1. A nitrogen-containing heterocyclic compound or a pharmaceutically acceptable salt thereof, wherein the nitrogen-containing heterocyclic compound is a compound selected from the group consisting of:

N-(3-(2,2,2-trifluoro-1-(6-(1-methyl-1H-pyrazol-4-yl)pyridin-3-yl)ethoxy) quinoxalin-2-yl) propane-1-sulfonamide, N-(3-(2,2,2-trifluoro-1-(6-(1-methyl-1H-pyrazol-4-yl)pyridin-3-yl)ethoxy)quinoxalin-2-yl)butane-1-sulfonamide, N-(3-(2,2,2-trifluoro-1-(6-(2-methyl-2H-1,2,3-triazol-4-yl)pyridin-3-yl)ethoxy)quinoxalin-2-yl)propane-1-sulfonamide, N-(3-(2,2,2-trifluoro-1-(6-(oxazol-5-yl)pyridin-3-yl)ethoxy)quinoxalin-2-yl)propane-1-sulfonamide, N-(3-(2,2,2-trifluoro-1-(6-(5-methyl-1,2,4-oxadiazol-3-yl)pyridin-3-yl) ethoxy) quinoxalin-2-yl) propane-1-sulfonamide, 2-methoxy-N-(3-(2,2,2-trifluoro-1-(6-(1-methyl-1H-pyrazol-5-yl)pyridin-3-yl) ethoxy) quinoxalin-2-yl) ethanesulfonamide, 2-methoxy-N-(3-(2,2,2-trifluoro-1-(6-(2-methyl-2H-1,2,3-triazol-4-yl)pyridin-3-yl) ethoxy) quinoxalin-2-yl) ethanesulfonamide, 2-methoxy-N-(3-(2,2,2-trifluoro-1-(6-(2-methyl-1H-imidazol-1-yl)pyridin-3-yl)ethoxy)quinoxalin-2-yl) ethanesulfonamide, and 2-methoxy-N-(3-(2,2,2-trifluoro-1-(6-(oxazol-5-yl)pyridin-3-yl)ethoxy)quinoxalin-2-yl)ethanesulfonamide.

* * * * *